United States Patent
Hamprecht et al.

(10) Patent No.: US 8,841,309 B2
(45) Date of Patent: Sep. 23, 2014

(54) SUBSTITUTED PYRAZINES AND THEIR USE IN THE TREATMENT OF DISEASE

(71) Applicants: Dieter Hamprecht, Pozzolengo (IT); Armin Heckel, Biberach an der Riss (DE); Joerg Kley, Mittelbiberach (DE)

(72) Inventors: Dieter Hamprecht, Pozzolengo (IT); Armin Heckel, Biberach an der Riss (DE); Joerg Kley, Mittelbiberach (DE)

(73) Assignee: Boehringer Ingelheim International GmbH, Ingelheim am Rheim (DE)

( * ) Notice: Subject to any disclaimer, the term of this patent is extended or adjusted under 35 U.S.C. 154(b) by 0 days.

(21) Appl. No.: 14/033,552

(22) Filed: Sep. 23, 2013

(65) Prior Publication Data
US 2014/0088097 A1    Mar. 27, 2014

(30) Foreign Application Priority Data
Sep. 24, 2012 (EP) .................................... 12185631

(51) Int. Cl.
| | |
|---|---|
| A61K 31/4965 | (2006.01) |
| C07D 241/16 | (2006.01) |
| C07D 401/12 | (2006.01) |
| A61K 31/498 | (2006.01) |
| C07D 241/32 | (2006.01) |
| C07D 453/02 | (2006.01) |
| A61K 31/5377 | (2006.01) |
| A61K 45/06 | (2006.01) |
| A61K 31/497 | (2006.01) |
| C07D 471/08 | (2006.01) |
| C07D 403/12 | (2006.01) |

(52) U.S. Cl.
CPC ............ *C07D 401/12* (2013.01); *A61K 31/498* (2013.01); *C07D 241/32* (2013.01); *C07D 453/02* (2013.01); *A61K 31/5377* (2013.01); *A61K 45/06* (2013.01); *A61K 31/497* (2013.01); *C07D 471/08* (2013.01); *C07D 403/12* (2013.01)
USPC ...................................... 514/255.06; 544/409

(58) Field of Classification Search
CPC .......................... A61K 31/4965; C07D 241/16
USPC ...................................... 514/255.06; 544/409
See application file for complete search history.

(56) References Cited

U.S. PATENT DOCUMENTS 3,953,476 A    4/1976  Cragoe, Jr. et al.

FOREIGN PATENT DOCUMENTS

| GB | 1214408 A | 12/1970 |
|---|---|---|
| GB | 1214409 A | 12/1970 |
| WO | 2008135557 A1 | 11/2008 |
| WO | 2009138378 A1 | 11/2009 |
| WO | 2013003386 A1 | 1/2013 |
| WO | 2013003444 A1 | 1/2013 |

OTHER PUBLICATIONS

Laeckmann, D. et al., "Synthesis and Biological Evaluation of Aroylguanidines Related to Amilorade as Inhibitors of the Human Platelet Na+/H+Exchanger". Bioorganic Medical Chemistry 2002, 1793-1804.
Alberola, A., et al., "The Reactions of 3-Unsubstituted Isoxazolium Salts with 1,2-Dinucleophiles, Synthesis of 4-Funtionalized 3-Aminoisoxazoles and 3-Aminopyrazoles". Synthesis 1988, 203-207.
Berge, Stephen, M., et al; Review Article: Pharmaceutical Salts; Journal of Pharmaceutical Sciences (1977) vol. 66, No. 1 pp. 1-19.
European Search Report for EP 11187553 Date of Completion of the Search Feb. 10, 2012.
European Search Report for EP 11187566 Date of Completion of the Search May 10, 2012.
European Search Report for EP 11194687 Date of Completion of the Search Mar. 7, 2012.
Hirsch, Andrew, J., et al; Design, Synthesis, and Structure-Activity relationships of Novel 2-Substituted Pyrazinoylguanidine Epithlial Sodium Channel Blockers: Drugs for Cystic Fibrosis and Chronic Brochitis; Journal of Medicinal Chemistry (2006) vol. 49, No. 14 pp. 4098-4115.
Li, Jack, H., et al; Stereoselective Blockade of Amphibian Epithelial Sodium Channels by Amiloride Analogs; The Journal of Pharmacology and Experimental Therapeutics (1993) vol. 267, No. 3 pp. 1081-1084.
Rogister, Francoise, et al; Novel Inhibitors of the Sodium-Calcium Exchanger: Benzene Ring Analogues of N-Guanidino Substituted Amiloride Derivatives; European Journal of Medicinal Chemistry (2001) vol. 36, No. 7-8 pp. 597-614.
Shepard, K.L., et al., Activated Esters of Substituted Pyrazinecarboxylic Acids (1). Journal of Heterocyclic Chemistry, 1976, 1219-1224.
Shepard, Kenneth, L. et al; 3,5-Diamino-6-Chloropyrazinecarboxylic Acid "Active Esters" and Their Reactions (1); Tetrahedron Letters (1969) vol. 54 pp. 4757-4760.
Short, James, H. et al., Sympathetic Nervous System Blocking Agents. Derivates of Guanidine and Related Compounds; Journal of Medicinal Chemistry (1963) vol. 6 pp. 275-283.

(Continued)

*Primary Examiner* — Douglas M Willis
(74) *Attorney, Agent, or Firm* — Michael P. Morris; Edward S. Lazer

(57) ABSTRACT

The present invention relates to compounds of general formula (I)

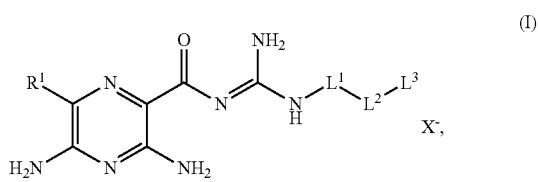

and the tautomers and the salts thereof, particularly the pharmaceutically acceptable salts thereof, which have valuable pharmacological properties, particularly an inhibitory effect on epithelial sodium channels, the use thereof for the treatment of diseases, particularly diseases of the lungs and airways.

3 Claims, No Drawings

(56) References Cited

OTHER PUBLICATIONS

U.S. Appl. No. 13/662,792, filed Oct. 29, 2012, Inventor Joerg Kley.

U.S. Appl. No. 13/662,791, filed Oct. 29, 2012, Inventor Armin Heckel.

Woodman, D.J., "N-t-Butyl-acyloxycrotonamides". Journal of Organic Chemistry, 1970, p. 83-87.

SUBSTITUTED PYRAZINES AND THEIR USE IN THE TREATMENT OF DISEASE

1. FIELD OF THE INVENTION

The present invention relates to compounds of general formula (I)

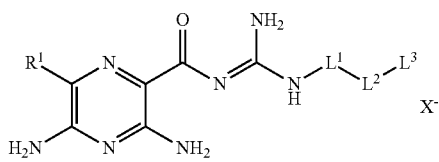

and the tautomers and the salts thereof, particularly the pharmaceutically acceptable salts thereof with inorganic or organic acids and bases, which have valuable pharmacological properties, particularly an inhibitory effect on epithelial sodium channels, the use thereof for the treatment of diseases, particularly diseases of the lungs and airways.

2. BACKGROUND TO THE INVENTION

Amiloride type compounds are known from the prior art as active substances for example for the treatment of diseases of the lungs and airways (*J. Med. Chem.* 49 (2006) 4098-4115). WO 08135557 discloses compounds of similar structure showing ENaC (Epithelial Sodium Channel) inhibitor activity.

The problem of the present invention is to prepare new compounds which may be used therapeutically for the treatment of pathophysiological processes treatable by the blockade of an epithelial sodium channel, particularly for the treatment of the lungs and airways.

3. DETAILED DESCRIPTION OF THE INVENTION

It has surprisingly been found that the problem mentioned above is solved by compounds of formula (I) of the present invention.

The present invention therefore relates to a compound of formula (I)

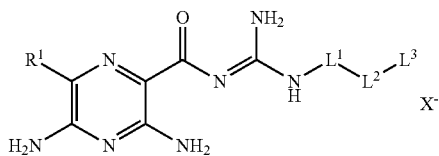

wherein $R^1$ denotes halogen, preferably Cl or Br, particularly preferred Cl, $X^-$ denotes any pharmaceutically acceptable counter anion, preferably selected from among acetate, halide, sulfate, hydrogen sulfate, succinate, malate, hydrogen carbonate, carbonate, sulfate×0.5 and carbonate×0.5, particularly preferred chloride and bromide.

$L^1$ denotes a group of formula (i),

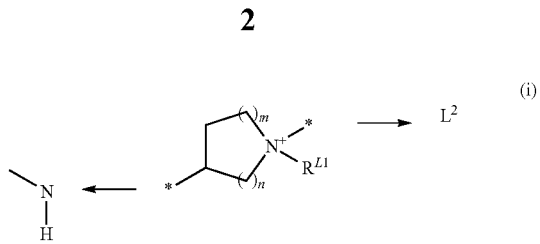

wherein $R^{L1}$ denotes $C_{1-6}$-alkyl or $R^{L1}$ denotes a $C_{1-6}$-alkylene bridge by replacing one of the hydrogen atoms of formula (i), forming a bicyclic ring system, n, m independently from each other denote 1, 2 or 3

$L^2$ denotes optionally substituted —$CH_2$—, $L^3$ denotes hydrogen or is selected from the group consisting of —COOH, —CO-phenyl, —COO—$C_{1-3}$-alkyl, $C_{6-10}$-aryl-$C_{1-3}$-alkyl-OOC—, —$C_{6-10}$-aryl-COO—$C_{1-4}$-alkyl, —C(O)NR²R³, optionally substituted $C_{6-10}$-aryl, optionally substituted heteroaryl, $C_{1-3}$-alkyl, $C_{2-5}$-alkenyl, $C_{2-3}$-alkynyl, $C_{3-7}$-cycloalkyl, $C_{5-7}$-cycloalkenyl, HO—$C_{1-7}$-alkyl-, $C_{1-4}$-alkoxy-$C_{1-5}$-alkyl-, $C_{1-4}$-alkyl-S(O)$_p$—$C_{1-3}$-alkyl-, C-linked heterocycle, —CO-heterocycle, —CO-heterocycle-heteroaryl, —CO-heterocycle-COO—$C_{1-4}$-alkyl, —CO-heterocycle-COOH and —CN, wherein, p is 0, 1 or 2

$R^2$, $R^3$ independently from each other are selected from among H, $C_{1-8}$-alkyl, optionally substituted, phenyl, $C_{6-10}$-aryl-$C_{5-6}$-cycloalkyl-, optionally substituted $C_{6-10}$aryl-$C_{1-4}$-alkyl-, HO—$C_{2-6}$-alkyl-, $C_{1-4}$-alkoxy-, $C_{1-4}$-alkoxy-$C_{2-6}$-alkyl-, optionally substituted heteroaryl, C-linked heterocycle, C-linked heterocyclyl-$C_{1-4}$-alkyl, C-linked heterocyclyl-COO—$C_{1-4}$-alkyl-, aryl-heterocyclyl-$C_{1-4}$-alkyl, N-linked heterocyclyl-$C_{2-4}$-alkyl, $C_{6-10}$-aryl-(HOOC)$C_{1-4}$-alkyl-, —CH($C_{1-3}$-alkyl-$C_{6-10}$-aryl)(COO—$C_{1-4}$-alkyl), —CH($C_{1-3}$-alkyl-$C_{6-10}$-aryl)(COOH), —$C_{1-3}$-alkyl-$C_{6-10}$-aryl-COO—$C_{1-4}$-alkyl, —$C_{6-10}$-aryl-COO—$C_{1-4}$-alkyl and —C($R^{3.1}R^{3.2}$)phenyl, wherein $R^{3.1}R^{3.2}$ together with the carbon atom they are attached to form an optionally substituted 5-7-membered heterocycle, or $R^2$ and $R^3$ together with the nitrogen atom they are attached to form an optionally substituted 5-7-membered heterocycle, and tautomers and optionally the pharmacologically acceptable acid addition salts thereof.

Preferred compounds of formula (I) are those wherein $L^3$ denotes optionally substituted phenyl.

Particularly preferred are compounds of formula (I), wherein
$L^3$ denotes optionally substituted phenyl of formula (ii),

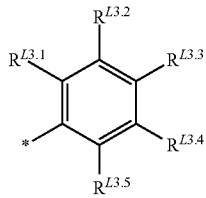

(ii)

$R^{L3.1}$, $R^{L3.2}$, $R^{L3.3}$, $R^{L3.4}$ independently from each other denote
hydrogen or are selected from the group consisting of —OH, —O—$C_{1-4}$-alkyl, $C_{1-4}$-alkyl, —S—$C_{1-4}$-alkyl, —S—$CF_3$, —$CF_3$, —O—CH2-phenyl, —O—$CF_3$, —$CH_2$—OH, —$CH_2$COOH, halogen, —$SO_2$—$C_{1-4}$-alkyl, $CH_3$, —COO—$C_{1-4}$-alkyl, —$CONH_2$, —$C_{1-4}$-alkyl-phenyl-CN, —CONH$C_{1-4}$-alkyl, —CON($C_{1-4}$-alkyl)$_2$, —CO—NH— heterocyclyl, —$CH_3$ and CN.

Also particularly preferred are compounds of formula (I), wherein
$L^1$ denotes a group of formula (i.1), (i.2) or (i.3)

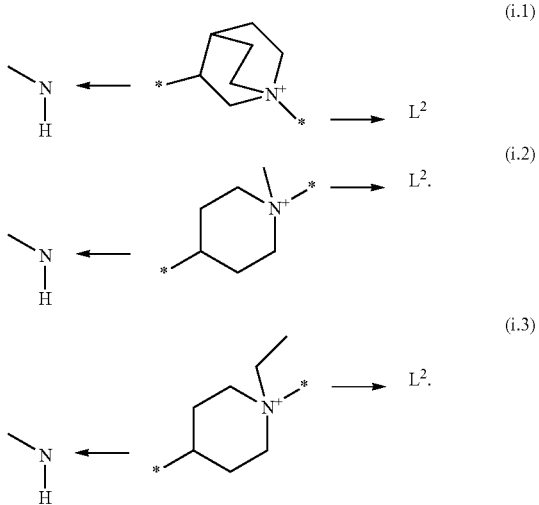

Also particularly preferred are compounds of formula (I), wherein
$L^2$ denotes —$CH_2$— or —CH(C(O)NHR$^{L2}$)—,
$R^{L2}$ is selected from a group consisting of H, $C_{1-8}$-alkyl, optionally substituted, phenyl, $C_{6-10}$-aryl-$C_{5-6}$-cycloalkyl-, optionally substituted $C_{6-10}$-aryl-$C_{1-4}$-alkyl-, HO—$C_{2-6}$-alkyl-, $C_{1-4}$-alkoxy-, $C_{1-4}$-alkoxy-$C_{2-6}$-alkyl-, optionally substituted heteroaryl, C-linked heterocycle, C-linked heterocyclyl-$C_{1-4}$-alkyl, C-linked heterocyclyl-COO—$C_{1-4}$-alkyl-, aryl-heterocyclyl-$C_{1-4}$-alkyl, N-linked heterocyclyl-$C_{2-4}$-alkyl, $C_{6-10}$-aryl-(HOOC)$C_{1-4}$-alkyl-, —CH($C_{1-3}$-alkyl-$C_{6-10}$-aryl)(COO—$C_{1-4}$-alkyl), —CH($C_{1-3}$-alkyl-$C_{6-10}$-aryl)(COOH), —$C_{1-3}$-alkyl-$C_{6-10}$-aryl-COO—$C_{1-4}$-alkyl, —$C_{6-10}$-aryl-COO—$C_{1-4}$-alkyl and —C($R^{3.1}R^{3.2}$)phenyl, wherein
$R^{3.1}R^{3.2}$ together with the carbon atom they are attached to form an optionally substituted 5-7-membered heterocycle.

A further embodiment of the current invention is a compound of formula (II)

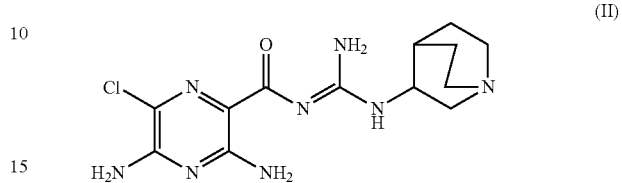

(II)

A further embodiment of the current invention is compounds of formula (I), or a pharmaceutically acceptable salt thereof as a medicament.

A further embodiment of the current invention is compounds of formula (I), or a pharmaceutically acceptable salt thereof for the treatment of a disease selected from among respiratory diseases or complaints and allergic diseases of the airways.

Preferred are compounds of formula (I) or a pharmaceutically acceptable salt thereof for the treatment of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema and pneumonitis of different origins, preferably chronic bronchitis, acute bronchitis, bronchitis, chronic obstructive bronchitis (COPD), asthma (intrinsic or allergic), cystic fibrosis and pediatric asthma, preferably chronic bronchitis, bronchiectasis, bronchitis, asthma, COPD and cystic fibrosis, particularly preferred COPD and cystic fibrosis.

A further embodiment of the current invention is a pharmaceutical composition comprising at least one compound as defined herein or a pharmaceutically acceptable salt thereof and a pharmaceutically acceptable carrier.

A further embodiment of the current invention is Medicament combinations which contain, besides one or more compounds as defined herein, as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators or double or triple combinations thereof.

4. Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the last named sub-group is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

When a compound of the present invention is depicted in the form of a chemical name and as a formula in case of any discrepancy the formula shall prevail. An asterisk may be used in sub-formulas to indicate the bond which is connected to the core molecule as defined.

For example, the term "3-carboxypropyl-group" represents the following substituent:

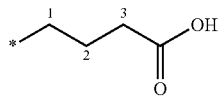

wherein the carboxy group is attached to the third carbon atom of the propyl group. The terms "1-methylpropyl-", "2,2-dimethylpropyl-" or "cyclopropylmethyl-" group represent the following groups:

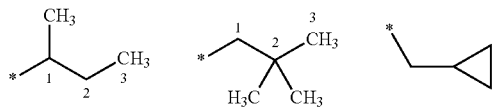

The asterisk "*" may be used in sub-formulas to indicate the bond which is connected to the core molecule as defined.

Many of the following terms may be used repeatedly in the definition of a formula or group and in each case have one of the meanings given above, independently of one another.

Unless specifically indicated, according to the invention a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substituted" as used herein, means that any one or more hydrogens on the designated atom is replaced with a selection from the indicated group, provided that the designated atom's normal valence is not exceeded, and that the substitution results in a stable compound.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds. For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof, or, regarding a permanent charge present in molecules according to the invention, the introduction of an appropriate counterion. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2''-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (–)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (–)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

As used herein, "pharmaceutically acceptable counter ion" refers to counter ions building the pharmaceutically acceptable salts described above. For example, where no basic residue such as an amine is present but a quaternary ammonium compound is present, such pharmaceutically acceptable counter ions may be part of the resulting salt. Further examples are hydrogen carbonate, carbonate and carbonate× 0.5. As the skilled person will appreciate, salts including potentially plurivalent ions may exist in different stoichiometric ratios, depending on whether the plurivalent ion is present in a singly or multiply charged form. For example, the charge state of a polyvalent acid will depend on the degree of its deprotonation.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocyclic ring" means a saturated or unsaturated mono- or polycyclic-ring system containing one or more heteroatoms selected from N, O or $S(O)_r$, wherein r=0, 1 or 2, consisting of 3 to 14 ring atoms. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

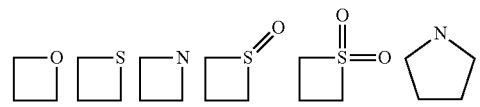

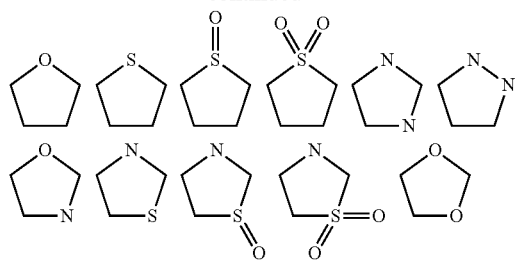
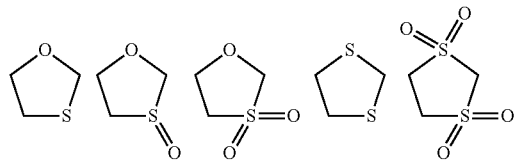
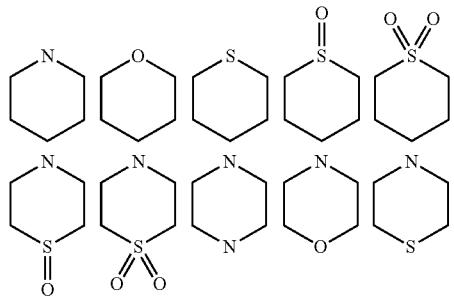
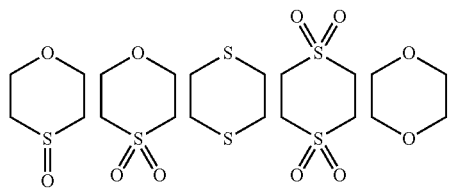
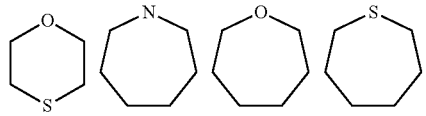
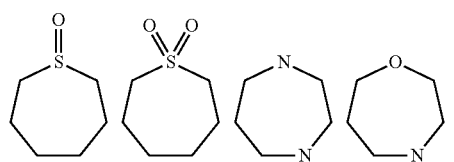
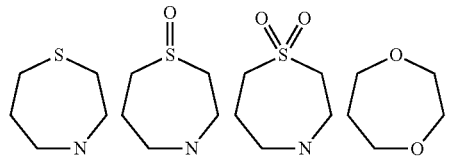
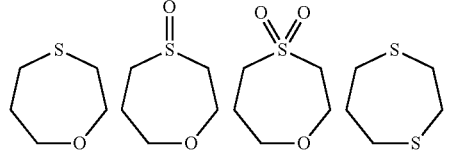
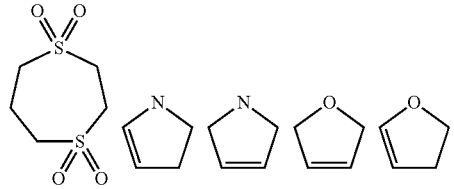
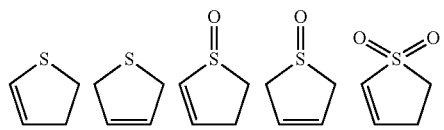
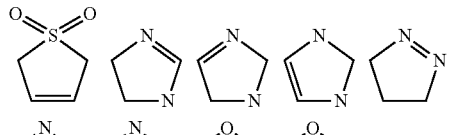
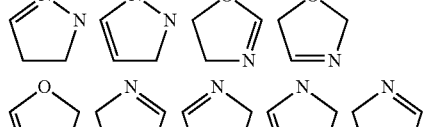
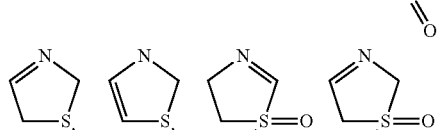
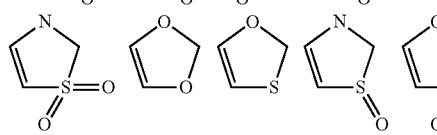
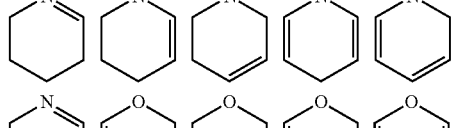
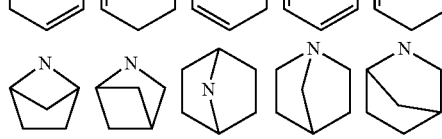
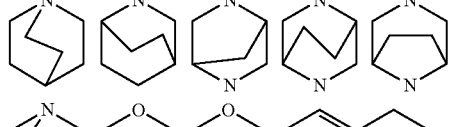
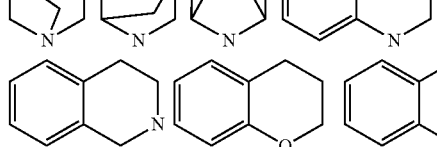
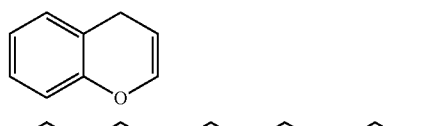
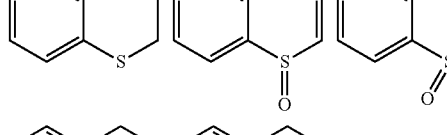
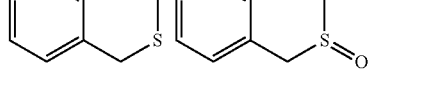

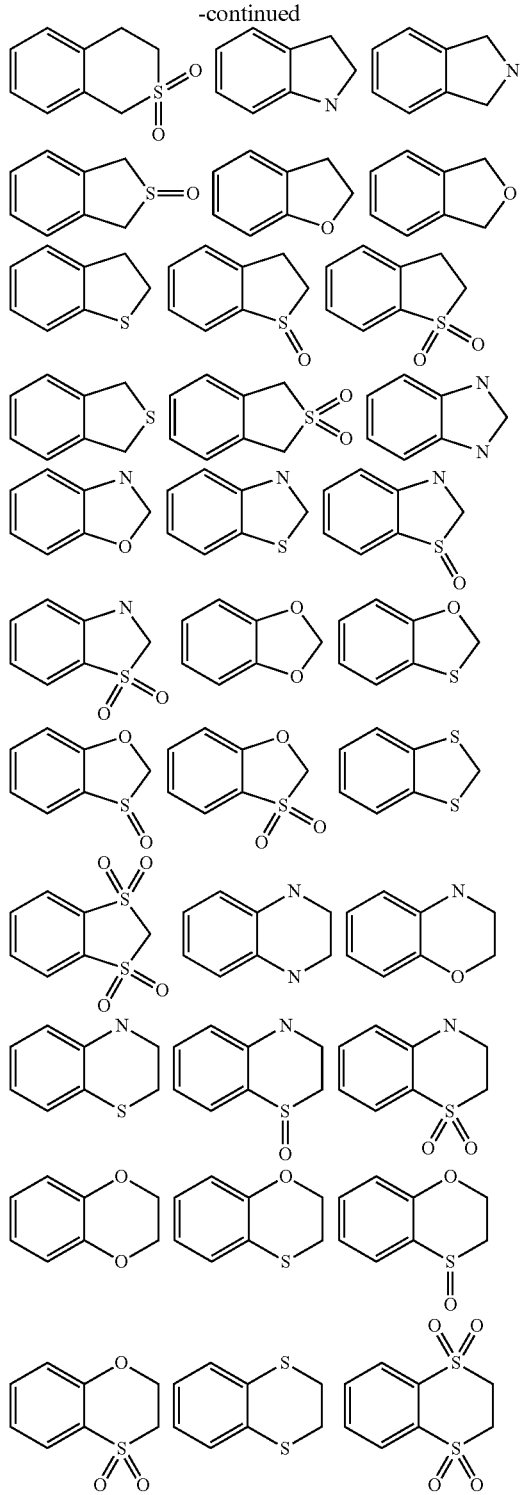

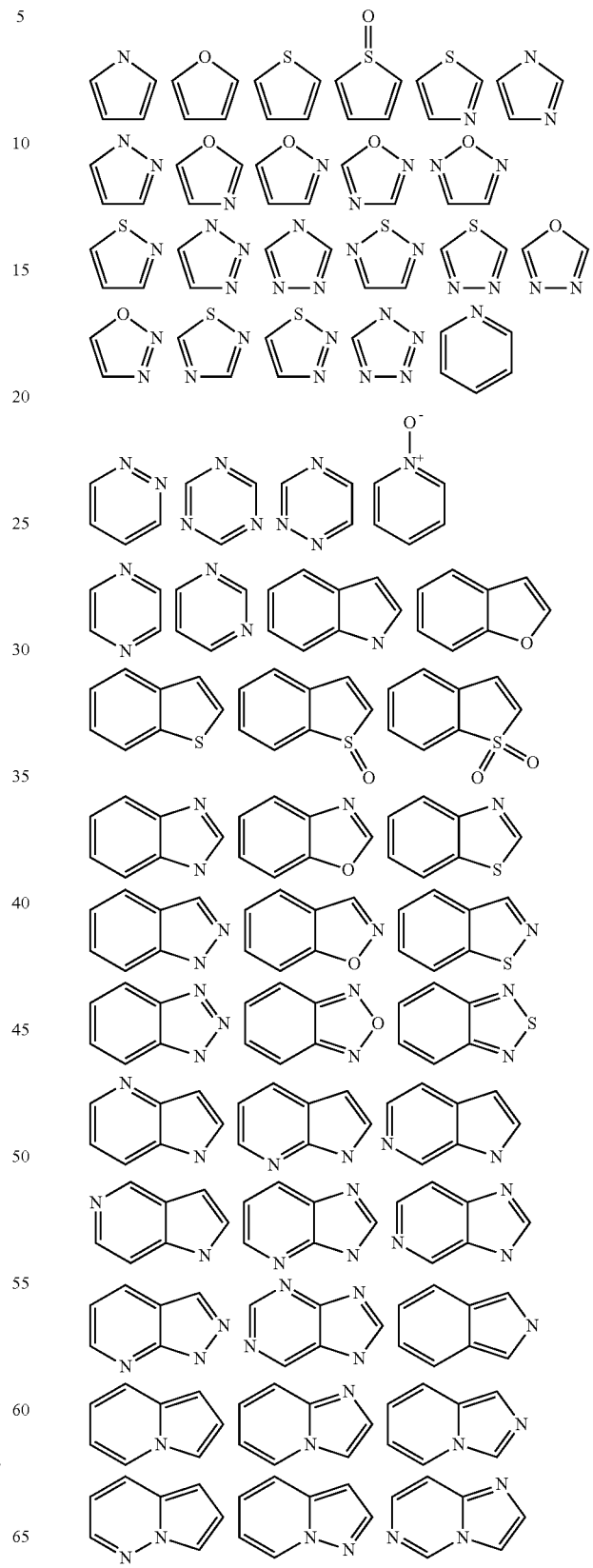

The term "heteroaryl" means a mono- or polycyclic-ring system containing one or more heteroatoms selected from N, O or S(O)$_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

-continued

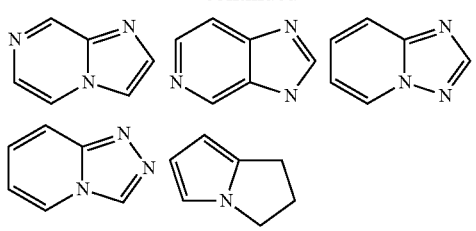

The term "monocyclic $C_{5-7}$-heterocyclyl" means a saturated or unsaturated non-aromatic monocyclic-ring system containing one or more heteroatoms selected from N, O or $S(O)_r$, wherein r=0, 1 or 2, consisting of 5 to 7 ring atoms. The term "monocyclic $C_{5-7}$-heterocyclyl" is intended to include all the possible isomeric forms.

Thus, the term "monocyclic $C_{5-7}$-heterocyclyl" includes the following exemplary structures which are not depicted as radicals as each form may be attached through a covalent bond to any atom so long as appropriate valences are maintained:

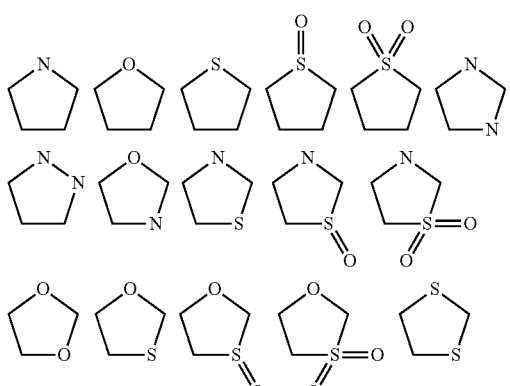

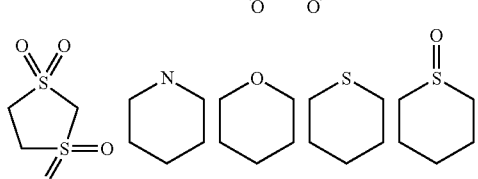

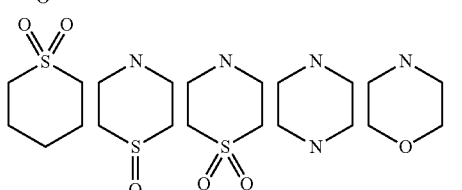

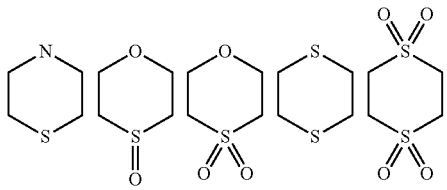

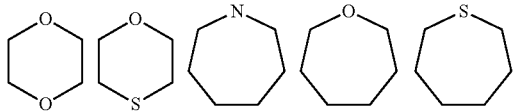

-continued

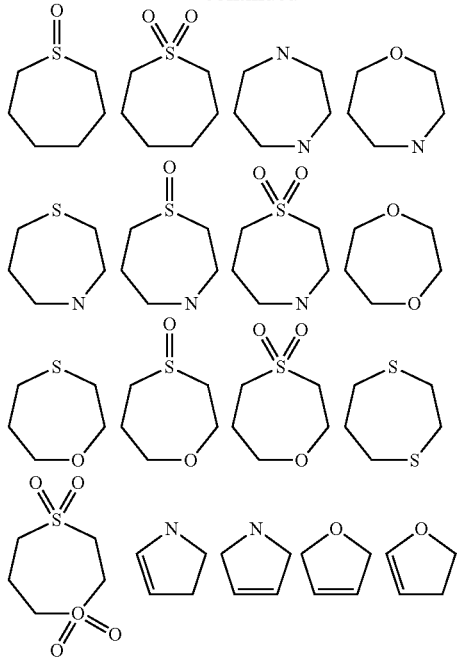

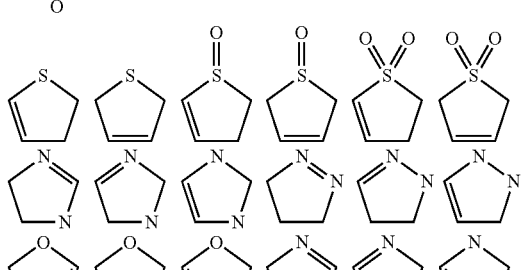

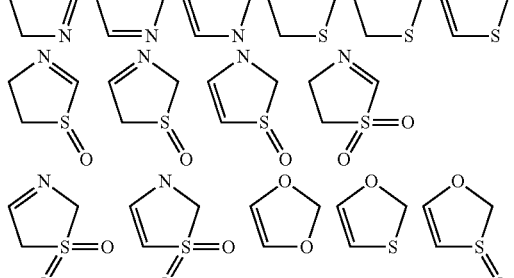

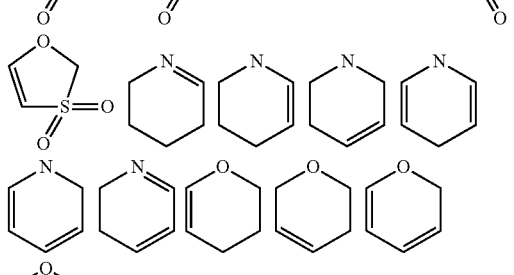

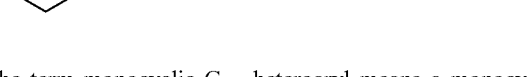

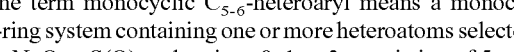

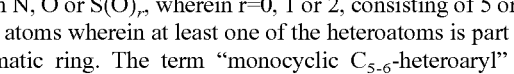

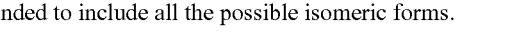

The term monocyclic $C_{5-6}$-heteroaryl means a monocyclic-ring system containing one or more heteroatoms selected from N, O or $S(O)_r$, wherein r=0, 1 or 2, consisting of 5 or 6 ring atoms wherein at least one of the heteroatoms is part of aromatic ring. The term "monocyclic $C_{5-6}$-heteroaryl" is intended to include all the possible isomeric forms.

Thus, the term "monocyclic $C_{5-6}$-heteroaryl" includes the following exemplary structures which are not depicted as radicals as each form may be attached through a covalent bond to any atom so long as appropriate valences are maintained:

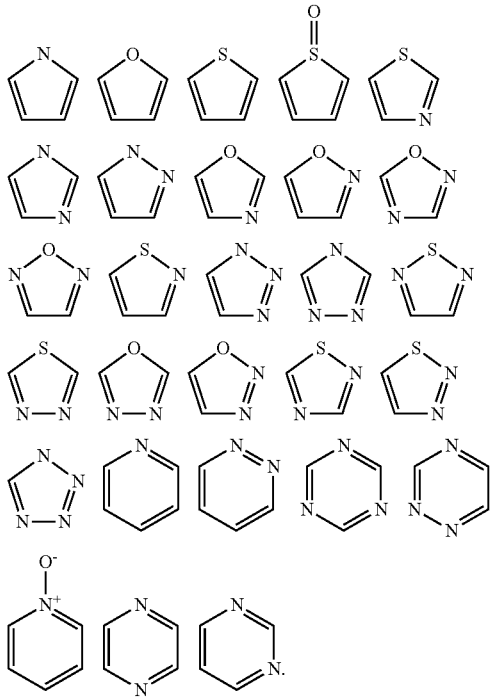

The term "bicyclic $C_{8-10}$-heterocyclyl" means a saturated or unsaturated bicyclic-ring system including aromatic ring systems containing one or more heteroatoms selected from N, O or $S(O)_r$, wherein r=0, 1 or 2, consisting of 8 to 10 ring atoms wherein the heteroatoms is optionally part of the aromatic ring. The term "bicyclic $C_{8-10}$-heterocyclyl" is intended to include all the possible isomeric forms.

Thus, the term "bicyclic $C_{8-10}$-heterocyclyl" includes the following exemplary structures which are not depicted as radicals as each form may be attached through a covalent bond to any atom so long as appropriate valences are maintained:

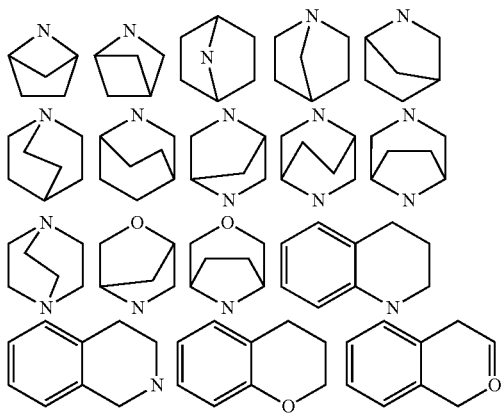

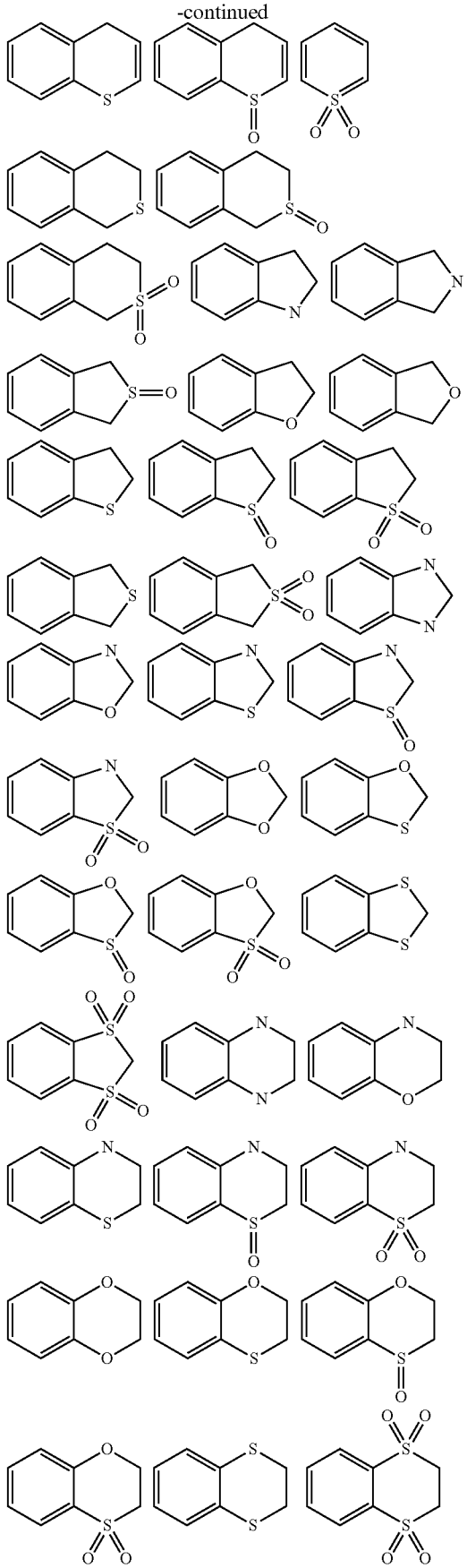

-continued

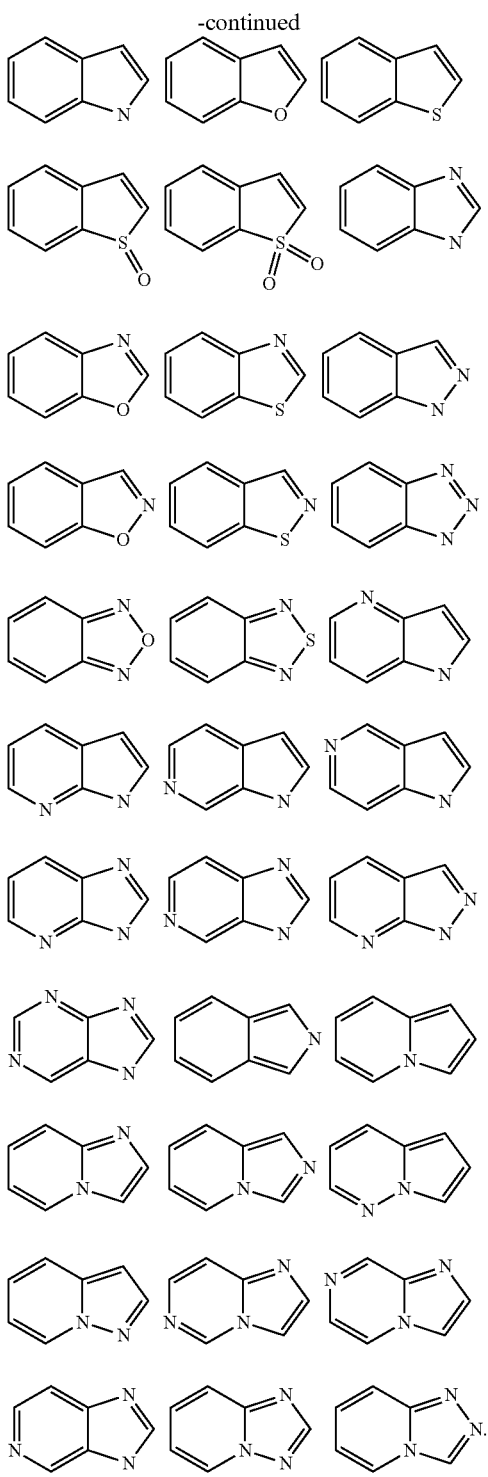

The term "annelated species of aryl or heterocyclyl" as used herein, either alone or in combination with another substituent wherein the annelated species presents as an aryl-het (a), a hetaryl (b) or a het-het (c) annelation means a monovalent substituent derived by removal of one hydrogen from an aromatic monocyclic system or aromatic multicyclic systems containing carbon atoms, which is annelated to a five-, six- or seven-membered saturated or unsaturated (including aromatic) heterocycle containing carbon atoms and one, two, three or four ring heteroatoms selected from nitrogen, oxygen and sulfur or a five-, six-, or seven-membered saturated or unsaturated (including aromatic) heterocycle containing carbon atoms and one, two, three or four ring heteroatoms selected from nitrogen, oxygen and sulfur, which is annelated to an aromatic monocyclic system or aromatic multicyclic systems containing carbon atoms or a five-, six-, or seven-membered saturated or unsaturated (including aromatic) heterocycle containing carbon atoms and one, two, three or four ring heteroatoms selected from nitrogen, oxygen and sulfur, which is annelated to a five-, six-, or seven-membered saturated or unsaturated (including aromatic) heterocycle containing carbon atoms and one, two, three or four ring heteroatoms selected from nitrogen, oxygen and sulfur.

Suitable examples of an annelated species of aryl or het include: quinolinyl, 1-indoyl, 3-indoyl, 5-indoyl, 6-indoyl, indolizinyl, benzimidazyl or purinyl.

The term "halogen" as used herein means a halogen substituent selected from fluoro, chloro, bromo or iodo.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes $-CH_2-$, $-CH_2-CH_2-$, $-CH(CH_3)-$, $-CH_2-CH_2-CH_2-$, $-C(CH_3)_2-$, $-CH(CH_2CH_3)-$, $-CH(CH_3)-CH_2-$, $-CH_2-CH(CH_3)-$, $-CH_2-CH_2-CH_2-CH_2-$, $-CH_2-CH_2-CH(CH_3)-$, $-CH(CH_3)-CH_2-CH_2-$, $-CH_2-CH(CH_3)-CH_2-$, $-CH_2-C(CH_3)_2-$, $-C(CH_3)_2-CH_2-$, $-CH(CH_3)-CH(CH_3)-$, $-CH_2-CH(CH_2CH_3)-$, $-CH(CH_2CH_3)-CH_2-$, $-CH(CH_2CH_2CH_3)-$, $-CH(CH(CH_3))_2-$ and $-C(CH_3)(CH_2CH_3)-$.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "$C_{2-n}$-alkenylene" is used for a group as defined in the definition for "$C_{1-n}$-alkylene" with at least two carbon atoms, if at least two of those carbon atoms of said group are bonded to each other by a double bond.

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

The term "$C_{2-n}$-alkynylene" is used for a group as defined in the definition for "$C_{1-n}$-alkylene" with at least two carbon atoms, if at least two of those carbon atoms of said group are bonded to each other by a triple bond.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "$C_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

In all cases of contradictions between structure and their naming structure shall prevail.

5. Preferred Embodiments

The substituent $R^1$ denotes halogen, preferably Cl or Br, particularly preferred Cl.

The counteranion X is selected from among acetate, halide, sulfate, hydrogen sulfate, succinate, malate, hydrogen carbonate, carbonate, sulfate×0.5 and carbonate×0.5, particularly preferred chloride and bromide.

The substituent $L^1$ denotes a group of formula (i),

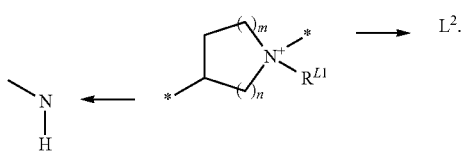

(i)

The substituent $R^{L1}$ denotes $C_{1-6}$-alkyl, preferably methyl or ethyl, particularly preferred methyl, or the substituent $R^{L1}$ denotes a $C_{1-6}$-alkylene bridge, preferably $C_2$-alkylene bridge, by replacing one of the hydrogen atoms of formula (i), forming a bicyclic ring system.

Preferably substituent $R^{L1}$ denotes methyl or ethyl. Variables n, m independently from each other denote 1, 2 or 3, preferably n denotes 1 and m denotes 1 or 2, particularly preferred 2.

Particularly preferred $L^1$ denotes a group of formula (i.1), (i.2) or (i.3),

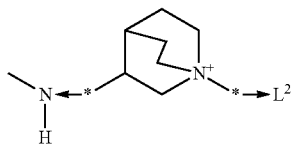

(i.1)

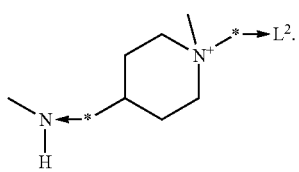

(i.2)

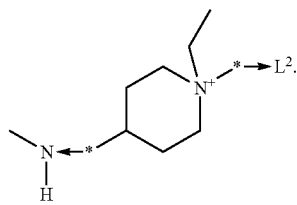

(i.3)

Most preferred $L^1$ denotes a group of formula (i.1.1)

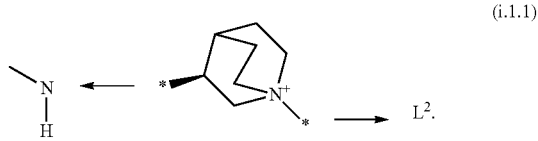

(i.1.1)

The substituent $L^2$ denotes optionally substituted —$CH_2$—, preferably —$CH_2$— or —CH—C(O)NHR$^{L2}$, more preferably —$CH_2$—.

Particularly preferred substituent $L^2$ denotes —$CH_2$- or $C_{1-8}$-alkyl.

The substituent $R^{L2}$ denotes hydrogen or is selected from the group consisting of $C_{1-8}$-alkyl, optionally substituted, phenyl, $C_{6-10}$-aryl-$C_{5-6}$-cycloalkyl-, optionally substituted $C_{6-10}$ aryl-$C_{1-4}$-alkyl-, HO—$C_{2-6}$-alkyl-, $C_{1-4}$-alkoxy-, $C_{1-4}$-alkoxy-$C_{2-6}$-alkyl-, optionally substituted heteroaryl, C-linked heterocycle, C-linked heterocyclyl-$C_{1-4}$-alkyl, C-linked heterocyclyl-COO—$C_{1-4}$-alkyl-, aryl-heterocyclyl-$C_{1-4}$-alkyl, N-linked heterocyclyl-$C_{2-4}$-alkyl, $C_{6-10}$-aryl-(HOOC)$C_{1-4}$-alkyl-, —CH($C_{1-3}$-alkyl-$C_{6-10}$-aryl)(COO—$C_{1-4}$-alkyl), —CH($C_{1-3}$-alkyl-$C_{6-10}$-aryl)(COOH), —$C_{1-3}$-alkyl-$C_{6-10}$-aryl-COO—$C_{1-4}$-alkyl, —$C_{6-10}$-aryl-COO—$C_{1-4}$-alkyl and —C($R^{3.1}R^{3.2}$)phenyl, wherein $R^{3.1}R^{3.2}$ together with the carbon atom they are attached to form an optionally substituted 5-7-membered heterocycle.

Preferably $R^{L2}$ denotes hydrogen or is selected from the group consisting of $C_{1-8}$-alkyl, $C_{6-10}$-aryl-$C_{1-4}$-alkyl-, HO—$C_{2-6}$-alkyl-, $C_{1-4}$-alkoxy-$C_{2-6}$-alkyl-, optionally substituted heteroaryl, C-linked heterocycle, C-linked heterocyclyl-$C_{1-4}$-alkyl, aryl-heterocyclyl-$C_{1-4}$-alkyl-, N-linked heterocyclyl-$C_{2-4}$-alkyl-, $C_{6-10}$-aryl-(HOOC)$C_{1-4}$-alkyl- and $C_{6-10}$-aryl-($C_{1-4}$-alkyl-OOC)$C_{1-4}$-alkyl.

The substituent $L^3$ denotes hydrogen or is selected from the group consisting of —COOH, —CO-phenyl, —COO—$C_{1-3}$-alkyl, $C_{6-10}$-aryl-$C_{1-3}$-alkyl-OOC—, —$C_{6-10}$-aryl-COO—$C_{1-3}$-alkyl, —C(O)NR$^2$R$^3$, optionally substituted $C_{6-10}$-aryl, preferably phenyl, 4-trifluoromethylsulfanyl-phenyl, 3-methylsulfanyl-phenyl, 4-methylsulfanyl-phenyl, 3,4,5-trimethoxyphenyl, 2,3-dimethoxyphenyl, 3-methoxyphenyl, 2-trifluoromethoxyphenyl, 4-hydroxymethylphenyl, 3,5-difluorophenyl, optionally substituted heteroaryl, preferably optionally substituted quinolinyl, pyridinyl, benzothiazolyl, thiazolyl, thiadiazolyl-thiophenyl, $C_{1-3}$-alkyl, $C_{2-5}$-alkenyl and $C_{2-3}$-alkynyl, $C_{3-7}$-cycloalkyl, preferably cyclohexyl, $C_{5-7}$-cycloalkenyl, HO—$C_{1-7}$-alkyl-, $C_{1-4}$-alkoxy-$C_{1-5}$-alkyl-, $C_{1-4}$-alkyl-S(O)$_p$—$C_{1-3}$-alkyl-, C-linked heterocycle, —CO-heterocycle, preferably —CO-pyranyl, —CO-heterocycle-heteroaryl, —CO-heterocycle-COO—$C_{1-4}$-alkyl, —CO-heterocycle-COOH and —CN.

Particularly preferred substituent $L^3$ denotes hydrogen or is selected from the group consisting of optionally substituted phenyl, 4-trifluoromethylsulfanylphenyl, 3,4,5-trimethoxyphenyl, 2,3-dimethoxyphenyl, 4-hydroxymethylphenyl, and —C(O)NR²R³, particularly preferred phenyl, 4-trifluoromethylsulfanylphenyl and —C(O)NR²R³.

Variable p is 0, 1 or 2, preferably 2.

Substituents $R^2$, $R^3$ independently from each other denote hydrogen or are selected from the group consisting of $C_{1-8}$-alkyl, preferably $C_{1-2}$-alkyl, particularly preferred ethyl, phenyl, $C_{6-10}$-aryl-$C_{5-6}$-cycloalkyl-, $C_{6-10}$-aryl-$C_{1-4}$-alkyl-, preferably Cl—$C_{6-10}$-aryl-$C_{1-4}$-alkyl- or CN—$C_{6-10}$-aryl-$C_{1-4}$-alkyl-, $CH_3OOC$—$C_{6-10}$-aryl-$C_{1-4}$-alkyl-, HOOC—$C_{6-10}$-aryl-$C_{1-4}$-alkyl-, particularly preferred 4-chlorobenzyl, phenethyl, HO—$C_{2-6}$-alkyl-, $C_{1-4}$-alkoxy-, $C_{1-4}$-alkoxy-$C_{2-6}$-alkyl-, optionally substituted heteroaryl, C-linked heterocycle, C-linked heterocyclyl-$C_{1-4}$-alkyl-, preferably tetrahydropyran-4-yl)-methyl, C-linked heterocyclyl-COO—$C_{1-4}$-alkyl-, aryl-heterocyclyl-$C_{1-4}$-alkyl-, N-linked heterocyclyl-$C_{2-4}$-alkyl, $C_{6-10}$-aryl-(HOOC)$C_{1-4}$-alkyl-, preferably phenyl-(HOOC)$C_{1-4}$-alkyl-, particularly preferred 1-carboxy-2-phenyl-ethyl, and —CH($C_{1-3}$-alkyl-$C_{6-10}$-aryl)(COO—$C_{1-4}$-alkyl) preferably —CH($C_{1-3}$-alkyl-phenyl)(COO—$C_{1-4}$-alkyl), particularly preferred 1-tert-butoxycarbonyl-2-phenyl-ethyl, —CH($C_{1-3}$-alkyl-$C_{6-10}$-aryl)(COOH), —$C_{1-3}$-alkyl-$C_{6-10}$-aryl-COO—$C_{1-4}$-alkyl, —$C_{6-10}$-aryl-COO—$C_{1-4}$-alkyl and —$CH_2C(R^{3.1}R^{3.2})$phenyl, wherein $R^{3.1}R^{3.2}$ together with the carbon atom they are attached to form an optionally substituted 5-7-membered heterocycle, preferably pyranyl, or $R^2$ and $R^3$ together with the nitrogen atom they are attached to form an optionally substituted 5-7-membered heterocycle, particularly preferred a morpholine, piperazine or piperidine preferably unsubstituted or substituted by a carboxylic acid or heteroaryl, particularly preferred substituted by a pyridine or pyrimidine.

Preferably the substituents $R^2$, $R^3$ independently from each other denote hydrogen, ethyl, 4-chlorobenzyl, phenethyl, 1-carboxy-2-phenyl-ethyl, 1-tert-butoxycarbonyl-2-phenyl-ethyl or $R^2$ and $R^3$ together with the nitrogen atom they are attached to denote 2-piperazin-1-yl-pyrimidine or 2-pyridin-1-yl-pyrimidine.

The substituents $R^{L3.1}$, $R^{L3.2}$, $R^{L3.3}$, $R^{L3.4}$ independently from each other denote hydrogen or are selected from the group consisting of —OH, —O—$C_{1-4}$-alkyl, $C_{1-4}$-alkyl, —S—$C_{1-4}$-alkyl, —S—$CF_3$, —$CF_3$, —O—$CH_2$-phenyl, —O—$CF_3$, —$CH_2$—OH, —$CH_2COOH$, halogen, —$SO_2$—$C_{1-4}$-alkyl, —COO—$C_{1-4}$-alkyl, —$CONH_2$, —$C_{1-4}$-alkyl-phenyl-CN, —$CONHC_{1-4}$-alkyl, —$CON(C_{1-4}$-alkyl)$_2$ and —CO—NH-heterocyclyl, preferably —CO—NH—, —CN.

Preferably the substituents $R^{L3.1}$, $R^{L3.2}$, $R^{L3.3}$, $R^{L3.4}$ independently from each other denote H, —S—$CF_3$, —OMe, —$OCF_3$, —$CH_2OH$, —SMe or F Any and each other of the definitions of $R^1$ to $R^3$, $R^{L1}$, $R^{L2}$, $R^{L3.1}$, $R^{L3.2}$, $R^{L3.3}$, $R^{L3.4}$, X, m, n, $L^1$, $L^2$ and $L^3$ may be combined with each other.

6. Preparation

The following methods are suitable for preparing compounds of general formula (I), The compounds according to the invention may be obtained using methods of synthesis known in principle. It is noted to those skilled in the art that the presence of certain functional groups in the reaction partners may interfere with the intended reaction. Where this applies suitable protecting groups as described e.g. in "*Protective Groups in Organic Synthesis*", $2^{nd}$ edition, Greene T. W., Wuts P. G. M.; Wiley-Interscience: New York, 1991 or in "*Protective Groups*", Kocienski P. J.; Thieme: New York, 1994 can be used. Preferably the compounds according to the invention are obtained by the following methods which are described in more detail hereinafter, in particular as described in the experimental section.

Compounds of general formula (I) can be prepared by reaction of tertiary amines of formula IIa or IIb with alkylating agents of formula IIIa or IIIb, respectively. Alternatively, a secondary amine of formula IIc is allowed to react with a bivalent alkylating agent of formula IIIc. LG (and LG' where applicable) is a suitable leaving group such as Cl, Br, I, or a sulfonate ester, for example $OS(O)_2Me$. The reaction may be carried out in a solvent like acetonitrile or DMF or in a solvent mixture, typically at r.t. or with heating. A base, especially when the amine II is applied as an acid addition salt, may be added. LG (and LG' where applicable) may directly furnish the anion $X^-$ of compounds of formula I, as defined hereinbefore, or one anionic species may be changed to another suitable anionic species by methods known to those skilled in the art.

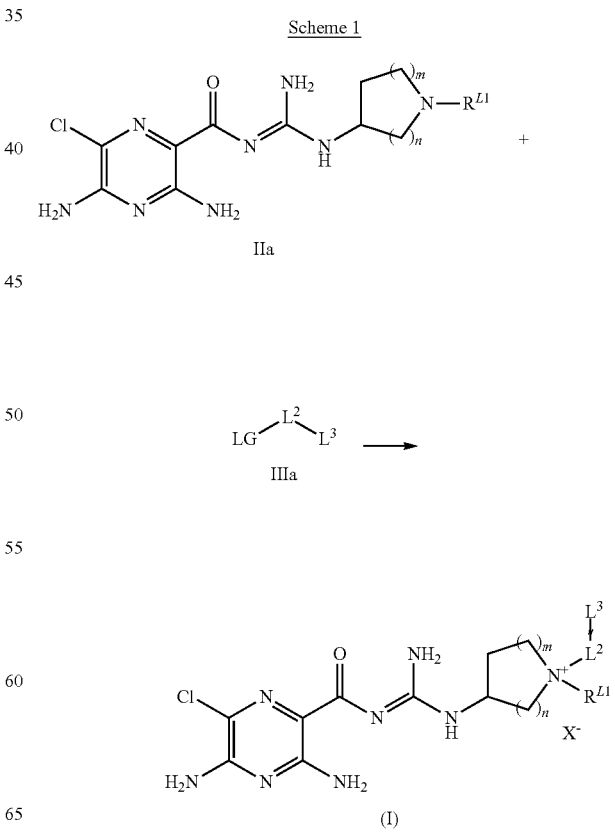

Scheme 1

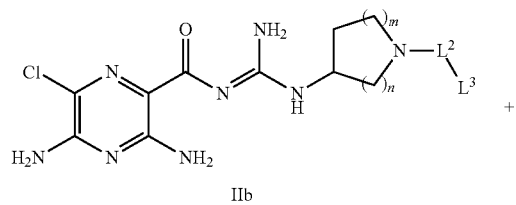

IIb

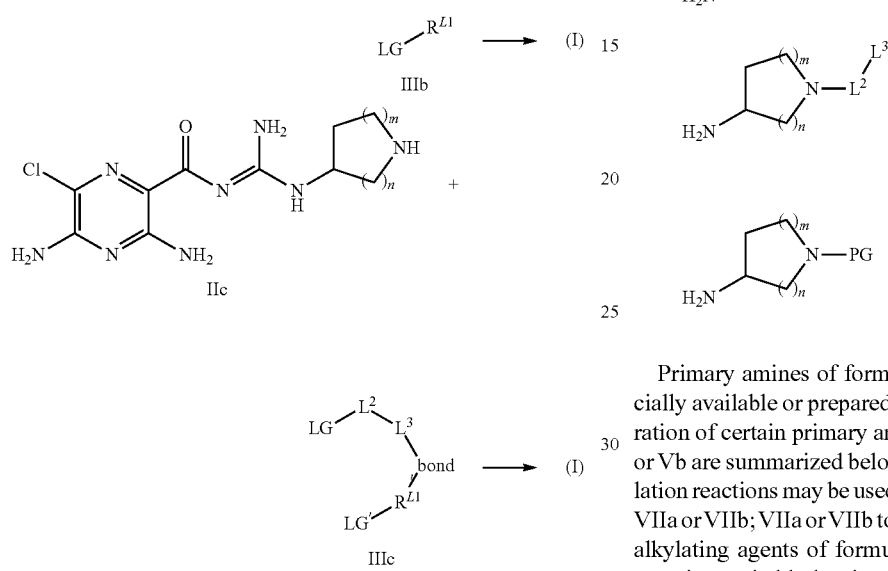

A further way of preparing compounds of general formula (I) is by reacting S-methylisothiourea of formula IV with primary amines of formula V, where Y⁻ indicates a suitable anion, in a solvent like THF, acetonitrile or DMF or in a solvent mixture, preferably in the presence of a base, especially when the primary amine III is applied as an acid addition salt, preferably at r.t. or with heating up to the boiling point.

Scheme 2

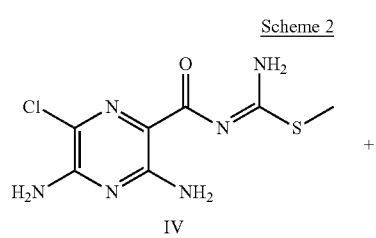

IV

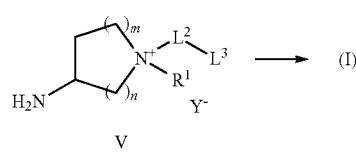

V

In analogy to the above description compounds of formulas IIa, IIb and IIc may be prepared by reaction between S-methylisothiourea of formula IV and the primary amines of formula Va, Vb or Vc, respectively (whereby the latter requires subsequent deprotection of the suitable protecting group PG).

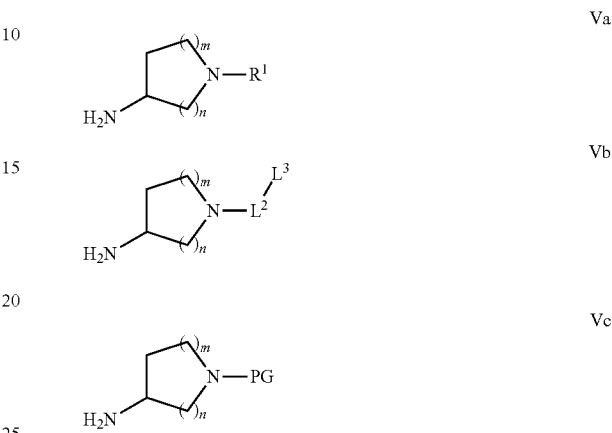

Primary amines of formula V, Va or Vb may be commercially available or prepared. Processes suitable for the preparation of certain primary amine containing compounds V, Va or Vb are summarized below. Thus, amine nucleophilic alkylation reactions may be used to convert certain structures VI to VIIa or VIIb; VIIa or VIIb to VIII; or VI to VIII. The respective alkylating agents of formula IIIa, IIIb, or IIIc, respectively contain a suitable leaving group LG (and LG' where applicable) such as Cl, Br, I, or a sulfonate ester, for example $OS(O)_2Me$. Suitable reaction conditions are known to those skilled in the art to be those appropriate for alkylations following nucleophilic substitution mechanisms. As an example, the reaction may be carried out in a solvent like acetonitrile or DMF or in a solvent mixture, typically at r.t. or with heating. A base, especially when the amine II is applied as an acid addition salt, may be added. LG (and LG' where applicable) may directly furnish the anions Y— of compounds of formula VIII, or one anionic species may be changed to another suitable anionic species by methods known to those skilled in the art. Alternatively the conversions of certain structures VI to VIIa or VIIb may be effected under conditions of reductive amination, using carbonyl derivatives which on reduction reveal the respective groups $R^1$ or $CR^2R^3R^4$. Suitable reaction conditions for reductive amination reactions are known to those skilled in the art and may involve for example sodium triacetoxyborohydride, sodium cyanoborohydride or hydrogen in the presence of a suitable catalyst such as palladium on charcoal. Suitable examples of protecting groups PG for the primary amine may be tert-butyloxycarbonyl and benzyloxycarbonyl groups. Suitable amines, alkylating agents or carbonyl derivatives used in the processes described above may be commercially available or derived from commercially available precursors by functional group interconversions known to the skilled person and listed e.g. in "Comprehensive Organic Transformations, A Guide to Functional Group Preparations", $2^{nd}$ edition, Larock, R. C.; Wiley-VCH: New York, 1999.

Scheme 3

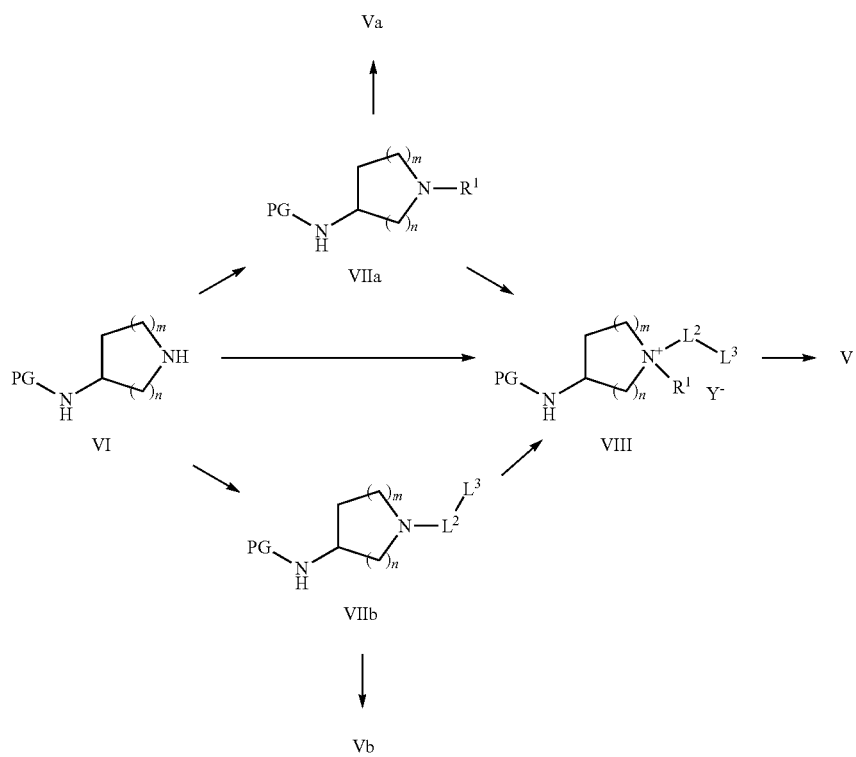

Y⁻ indicates a suitable anion

The compound of formula IV can be prepared by reacting S-methylisothiourea (which may be generated in situ from its sulphuric acid salt by addition of base) with a 1-(tert-butyl-carbamoyl)prop1-en-2-yl carboxylate of formula XI in a solvent like dichloromethane, tetrahydrofurane, water or a mixture of these solvents, preferably at r.t. The compound of formula XI can be prepared from the respective carboxylic acid of formula IX and a 2-tert-butyl-5-methyl-isoxazolium salt of general formula X, which can be applied as an isolated salt (e.g. the hexafluorophosphate salt; X=PF$_6$) or generated in situ from tert-butanol, 5-methylisoxazole and trifluoromethanesulphonic acid. The latter reaction is preferably performed in a solvent like DMF or in a solvent mixture with the addition of triethylamine or another base, preferably while cooling to 0-10° C.

Scheme 4

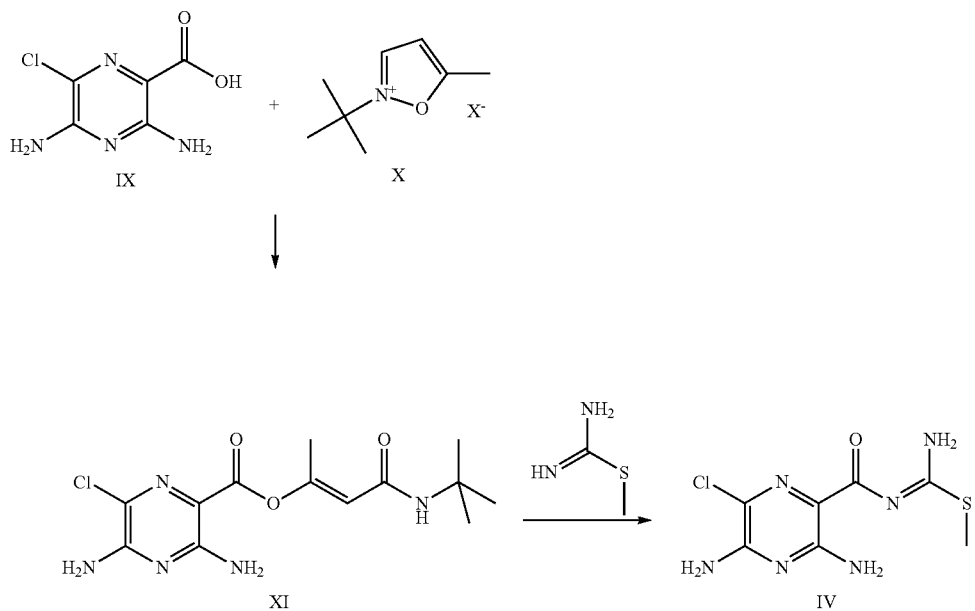

Compounds of formula I, as defined hereinbefore, are salts containing an anion X⁻. These anions X⁻ may be derived from synthesis or purification or changed from one anionic species to another suitable anionic species by methods known to those skilled in the art. Examples of such methods are ion exchange using for example ion exchange resins or displacement of an acid counterion from its salt using another, usually stronger, acid. For example, treatment of a compound of formula I, as defined hereinbefore, where X⁻ is CF3COO⁻, with HCl in a suitable solvent, such as water or diethyl ether, may produce a compound of formula I, as defined hereinbefore, where X⁻ is Cl⁻.

Certain compounds of formula I, as defined hereinbefore, may contain groups that may be further converted into the salts thereof, for pharmaceutical use particularly into pharmaceutically acceptable salts with inorganic or organic acids and bases. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid. Corresponding processes are known to the skilled person.

Moreover, where one or more stereoisomers may exist, the compounds of general formula (I) or intermediates in the synthesis of compounds of general formula may be obtained as mixtures and then resolved into their stereoisomers, e.g. enantiomers and/or diastereomers. Thus, for example, E-/Z-mixtures may be resolved into their E- and Z-isomers, and racemic compounds may be separated into their enantiomers.

Thus, for example, the E-/Z-mixtures may be resolved by chromatography into the E- and Z-isomers thereof. The compounds of general formula (I) or intermediates in the synthesis of compounds of general formula (I), which occur as racemates may be separated by methods known per se (cf. Allinger N. L. and Eliel E. L. in "Topics in Stereochemistry", Vol. 6, Wiley Interscience, 1971) into their optical antipodes and compounds of general formula (I) or intermediates in the synthesis of compounds of general formula (I) with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids in common use for such a purpose are e.g. the D- and L-forms of tartaric acid, dibenzoyltartaric acid, ditoloyltartaric acid, malic acid, mandelic acid, camphorsulfonic acid, glutamic acid, aspartic acid, or quinic acid. Optically active alcohols applicable as auxiliary residues may be, for example, (+)- or (−)-menthol and optically active acyl groups in amides may be, for example, (+)- or (−)-menthyloxycarbonyl.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

The compounds according to the invention are advantageously obtainable using the methods described in the examples that follow, which may also be combined for this purpose with methods known to the skilled person from his/her expert knowledge. Likewise, further compounds according to this invention, whose preparation are not explicitly described in the following examples, can be prepared analogously or similarly to the examples.

The Examples that follow are intended to illustrate the present invention without restricting it. In general where salt forms of compounds are specified they are deduced from the preparation conditions and have not been analytically verified. Further, stoichiometry of the counterion is usually omitted. The skilled person will appreciate that the compound is not limited to a certain salt form nor to the mono salt form and that it may exist as a disalt, trisalt or other compound:counterion stoichiometries. Furthermore, the skilled person will appreciate that such compound may unexpectedly exist as a salt with a different counterion or, where applicable, as an internal salt depending on the synthesis conditions and the processes of workup and purification applied.

7. EXAMPLES

Where no salt forms of compounds are specified, the compound may exist as a free base or a salt, depending on the synthesis conditions and the processes of workup and purification applied. The skilled person will appreciate that the compound is not limited to the free base or a certain salt form. Where salt forms of compounds are specified, the stoichiometry of the counterion is usually omitted. The skilled person will appreciate that the compound is not limited to the mono salt form and that it may exist as a disalt, trisalt or other compound:counterion stoichiometries. Furthermore, the skilled person will appreciate that such compound may unexpectedly exist as a free base or as a salt with a different counterion, depending on the synthesis conditions and the processes of workup and purification applied. Solely for the purpose of yield determination, an estimate of the nature of the counterion and of compound:counterion stoichiometry is made (as indicated by the formula given).

7.1 Synthesis of Intermediates

Intermediate 1

3,5-Diamino-6-chloropyrazine-2-carboxylic acid

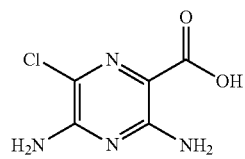

Intermediate 1

A mixture of methyl 3,5-diamino-6-chloropyrazine-2-carboxylate (100 g; 494 mmol), methanol (1 L) and NaOH (6 mol/L in water; 240 mL; 1.44 mol) is refluxed for 3 h. The mixture is allowed to cool to room temperature and then neutralised by addition of hydrochloric acid (6 M in water; ca. 120 mL). Water (200 mL) is added. The precipitate formed is collected by filtration while applying suction, washed with water and dried at 60° C. Yield: 99.6 g (107% of theory).

ESI Mass spectrum: m/z=189 [M+H]⁺; m/z=187 [M−H]⁻

Intermediate 1.1

3,5-Diamino-6-bromopyrazine-2-carboxylic acid is prepared from methyl 3,5-diamino-6-bromopyrazine-2-carboxylate (which is prepared from methyl 3,5-diamino-6-chloropyrazine-2-carboxylate as described in J. Med. Chem. 10 (1967) 66-75) analogously to the procedure described for the synthesis of intermediate 1

Intermediate 2

1-(tert-Butylcarbamoyl)prop-1-en-2-yl 3,5-diamino-6-chloropyrazine-2-carboxylate Intermediate 2

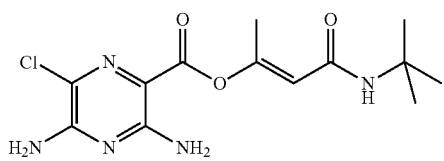

Stage 1:

A mixture of tert-butanol (21.0 mL; 226 mmol) and 5-methylisoxazole (18.0 mL; 221 mmol) is cooled in an ice-bath. Trifluoromethanesulphonic acid (20.0 mL; 221 mmol) is added dropwise with continued cooling. The resulting mixture is stirred for 1 h without further cooling.

Stage 2:

A solution of 3,5-diamino-6-chloropyrazine-2-carboxylic acid (Intermediate 1; 14.0 g; 74.2 mmol) in DMF (400 mL) is added to the mixture prepared in stage 1, then triethylamine (31.0 mL; 222 mmol) is added. The resulting mixture is stirred for 4 h at room temperature. Ice-water is added with stirring. The precipitate formed is collected by filtration while applying suction, washed with water and dried at 65° C. to yield the title compound (18.2 g, 75% of theory).

TLC (Silica; CH₂Cl₂:MeOH 9:1): R_f=0.4

ESI Mass spectrum: m/z=328 [M+H]⁺; m/z=326 [M−H]⁻

Intermediate 2.1

1-(2-Methyl-2-butyl-carbamoyl)prop-1-en-2-yl 3,5-diamino-6-bromopyrazine-2

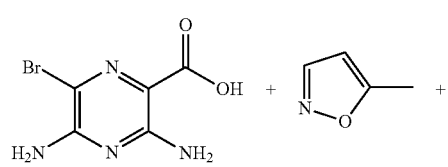

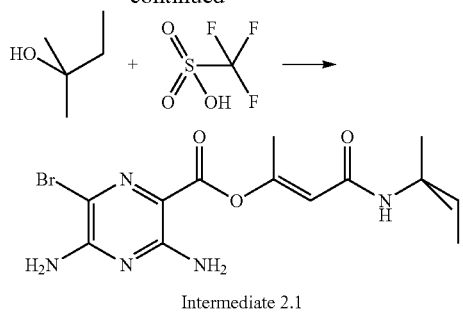

Intermediate 2.1

Stage 1:

A mixture of 2-methyl-2-butanol (5.75 mL; 51 mmol) and 5-methylisoxazole (4.42 mL; 51 mmol) is cooled with an ice-bath. Trifluoromethanesulphonic acid (4.84 mL; 54 mmol) is added dropwise with continued cooling. The resulting mixture is stirred overnight without further cooling.

Stage 2:

To a solution or suspension of 3,5-diamino-6-bromopyrazine-2-carboxylic acid (Intermediate 1.1; 5.00 g; 21.5 mmol) and triethylamine (7.48 mL; 54 mmol) in DMF (50 mL) cooled with an ice-bath is added dropwise the mixture prepared in stage 1. The resulting mixture is stirred for 4 h at r.t., then poured on ice-water. The precipitate formed is filtered off with suction, washed with water and dried at 50° C. to yield the title compound.

Yield: 7.53 g (91% of theory)

C₁₄H₂₀BrN₅O₃ ESI Mass spectrum: m/z=386 [M+H]+; m/z=384 [M−H]⁻

Intermediate 3

3,5-Diamino-6-chloro-N-[(methylsulfanyl)methanimidoyl]pyrazine-2-carboxamide

Intermediate 3

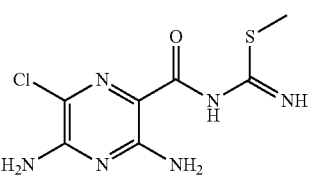

To NaOH (1 M in water; 18.7 mL; 18.7 mmol) is added S-methylisothiourea sulphate (4.25 g; 15.3 mmol). The mixture is stirred until complete dissolution is achieved. CH₂Cl₂: tetrahydrofuran (1:1; 30 mL) and then 1-(tert-butylcarbamoyl)prop-1-en-2-yl 3,5-diamino-6-chloropyrazine-2-carboxylate (Intermediate 2; 2.00 g; 6.10 mmol) are added and the mixture is stirred at room temperature over night. The organic solvents are evaporated, then water (50 mL) is added. The precipitate formed is collected by filtration while applying suction, washed successively with water, methanol and then with diethyl ether and then dried at 50° C. to yield the title compound (1.33 g, 84% of theory).

Intermediate 3.1

3,5-Diamino-6-Bromo-N-[(methylsulfanyl)methanimidoyl]pyrazine-2-carboxamide

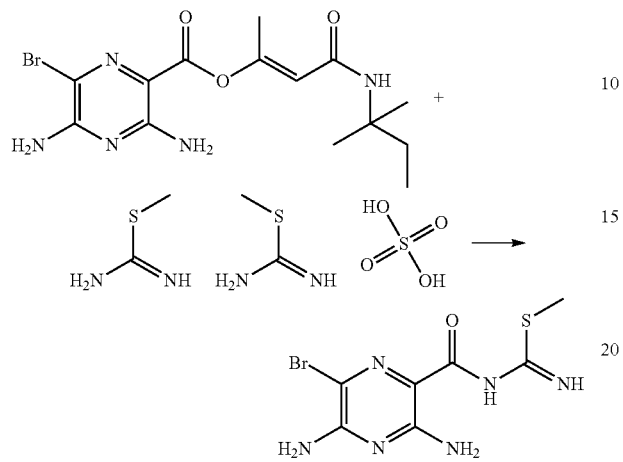

Intermediate 3.1

To NaOH (1 mol/l in water; 30 mL; 30 mmol) is added S-methylisothiourea sulphate (5.42 g; 19.5 mmol. The mixture is stirred until complete solution is achieved. TBME/THF (1:1; 100 mL) and then 1-(2-methyl-2-butyl-carbamoyl)prop-1-en-2-yl 3,5-diamino-6-bromopyrazine-2-carboxylate (Intermediate 2.1; 7.52 g; 19.5 mmol) are added and the mixture is stirred at r.t. overnight, then water (100 mL) is added. The precipitate formed is filtered off with suction, washed with THF/water (1:2) and then dried at 50° C. to yield the title compound.
Yield: 5.44 g (92% of theory)
$C_7H_9BrN_6OS$ ESI Mass spectrum: m/z=305 [M+H]+

Intermediate 4

N-(1-Aza-bicyclo[2.2.2]oct-3-yl)-N'-(3,5-diamino-6-chloro-pyrazine-2-carbonyl)-guanidine

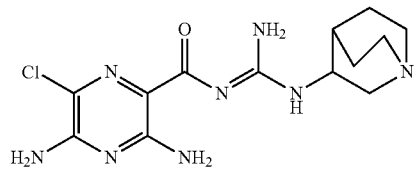

3,5-Diamino-6-chloro-N-[(methylsulfanyl)methanimidoyl]pyrazine-2-carboxamide (Intermediate 3, 250 mg, 0.88 mmol) is dissolved in tetrahydrofuran (20 mL) and to the solution 3-amino-quinuclidine dihydrochloride (211 mg, 1.06 mmol) and triethylamine (0.61 mL, 4.41 mmol) are added. The mixture is heated at 80° C. for 24 hours. The solid is removed by filtration and the is filtrate evaporated and purified by preparative HPLC (5 mM ammonium formate in $H_2O$: $CH_3CN$ gradient) obtaining the title compound (45 mg).
LC/MS (Method A): RT=1.00 min, m/z=339 [M+H]+.

Alternatively to the purification by preparative HPLC the crude product obtained from evaporation to dryness of the above filtrate may be directly used in the next step.

In analogy, using Intermediate 3 and the commercially available (R)- or (S)-3-amino-quinuclidine dihydrochloride salts the following compounds are obtained:

Intermediate 5

N-(R)-1-Aza-bicyclo[2.2.2]oct-3-yl-N'-(3,5-diamino-6-chloro-pyrazine-2-carbonyl)-guanidine

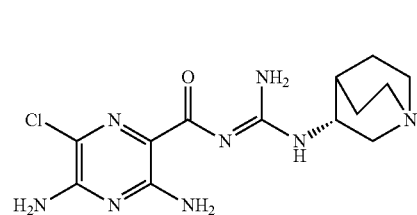

LC/MS (Method A): RT=1.00 min, m/z=339 [M+H]+.

Intermediate 6

N-(S)-1-Aza-bicyclo[2.2.2]oct-3-yl-N'-(3,5-diamino-6-chloro-pyrazine-2-carbonyl)-guanidine

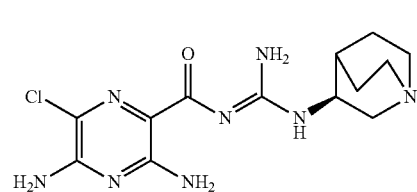

LC/MS (Method A): RT=1.00 min, m/z=339 [M+H]+.

Analogously, using Intermediate 3.1 and (S)-3-amino-quinuclidine dihydrochloride, the following compound is obtained:

Intermediate 6.1

N-(S)-1-Aza-bicyclo[2.2.2]oct-3-yl-N'-(3,5-diamino-6-bromo-pyrazine-2-carbonyl)-guanidine

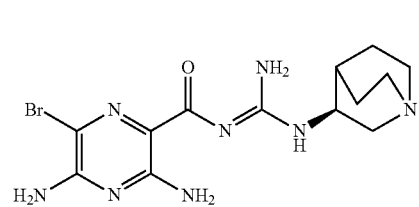

LC/MS (Method H): RT=0.55 min, m/z=381 [M−H]−.

Intermediate 7

4-Amino-1-(4-methoxycarbonyl-benzyl)-1-methyl-piperidinium trifluoracetate

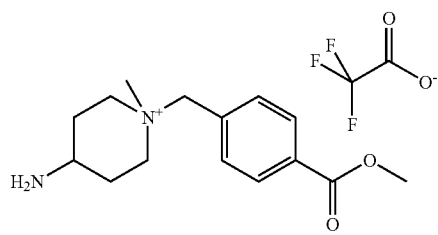

Intermediate 7

Step A: 4-(4-tert-Butoxycarbonylamino-piperidin-1-ylmethyl)-benzoic acid methyl ester

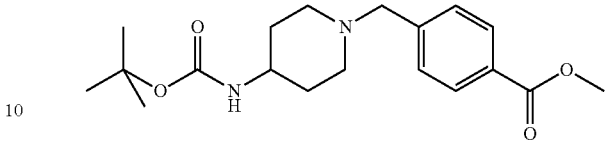

Intermediate 7A

A mixture of 4-bromomethyl-benzoic acid methyl ester (3.0 g; 15 mmol), piperidin-4-yl-carbamic acid tert-butyl ester (3.77 g; 16.5 mmol) and potassium carbonate (4.35 g, 31.5 mmol) in 100 ml acetonitrile is stirred for 5 h at 80° C. Precipitates were removed by filtration and the solution is evaporated. The residue is purified by silica gel column chromatography (gradient: DCM/Methanol 98:2 to 95:5 to yield 4-(4-tert-Butoxycarbonylamino-piperidin-1-ylmethyl)-benzoic acid methyl ester.

Yield: 2.49 g $C_{19}H_{28}N_2O_4$ ESI mass spectrum: m/z=349 [M+H]$^+$

The following compounds are prepared accordingly from the starting materials as indicated:

TABLE 1

| Intermediate | Structure | Starting material |
| --- | --- | --- |
| 7.1A | 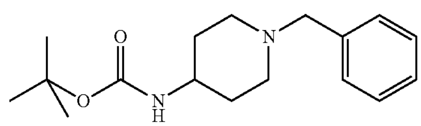 [SMILES: CC(C)(C)OC(=O)NC1CCN(Cc2ccccc2)CC1] | Bromomethyl-benzene and piperidin-4-yl-carbamic acid tert-butyl ester |
| 7.3A | 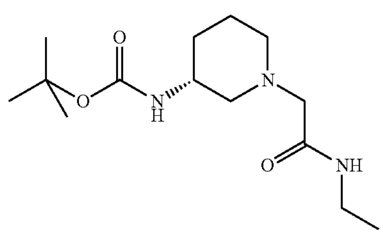 [SMILES: CCNC(=O)CN1CCC[C@@H](NC(=O)OC(C)(C)C)C1] | 2-Bromo-N-ethyl-acetamide and (R)-piperidin-3-yl-carbamic acid tert-butyl ester |
| 7.4A | 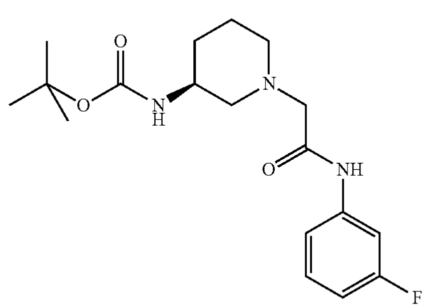 [SMILES: CC(C)(C)OC(=O)N[C@H]1CCCN(CC(=O)Nc2cccc(F)c2)C1] | 2-Bromo-N-(3-fluoro-phenyl)-acetamide and (S)-piperidin-3-yl-carbamic acid tert-butyl ester |

TABLE 1-continued

| Intermediate | Structure | Starting material |
|---|---|---|
| 7.5A | 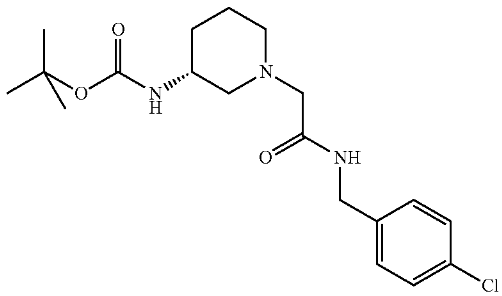 [SMILES: CC(C)(C)OC(=O)N[C@@H]1CCCN(CC(=O)NCc2ccc(Cl)cc2)C1] | 2-Bromo-N-(4-chloro-phenyl)-acetamide and (R)-piperidin-3-yl-carbamic acid tert-butyl ester |
| 7.6A | 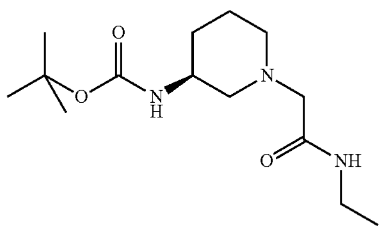 [SMILES: CCNC(=O)CN1CCC[C@H](NC(=O)OC(C)(C)C)C1] | 2-Bromo-N-ethyl-acetamide and (S)-piperidin-3-yl-carbamic acid tert-butyl ester |
| 7.7A | 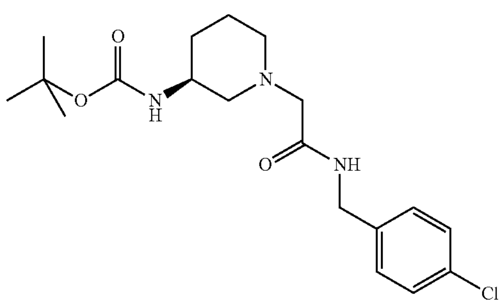 [SMILES: CC(C)(C)OC(=O)N[C@H]1CCCN(CC(=O)NCc2ccc(Cl)cc2)C1] | 2-Bromo-N-(4-chloro-phenyl)-acetamide and (S)-piperidin-3-yl-carbamic acid tert-butyl ester |
| 7.8A | 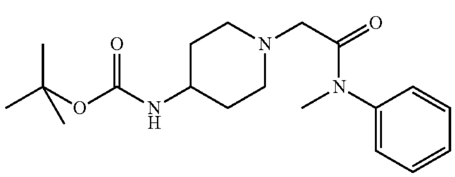 [SMILES: CN(C(=O)CN1CCC(NC(=O)OC(C)(C)C)CC1)c1ccccc1] | Piperidin-4-yl-carbamic acid tert-butyl ester and 2-Chloro-N-methyl-N-phenyl-acetamide |
| 7.9A | 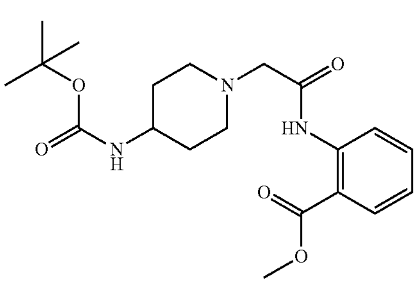 [SMILES: COC(=O)c1ccccc1NC(=O)CN1CCC(NC(=O)OC(C)(C)C)CC1] | Piperidin-4-yl-carbamic acid tert-butyl ester and 2-chloro-N-(2-methoxycarbonyl-phenyl)-acetamide |

7.10A 1-[(Benzyl-methyl-carbamoyl)-methyl]-piperidin-4-yl}-carbamic acid tert-butyl ester

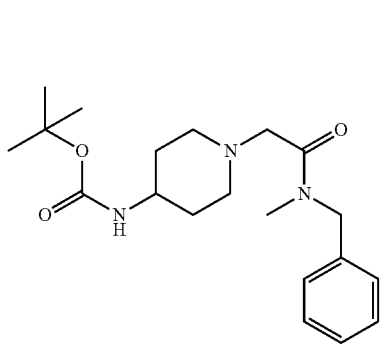

To a solution of 200 mg piperidin-N-acetic acid 4-yl-carbamic acid tert-butyl ester in 10 ml DMF is added 125 mg carbonyldiimidazole. The mixture is stirred at 70° C. for 2 h. Then 100 µl N-methyl-benzyl-amine is added and the reaction is stirred at room temperature overnight. The reaction mixture is evaporated under reduced pressure and the residue is treated with 10 ml methylenechloride. The organic phase is washed with 5 ml 1 N NaOH and evaporated under reduced pressure yielding the title product.

Step B:

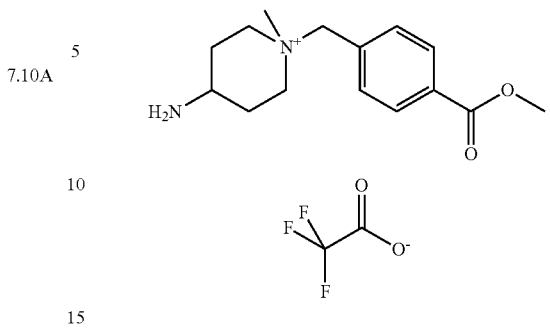

7.10A

To a solution of 4-(4-tert-butoxycarbonylamino-piperidin-1-ylmethyl)-benzoic acid methyl ester (185 mg; 0.5 mmol) in 5 ml acetone is added 133 µl methyl iodide. The mixture is stirred at room temperature overnight. Then the precipitate is collected, washed with acetone and dried yielding 145 mg of solid material.

(Removal of BOC protecting group): A mixture of this residue is treated with 8 ml 25% TFA in dichloromethane and stirred for 2 h at room temperature. The mixture is evaporated to yield the title compound as a trifluoroacetate.

Yield: 200 mg
$C_{15}H_{23}N_2O_2 \times C_2F_3O_2 \times C_2HF_3O_2$
Mass spectrum: m/z=263 [M]$^+$ The following compounds are prepared accordingly from the starting materials as indicated:

TABLE 2

| Intermediate | Structure | Starting Material |
|---|---|---|
| 7.1 | 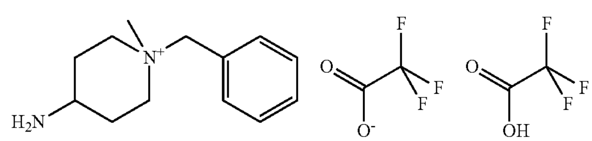 | 7.1A |
| 7.2 | 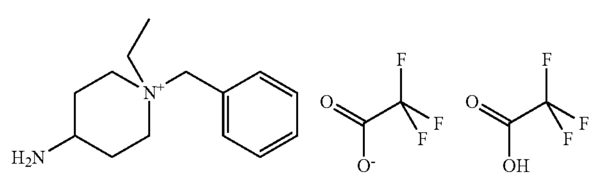 [SMILES: CC[N+]1(Cc2ccccc2)CCC(N)CC1 ; O=C([O-])C(F)(F)F ; O=C(O)C(F)(F)F] | 7.1A and ethyl iodide |
| 7.3 | 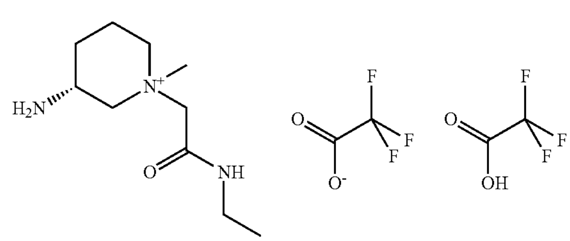 | 7.3A and methyl iodide |

TABLE 2-continued

| Intermediate | Structure | Starting Material |
|---|---|---|
| 7.4 | (3-aminopiperidinium, N-methyl, CH2C(O)NH-(3-fluorophenyl)), 2 TFA | 7.4A and methyl iodide |
| 7.5 | (3-aminopiperidinium, N-methyl, CH2C(O)NH-CH2-(4-chlorophenyl)), 2 TFA | 7.5A and methyl iodide |
| 7.6 | (3-aminopiperidinium, N-methyl, CH2C(O)NH-ethyl), 2 TFA | 7.6A and methyl iodide |
| 7.7 | (3-aminopiperidinium, N-ethyl, CH2C(O)NH-(3-fluorophenyl)), 2 TFA | 7.4A and ethyl iodide |

Intermediate 8

(S)-2-(3-Amino-piperidin-1-yl)-N-(4-chloro-benzyl)-acetamide

Intermediate 8

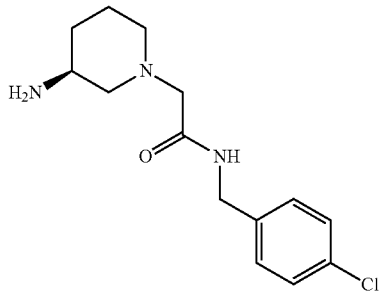

A solution of 60 mg (S)-{1-[(4-Chloro-benzylcarbamoyl)-methyl]-piperidin-3-yl}-carbamic acid tert-butyl ester (intermediate 7.7A) in 5 ml dichloromethane is treated with 50 μl TFA and stirred overnight at room temperature. The mixture is evaporated to yield the title compound as a trifluoroacetate.

Yield: 85 mg
$C_{15}H_{23}N_2O_2 \times C_2F_3O_2 \times C_2HF_3O_2$
Mass spectrum: m/z=282 [M+H]$^+$ The following compounds are prepared accordingly from the starting materials as indicated:

| Intermediate | Structure | Starting Material |
|---|---|---|
| 8.1 | (structure with piperidine, H₂N, N-methyl-N-phenyl acetamide) | 7.8 A |
| 8.2 | (structure with piperidine, H₂N, N-methyl-N-benzyl acetamide) | 7.10A |
| 8.3 | (structure with piperidine, H₂N, anilide with methyl ester) | 7.9.A |

Intermediate 9

(S)-N-(1-Benzyl-piperidin-3-yl)-N'-(3,5-diamino-6-chloro-pyrazine-2-carbonyl)-guanidine Intermediate 9

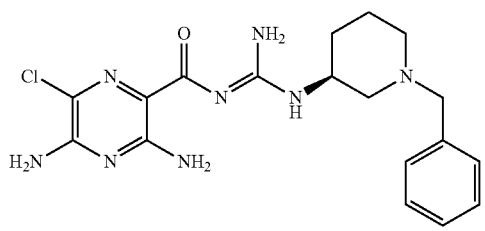

A mixture of 60 mg (0.27 mmol) 3,5-diamino-6-chloro-N[(methylsulfanyl)methanimidoyl]-pyrazine-2-carboxamide (intermediate 3) and 60 mg (S)-3-amino-1-benzyl-piperidine in 2 ml THF is stirred at 70° C. overnight. Then the reaction mixture is concentrated under reduced pressure and the residue is purified by preparative reverse phase HPLC (gradient of acetonitrile and water+0.2% trifluoroacetic acid, 25° C.). Fractions containing the title compound were concentrated under reduced pressure treated with excess HCl in methanol and evaporated again.

Yield: 100 mg.
ESI mass spectrum: [M+H]$^+$=403
Retention time HPLC: 0.82 min (method D).

The following compounds are prepared accordingly from the starting materials as indicated:

TABLE 3

| Intermediate | Structure | Starting Material |
|---|---|---|
| 9.1 | (3,5-diamino-6-chloropyrazine-2-carbonyl guanidine linked to piperidine-N-CH₂C(O)NH-4-chlorobenzyl) | Intermediate 8 and intermediate 3 |

TABLE 3-continued

| Intermediate | Structure | Starting Material |
|---|---|---|
| 9.2 | 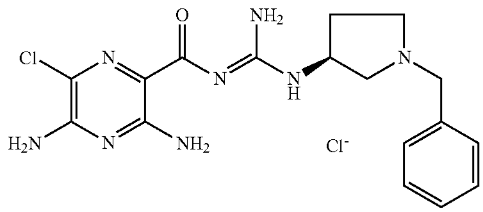 [SMILES: N/C(=N\C(=O)c1nc(Cl)c(N)nc1N)N[C@H]1CCN(Cc2ccccc2)C1 ; [Cl-]] | intermediate 3 and (S)-1-benzyl-pyrrolidin-3-ylamine |
| 9.3 | 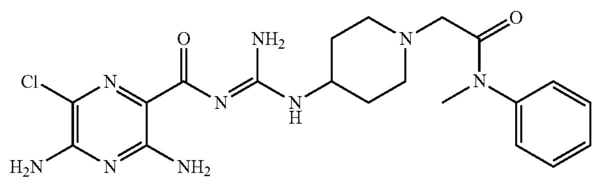 [SMILES: CN(C(=O)CN1CCC(N/C(N)=N/C(=O)c2nc(Cl)c(N)nc2N)CC1)c1ccccc1] | Intermediate 8.1 and intermediate 3 |
| 9.4 | 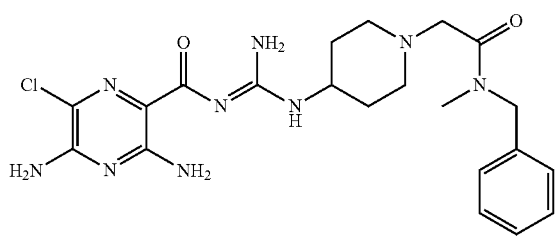 [SMILES: CN(Cc1ccccc1)C(=O)CN1CCC(N/C(N)=N/C(=O)c2nc(Cl)c(N)nc2N)CC1] | Intermediate 8.2 and intermediate 3 |
| 9.5 | 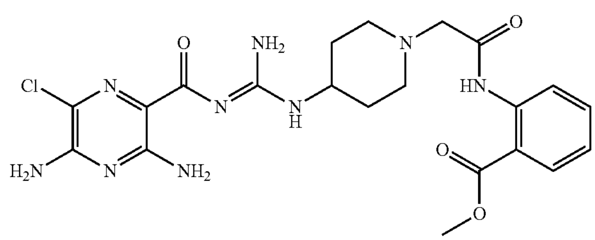 [SMILES: COC(=O)c1ccccc1NC(=O)CN1CCC(N/C(N)=N/C(=O)c2nc(Cl)c(N)nc2N)CC1] | Intermediate 8.3 and intermediate 3 |

Intermediate 10

(S)-3-{3-[N'-(3,5-Diamino-6-chloro-pyrazine-2-carbonyl)-guanidino]-piperidin-1-ylmethyl}-benzoic acid methyl ester Intermediate 10

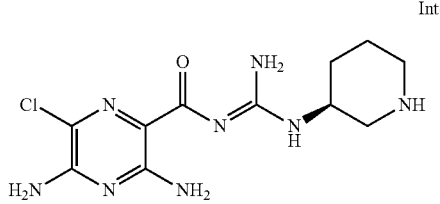

Step A: A mixture of 1.17 g (4.5 mmol) 4-Aminomethyl-4-phenethyl-piperidine-1-carbocylic acid tert-butyl ester (intermediate 3), 1 mg (4.9 mmol) (S)-3-amino-piperidine-1-carboxylic acid tert-butyl ester and 125 µl triethylamin in 50 ml DMF/iso-propanol (1:3) is stirred at 70° C. overnight. Then the reaction mixture is concentrated under reduced pressure. Then 50 ml 25% TFA in dicholoromethane is added and the mixture is stirred for 2 h at room temperature and evaporated. The residue is treated with excess HCl in methanol and evaporated again to yield 430 mg N-(3,5-Diamino-6-chloro-pyrazine-2-carbonyl)-N'-piperidin-3-yl-guanidine.

Step B: 100 mg N-(3,5-Diamino-6-chloro-pyrazine-2-carbonyl)-N'-piperidin-3-yl-guanidine, 125 µl triethylamine and 62 mg 3-bromomethyl-benzoic acid methyl ester in 3 ml DMF were stirred at room temperature for 6 h. Then the reaction mixture is concentrated under reduced pressure and the residue is purified by preparative reverse phase HPLC (gradient of acetonitrile and water+0.2% trifluoroacetic acid, 25° C.). Fractions containing the title compound were concentrated under reduced pressure.

Yield: 77 mg.

Intermediate 11

1-Bromomethyl-3-methylsulfanyl-benzene

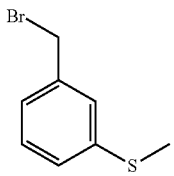

Intermediate 11

Step A: A solution of 1.50 g (8.92 mmol) 3-(methylthio) benzoic acid (Aldrich) in 20 mL of dry dichloromethane is cooled to 0° C. and 1.86 mL (19.6 mmol) borane-methylsulfide complex (Aldrich) is added. The solution is allowed to reach room temperature and stirred overnight, then hydrochloric acid (4 M, 50 mL) is added and the resulting mixture is stirred for additional 2 h. The reaction mixture is extracted with ethyl acetate (50 mL, 3 times) and the collected organic phases are washed with 10% NaHCO$_3$ solution and brine and volatiles evaporated under vacuum to yield 3-methylsulfanyl-phenyl)-methanol (1.20 g, content ca. 75%), which is directly used in the next step.

Step B: A solution of 3-methylsulfanyl-phenyl)-methanol (1.20 g, content ca 75%) in dichloromethane (25 mL) and phosphorus tribromide (1 M in dichloromethane, 6.42 mL) is stirred for 3 h at room temperature. The reaction mixture is washed with NaHCO3 solution (10%, 10 mL, 2 times) and the remaining organic phase is dried (MgSO4) and volatiles are evaporated under reduced pressure to yield the title compound (1.35 g).

Intermediate 12

N,N'-Dibenzyl-2-bromo-malonamide

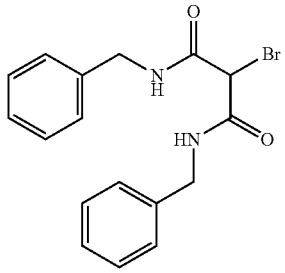

Intermediate 12

A solution of 1.12 g (content ca. 90%, 3.49 mmol) N,N-dibenzyl-malonamide (preparation according to: *Journal of the Chemical Society* 1921, vol. 119, 360.) in acetic acid (10 mL) is heated at 60° C. and 0.2 mL (3.97 mmol) bromine in 4 mL of acetic acid is added dropwise. Upon cooling to room temperature and stirring overnight a solid precipitates which is collected by filtration, washed with some diethyl ether and finally dried under vacuum in an oven (50° C.) to give the title compound (0.56 g)

mass spectrum m/z=361 [M+H]$^+$.

Intermediate 13

2-Bromo-N-ethyl-2-phenyl-acetamide

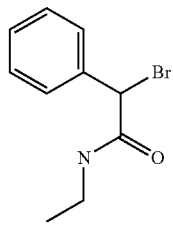

Intermediate 13

A mixture of 1.0 g (4.65 mmol) alpha-bromophenylacetic acid (Aldrich), 1.16 g (6.05 mmol) (3-dimethylamino-propyl)-ethyl-carbodiimide hydrochloride (Aldrich), 2.80 mL (5.6 mmol) ethyl-amine (Aldrich, 2 M in dichloromethane) in dichloromethane (30 mL) is stirred at room temperature for 18 h. The reaction mixture is washed with NaOH 1 M (15 mL) and the organic phase is evaporated under reduced pressure. The residue is purified by silica gel column chromatography (gradient: cyclohexane/ethyl acetate 90:10 to 50:50) to yield the title compound (0.32 g, content ca. 90%).

mass spectrum m/z=243 [M+H]$^+$.

Intermediate 14

(S)-2-(2-Chloro-acetylamino)-3-phenyl-propionic acid tert-butyl ester

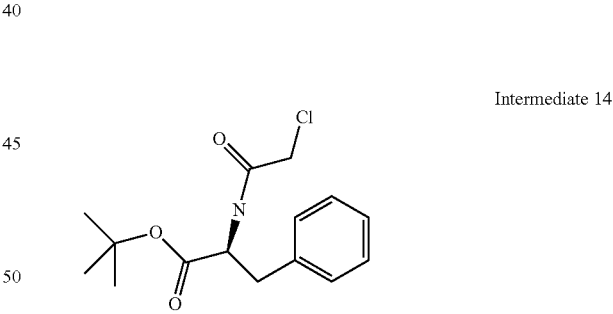

Intermediate 14

To a mixture of 3.0 g (11.6 mmol) (S)-2-amino-3-phenyl-propionic acid tert-butyl ester hydrochloride (Aldrich) and 3.32 mL (23.9 mmol) triethylamine (Aldrich) in dichloromethane (30 mL), 0.97 mL (12.2 mmol) chloroacetyl chloride (Aldrich) is added dropwise and the resulting mixture is stirred at room temperature for 4 h. The reaction mixture is diluted with water (25 mL), the organic layer is separated, washed with 10% NaHCO$_3$ solution (25 mL), dried (MgSO$_4$) and finally evaporated under reduced pressure to yield the title compound (3.4 g).

mass spectrum m/z=298 [M+H]$^+$.

The compounds in Table 4 are prepared in analogy to Intermediate 14 from the starting materials indicated

TABLE 4

| Intermediate | Structure | Starting Materials |
| --- | --- | --- |
| 14.1 | 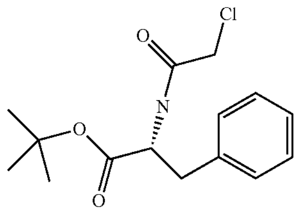 [SMILES: CC(C)(C)OC(=O)[C@@H](Cc1ccccc1)NC(=O)CCl] | |
| 14.2 | 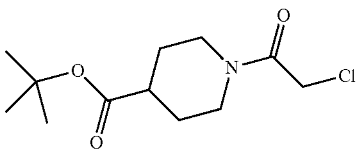 [SMILES: CC(C)(C)OC(=O)C1CCN(C(=O)CCl)CC1] | |
| 14.3 | 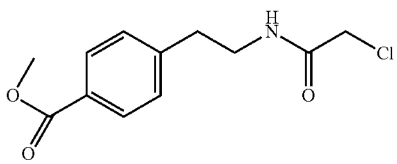 [SMILES: COC(=O)c1ccc(CCNC(=O)CCl)cc1] | |
| 14.4 | 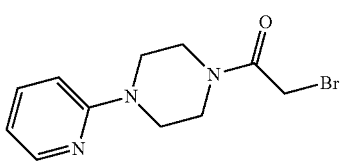 [SMILES: O=C(CBr)N1CCN(c2ccccn2)CC1] | |
| 14.5 | 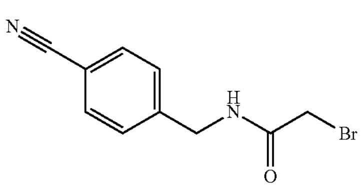 [SMILES: N#Cc1ccc(CNC(=O)CBr)cc1] | |

TABLE 4-continued

| Intermediate | Structure | Starting Materials |
|---|---|---|
| 14.6 | (bromoacetamide of ethyl 4-aminopiperidine-1-carboxylate) | ethyl 4-aminopiperidine-1-carboxylate and bromoacetyl bromide |
| 14.7 | 1-(2-bromoacetyl)-4-(pyrimidin-2-yl)piperazine | 2-(piperazin-1-yl)pyrimidine and 1,3-dibromoacetone (Br-CH2-CO-CH2-Br) |
| 14.8 | 2-chloro-N-methyl-N-phenethylacetamide | N-methyl-2-phenylethan-1-amine and chloroacetyl chloride |

7.2 Synthesis of Examples

Example 1

1-Carboxymethyl-3-[N'-(3,5-diamino-6-chloro-pyrazine-2-carbonyl)-guanidino]-1-azoniabicyclo[2.2.2]octane bromide

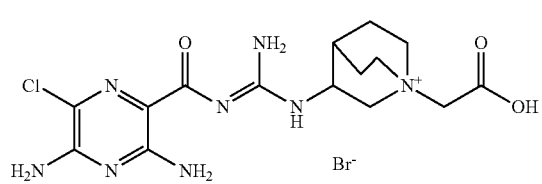

1

N-(1-Aza-bicyclo[2.2.2]oct-3-yl)-N'-(3,5-diamino-6-chloro-pyrazine-2-carbonyl)-guanidine (Intermediate 4, 152 mg, content ca. 66%, 0.30 mmol) and benzyl bromoacetate (Aldrich, 0.052 mL, 0.33 mmol) are treated with DMF (1 mL) and the mixture stirred at r.t. for ca. 18 h. The crude mixture is purified by preparative HPLC (5 mM ammonium formate in H$_2$O: CH$_3$CN gradient) and further on a PoraPak Rxn RP cartridge (Waters, 6 mL), eluting with 0% to 100% acetonitrile in water. Drying under vacuum yields the title compound (23 mg).

LC/MS (Method B): RT=3.17 min, m/z=397 [M]$^+$.
ENaC IC50 (μM): 0.468.

Example 2

3-[N'-(3,5-Diamino-6-chloro-pyrazine-2-carbonyl)-guanidino]-1-(3,4,5-trimethoxybenzyl)-1-azoniabicyclo[2.2.2]octane chloride

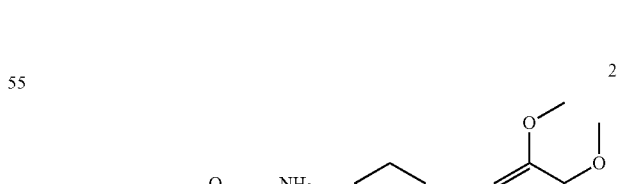

2

N-(1-Aza-bicyclo[2.2.2]oct-3-yl)-N'-(3,5-diamino-6-chloro-pyrazine-2-carbonyl)-guanidine (Intermediate 4, 152 mg, content ca. 66%, 0.30 mmol) and 3,4,5-trimethoxybenzyl chloride (Aldrich, 77 mg, 0.36 mmol) is stirred in DMF (1 mL) at r.t. for ca. 18 h. The crude mixture is purified by preparative HPLC (5 mM ammonium formate in $H_2O$: $CH_3CN$ gradient). The product thus obtained is triturated with a mixture of diethyl ether (4 mL) and methanol (1.5 mL), collected by filtration and dried under vacuum at 70° C. Further trituration with water (0.3 mL), filtration and drying under vacuum at 70° C. yields the title compound (35 mg).

LC/MS (Method A): RT=1.44 min, m/z=519 [M]$^+$.

ENaC IC50 (μM): 0.126.

Analogously, using Intermediate 4, the appropriate alkylant and trituration with acetonitrile/diethyl ether the following compound is obtained:

Example 3

3-[N'-(3,5-Diamino-6-chloro-pyrazine-2-carbonyl)-guanidino]-1-phenylcarbamoylmethyl-1-azoniabicyclo[2.2.2]octane chloride

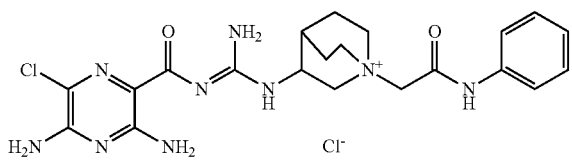

LC/MS (Method B): RT=7.78 min, m/z=472 [M]$^+$.

ENaC IC50 (μM): 0.026.

Example 4

1-Benzyl-3-[N'-(3,5-diamino-6-chloro-pyrazine-2-carbonyl)-guanidino]-1-azoniabicyclo[2.2.2]octane bromide

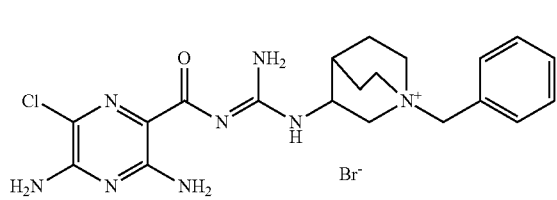

N-1-Aza-bicyclo[2.2.2]oct-3-yl-N'-(3,5-diamino-6-chloro-pyrazine-2-carbonyl)-guanidine (Intermediate 4, 30 mg, 0.089 mmol) and benzyl bromide (Acros, 17 mg, 0.097 mmol) are stirred for 4 h at 70° C. in acetonitrile (2 mL). To the suspension is added diethyl ether (2 mL), the solid collected by filtration, washed with diethyl ether and dried under vacuum to yield the title compound (26 mg).

LC/MS (Method A): RT=1.25 min, m/z=429 [M]$^+$.

ENaC IC50 (μM): 0.043.

Example 5

(R)-1-Benzyl-3-[N'-(3,5-diamino-6-chloro-pyrazine-2-carbonyl)-guanidino]-1-azoniabicyclo[2.2.2]octane bromide

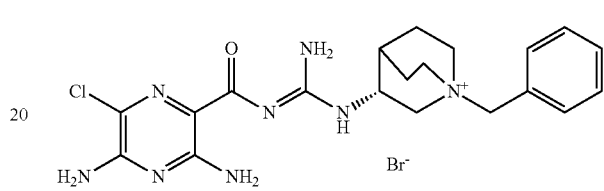

N-(R)-1-Aza-bicyclo[2.2.2]oct-3-yl-N'-(3,5-diamino-6-chloro-pyrazine-2-carbonyl)-guanidine (Intermediate 5, 93 mg, content ca. 70%, 0.19 mmol) and benzyl bromide (Acros, 0.028 mL, 0.23 mmol) are stirred for 4 h in DMF (3 mL). The resulting material is purified by preparative HPLC (5 mM ammonium formate in $H_2O$: $CH_3CN$ gradient) to yield the title compound (17 mg).

LC/MS (Method A): RT=1.19 min, m/z=429 [M]$^+$.

ENaC IC50 (μM): 0.460.

Example 6

(S)-1-Benzyl-3-[N'-(3,5-diamino-6-chloro-pyrazine-2-carbonyl)-guanidino]-1-azoniabicyclo[2.2.2]octane bromide

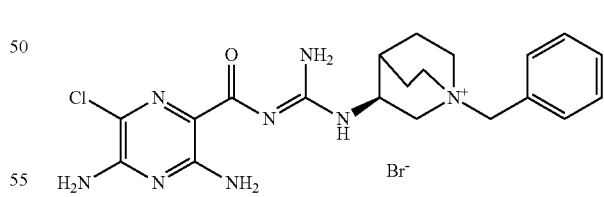

N-(S)-1-Aza-bicyclo[2.2.2]oct-3-yl-N'-(3,5-diamino-6-chloro-pyrazine-2-carbonyl)-guanidine (Intermediate 6, 50 mg, 0.15 mmol) and benzyl bromide (Acros, 30 mg, 0.18 mmol) are stirred for ca. 18 h at 70° C. in acetonitrile (4 mL). To the suspension is added diethyl ether (2 mL), the solid collected by filtration, washed twice with diethyl ether and dried under vacuum to yield the title compound (48 mg).

LC/MS (Method A): RT=1.20 min, m/z=429 [M]$^+$.

ENaC IC50 (μM): 0.028.

Example 6.1

(S)-1-Benzyl-3-[N'-(3,5-diamino-6-bromo-pyrazine-2-carbonyl)-guanidino]-1-azoniabicyclo[2.2.2]octane bromide 6.1

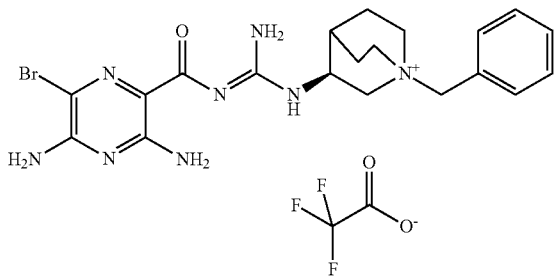

N-(S)-1-Aza-bicyclo[2.2.2]oct-3-yl-N'-(3,5-diamino-6-bromo-pyrazine-2-carbonyl)-guanidine (Intermediate 6.1, 80 mg, 0.209 mmol) and benzyl bromide (0.025 mg, 0.209 mmol) are stirred overnight at r.t in DMSO/2-propanol 1:1 (2 mL). Volatiles are evaporated and the residue is purified by preparative HPLC($H_2O$+0.05% $CF_3COOH$:$CH_3CN$ gradient) to yield the title compound (57 mg).

LC/MS (Method I): RT=0.54 min, m/z=473 $[M]^+$.
ENaC IC50 (µM): 0.029.

Example 7

(S)-3-[N'(3,5-Diamino-6-chloro-pyrazine-2-carbonyl)-guanidino]-1-(4-methoxybenzyl)-1-azoniabicyclo[2.2.2]octane chloride

7

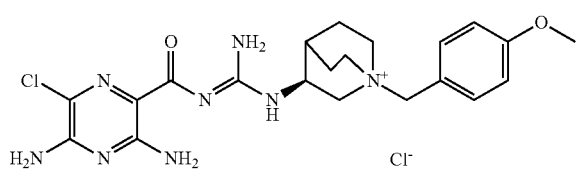

N-(S)-1-Aza-bicyclo[2.2.2]oct-3-yl-N'-(3,5-diamino-6-chloro-pyrazine-2-carbonyl)-guanidine (Intermediate 6), 125 mg, content ca. 87%, 0.32 mmol) and 4-methoxybenzyl chloride (Aldrich, 0.027 mL, 0.20 mmol) in DMF (1 mL) are stirred at r.t. for ca. 18 h. Acetonitrile (3 mL) is added, the resulting solid removed by filtration and volatiles removed from the mother liquor. Trituration of the residue with acetonitrile and drying under vacuum yields the title compound (25 mg).

LC/MS (Method A): RT=1.34 min, m/z=459 $[M]^+$.
ENaC IC50 (µM): 0.020.

Example 8

(S)-1-(4-tert-Butyl-benzyl)-3-[N'-(3,5-diamino-6-chloro-pyrazine-2-carbonyl)-guanidino]-1-azoniabicyclo[2.2.2]octane chloride

8

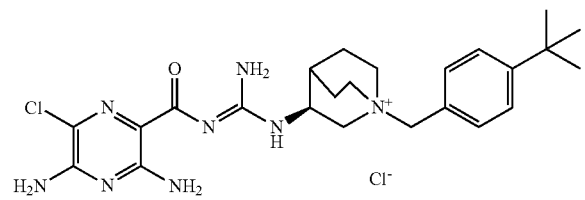

N-(S)-1-Aza-bicyclo[2.2.2]oct-3-yl-N'-(3,5-diamino-6-chloro-pyrazine-2-carbonyl)-guanidine (Intermediate 6, 125 mg, content ca. 87%, 0.32 mmol) and 4-tert-butyl-benzyl bromide (Aldrich, 0.074 mL, 0.40 mmol) in DMF (1 mL) are stirred at r.t. for ca. 18 h. Acetonitrile (8 mL) is added and the resulting solid removed by filtration. Upon cooling at ca. 4° C. for ca. 18 h another solid forms from the mother liquor. This is collected by filtration and purified by preparative HPLC ($H_2O$+0.05% $CF_3COOH$:$CH_3CN$ gradient). The material thus obtained is treated three times in acetonitrile (10 mL) with HCl (2 M in diethyl ether, 1.5 mL) followed by evaporation. Finally, trituration with diethyl ether, filtration and drying under vacuum yields the title compound (23 mg).

LC/MS (Method A): RT=2.05, 5.51 min, m/z=485 $[M]^+$.
ENaC IC50 (µM): 0.041.

The following compounds are obtained analogously to Example 8 by reaction between Intermediate 6 and the appropriate alkylating agents, employing suitable solvents for trituration:

TABLE 5

| Example | $L^1$ and $X^-$ | $L^3$ | Solvent for titration | LC/MS (Method A): RT | m/z | ENaC IC50 (µM) |
|---|---|---|---|---|---|---|
| 9 | ![structure] Cl⁻ | ![structure] CF₃ | diethyl ether/ ethanol | 2.02, 3.59 min | 529 $[M]^+$ | 0.003 |

TABLE 5-continued

| Example | L¹ and X⁻ | L³ | Solvent for titration | LC/MS (Method A): RT | m/z | ENaC IC50 (μM) |
|---|---|---|---|---|---|---|
| 10 | | | acetonitrile/ diethyl ether | 2.01, 2.37 min | 529 [M]⁺ | 0.060 |

Example 11

(S)-3-[N'-(3,5-Diamino-6-chloro-pyrazine-2-carbonyl)-guanidino]-1-quinolin-2-ylmethyl-1-azoniabicyclo[2.2.2]octane chloride

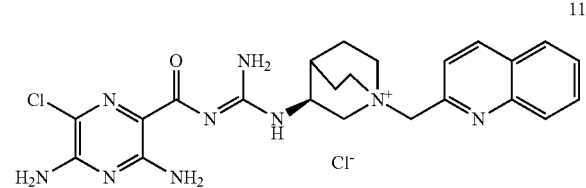 [SMILES: N/C(=N\C(=O)c1nc(Cl)c(N)nc1N)N[C@@H]1C[N+]2(Cc3ccc4ccccc4n3)CCC1CC2 ; [Cl-]]

11

N-(S)-1-Aza-bicyclo[2.2.2]oct-3-yl-N'-(3,5-diamino-6-chloro-pyrazine-2-carbonyl)-guanidine (Intermediate 6, 125 mg, content ca. 87%, 0.32 mmol), 2-(chloromethyl)quinoline hydrochloride (Aldrich, 76 mg, 0.35 mmol) and sodium hydrogen carbonate (Fluka, 27 mg, 0.32 mmol) in DMF (1 mL) are stirred at r.t. for ca. 18 h. Solids are removed by filtration and acetonitrile (3 mL) is added to the filtrate. After stirring for 1 hour the resulting solid is collected by filtration, triturated with acetonitrile:methanol (1:1, 2 mL), filtered and dried under vacuum to yield the title compound (45 mg).

LC/MS (Method A): RT=1.81 min, m/z=480 [M]⁺.

ENaC IC50 (μM): 0.029.

Example 12

(S)-3-[N'-(3,5-Diamino-6-chloro-pyrazine-2-carbonyl)-guanidino]-1-(6-trifluoromethyl-pyridin-3-ylmethyl)-1-azonia-bicyclo[2.2.2]octane chloride

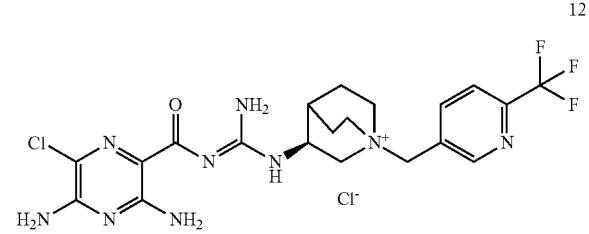 [SMILES: N/C(=N\C(=O)c1nc(Cl)c(N)nc1N)N[C@@H]1C[N+]2(Cc3ccc(C(F)(F)F)nc3)CCC1CC2 ; [Cl-]]

12

N-(S)-1-Aza-bicyclo[2.2.2]oct-3-yl-N'-(3,5-diamino-6-chloro-pyrazine-2-carbonyl)-guanidine (Intermediate 6, 120 mg, content ca. 81%, 0.26 mmol), 3-(chloromethyl)-6-(trifluoromethyl)pyridine (Apollo, 66 mg, 0.34 mmol) in DMF (1 mL) are stirred at r.t. for ca. 18 h. DMF (1.5 mL) is to added, the solid collected by filtration and washed with some acetonitrile. The material is dissolved in a few drops EtOH and precipitated by adding some diethyl ether. The resulting solid is collected by filtration and dried under vacuum to yield the title compound (24 mg).

LC/MS (Method A): RT=1.34 min, m/z=498 [M]⁺.

ENaC IC50 (μM): 0.063.

Example 13

(S)-3-[N'-(3,5-Diamino-6-chloro-pyrazine-2-carbonyl)-guanidino]-1-pyridin-2-ylmethyl-1-azoniabicyclo[2.2.2]octane chloride

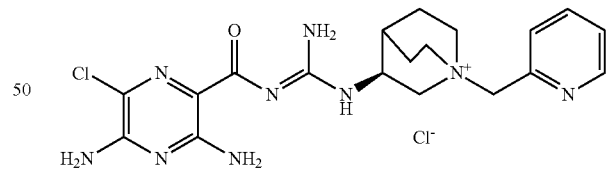

13

N-(S)-1-Aza-bicyclo[2.2.2]oct-3-yl-N'-(3,5-diamino-6-chloro-pyrazine-2-carbonyl)-guanidine (Intermediate 6, 125 mg, content ca. 87%, 0.32 mmol), 2-picolylchloride hydrochloride (Aldrich, 58 mg, 0.35 mmol) and sodium hydrogencarbonate (Fluka, 27 mg, 0.32 mmol) in DMF (1.3 mL) are stirred at r.t. for ca. 18 h. The mixture is purified by preparative HPLC(H₂O+0.05% CF₃COOH:CH₃CN gradient). The material thus obtained is treated three times in acetonitrile with HCl (2 M in diethyl ether, 1.5 mL) followed by evaporation to yield the title compound (23 mg).

LC/MS (Method A): RT=1.11 min, m/z=430 [M]⁺.

ENaC IC50 (μM): 0.090.

Example 14

(S)-3-[N'-(3,5-Diamino-6-chloro-pyrazine-2-carbonyl)-guanidino]-1-(4-fluoro-benzyl)-1-azoniabicyclo[2.2.2]octane chloride

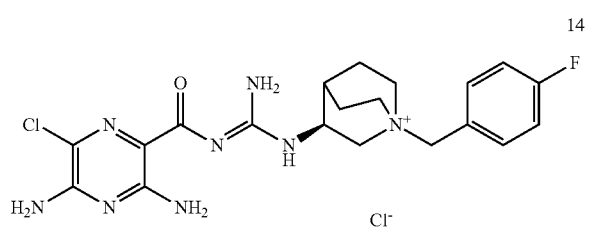 [SMILES: N/C(=N\C(=O)c1nc(Cl)c(N)nc1N)N[C@@H]1C[N+]2(Cc3ccc(F)cc3)CCC1CC2 ; [Cl-]]

N-(S)-1-Aza-bicyclo[2.2.2]oct-3-yl-N'-(3,5-diamino-6-chloro-pyrazine-2-carbonyl)-guanidine (Intermediate 6, 125 mg, content ca. 87%, 0.32 mmol) and 4-fluoro-benzyl chloride (Fluka, 0.057 mL, 0.47 mmol) in DMF (1 mL) are stirred at r.t. for ca. 18 h. Acetonitrile (3 mL) is then added and the mixture kept at 4° C. for ca. 18 h. The resulting solid is collected by filtration and triturated with acetonitrile:diethyl ether (1:1, 3 mL) and then with acetonitrile:isopropanol (6:1, 3.5 mL). Drying under vacuum yields the title compound (71 mg).

LC/MS (Method A): RT=1.30 min, m/z=447 $[M]^+$.

ENaC IC50 (μM): 0.028.

The following compounds are obtained analogously to Example 14 by reaction of intermediate 6 and the appropriate alkylating agents, employing suitable solvents for trituration:

TABLE 6

| Example | $L^1$ and $X^-$ | $L^3$ | Solvent for titration | LC/MS (Method A): RT | m/z | ENaC IC50 (μM) |
|---|---|---|---|---|---|---|
| 15 | Cl⁻ | 4-Cl-phenyl | acetonitrile | Method A: 1.75 min | 463 $[M]^+$ | 0.018 |
| 16 | Br⁻ | 3-OMe-phenyl | acetonitrile/methanol | Method A: 1.44 min | 459 $[M]^+$ | 0.014 |
| 17 | Cl⁻ | 4-CH₂OH-phenyl | acetonitrile/methanol | Method A: 1.09 min | 459 $[M]^+$ | 0.052 |
| 18 | Cl⁻ | 4-CF₃-phenyl | acetonitrile/isopropanol | Method A: 1.78 min | 497 $[M]^+$ | 0.043 |

TABLE 6-continued

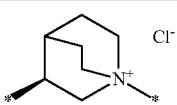

| Example | L¹ and X⁻ | L³ | Solvent for titration | LC/MS (Method A): RT | m/z | ENaC IC50 (μM) |
|---|---|---|---|---|---|---|
| 19 | 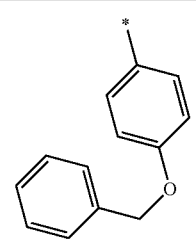 Cl⁻ | 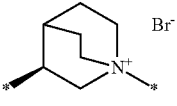 | acetonitrile | Method B: 9.13 | 535 [M]⁺ | 0.032 |
| 20 | 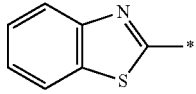 Br⁻ | 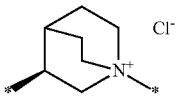 | acetonitrile | Method A: 1.52 min | 486 [M]⁺ | 0.029 |
| 21 | 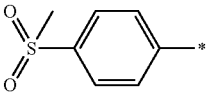 Cl⁻ | 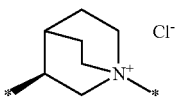 | ethylether/ethanol | Method A: 1.10 min | 507 [M]⁺ | 0.176 |
| 22 | 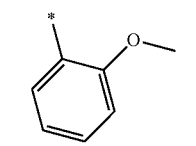 Cl⁻ | 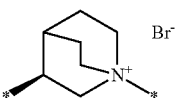 | acetonitrile | Method A: 1.41 min | 459 [M]⁺ | 0.092 |
| 23 |  Br⁻ | 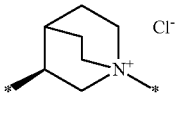 | acetonitrile | Method A: 1.10 min | 391 [M]⁺ | 0.172 |
| 24 | 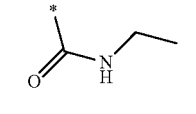 Cl⁻ | 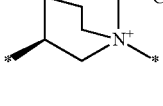 | acetonitrile | Method A: 1.14 min | 424 [M]⁺ | 0.056 |
| 25 | 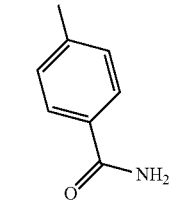 Cl⁻ | 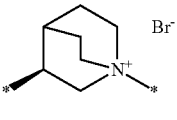 | acetonitrile/isopropanol | Method: 1.05 min | 472 [M]⁺ | 0.693 |
| 26 | 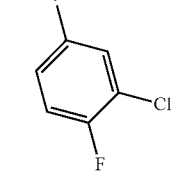 Br⁻ | | acetonitrile | Method A: 1.69 min | 481 [M]⁺ | 0.013 |

TABLE 6-continued

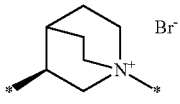

| Example | L¹ and X⁻ | L³ | Solvent for titration | LC/MS (Method A): RT | m/z | ENaC IC50 (μM) |
|---|---|---|---|---|---|---|
| 27 | 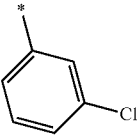 Br⁻ | 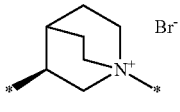 | acetonitrile | Method A: 1.46 min | 463 [M]⁺ | 0.012 |
| 28 | 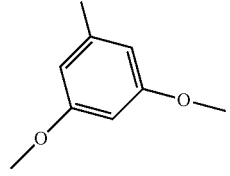 Br⁻ | 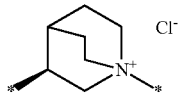 | acetonitrile | Method A: 1.56 min | 489 [M]⁺ | 0.080 |
| 29 | 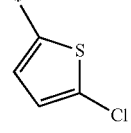 Cl⁻ | 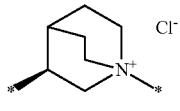 | acetonitrile | Method A: 1.36 min | 469 [M]⁺ | 0.029 |
| 30 | 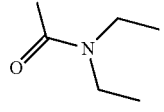 Cl⁻ | 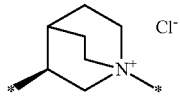 | acetonitrile | Method A: 1.07 min | 452 [M]⁺ | 0.035 |
| 31 | 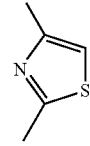 Cl⁻ | 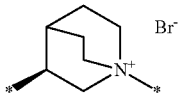 | acetonitrile | Method A: 1.10 min | 450 [M]⁺ | 0.054 |
| 32 | 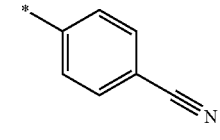 Br⁻ | 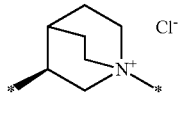 | acetonitrile | Method A: 1.16 min | 454 [M]⁺ | 0.202 |
| 33 | 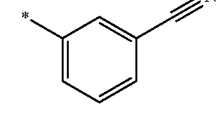 Cl⁻ | 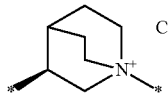 | acetonitrile | Method A: 1.14 min | 454 [M]⁺ | 0.038 |
| 34 | 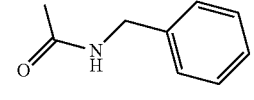 Cl⁻ | 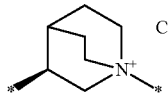 | acetonitrile | Method A: 1.48 min | 486 [M]⁺ | 0.007 |
| 35 | 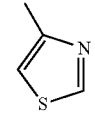 Cl⁻ | | acetonitrile | Method A: 1.01 min | 436 [M]⁺ | 0.150 |

TABLE 6-continued

| Example | L¹ and X⁻ | L³ | Solvent for titration | LC/MS (Method A): RT | m/z | ENaC IC50 (µM) |
|---|---|---|---|---|---|---|
| 36 | Cl⁻ | 3,5-difluorophenyl | acetonitrile | Method F: 4.95 min | 465 [M]⁺ | 0.030 |
| 37 | Cl⁻ | 2,3-dimethoxyphenyl | dichlorochloromethane | Method F: 5.19 min | 489 [M]⁺ | 0.034 |
| 38 | Cl⁻ | 3,4-difluorophenyl | Ethyl acetate/isopropanol | Method A: 1.50 min | 465 [M]⁺ | 0.023 |
| 39 | Br⁻ | benzyl ester | acetonitrile | Method F: 5.43 min | 487 [M]⁺ | 0.023 |
| 40 | Br⁻ | 4-(carboxymethyl)phenyl | acetonitrile | Method A: 1.31 min | 487 [M]⁺ | 0.625 |
| 41 | Br⁻ | benzoyl | dichlorochloromethane | Method F: 4.97 min | 457 [M]⁺ | 0.063 |
| 42 | Br⁻ | ethyl ester | isopropanol | Method A: 1.12 min | 425 [M]⁺ | 0.191 |
| 43 | Br⁻ | 4-methylphenyl | dichlorochloromethane | Method A: 1.51 min | 433 [M]⁺ | 0.014 |

TABLE 6-continued

| Example | L¹ and X⁻ | L³ | Solvent for titration | LC/MS (Method A): RT | m/z | ENaC IC50 (μM) |
|---|---|---|---|---|---|---|
| 44 | quinuclidinium, Cl⁻ | 4-chlorobenzyl-NHC(O)- | dichloromethane | Method A: 2.21 min | 520 [M]⁺ | 0.002 |
| 45 | quinuclidinium, Cl⁻ | pyridin-4-yl | Ethanol/diethyl ether | Method A: 1.02 min | 430 [M]⁺ | 0.279 |
| 46 | quinuclidinium, Br⁻ | 4-(tert-butoxycarbonyl)phenyl | acetonitrile/dichloromethane | Method A: 2.06 min | 529 [M]⁺ | 0.267 |
| 47 | quinuclidinium, Cl⁻ | 5-chloro-1,2,3-thiadiazol-4-yl | acetonitrile/dichloromethane | Method A: 1.04 min | 471 [M]⁺ | 0.226 |
| 48 | quinuclidinium, Br⁻ | 4-(trifluoromethylthio)phenyl | acetonitrile/dichloromethane | Method A: 2.04 min | 529 [M]⁺ | 0.023 |
| 49 | quinuclidinium, Br⁻ | isopropyl-NHC(O)- | dichloromethane | Method A: 1.11 min | 438 [M]⁺ | 0.029 |
| 50 | quinuclidinium, Cl⁻ | pyridin-3-yl | Ethanol/diethyl ether | Method A: 1.02 min | 430 [M]⁺ | 0.104 |
| 51 | quinuclidinium, Cl⁻ | 4-(trifluoromethoxy)phenyl | dichloromethane | Method F: 5.64 min | 513 [M]⁺ | 0.089 |

TABLE 6-continued

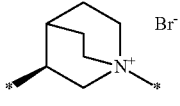

| Example | L¹ and X⁻ | L³ | Solvent for titration | LC/MS (Method A): RT | m/z | ENaC IC50 (μM) |
|---|---|---|---|---|---|---|
| 52 | 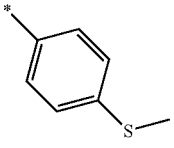 Br⁻ | 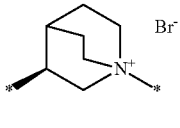 | dichloro-methane | Method A: 1.75 min | 475 [M]⁺ | 0.067 |
| 53 | 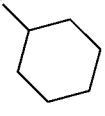 Br⁻ | 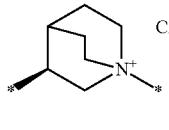 | acetonitrile | Method A: 1.42 min | 435 [M]⁺ | 0.070 |
| 54 | 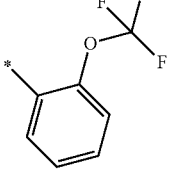 Cl⁻ | 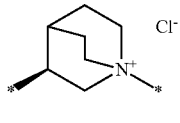 | acetonitrile | Method A: 1.75 min | 513 [M]⁺ | 0.069 |
| 55 | 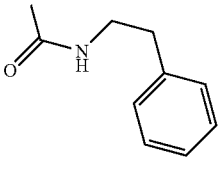 Cl⁻ | 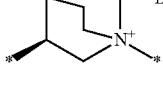 | dichloro-chloro-methane | Method F: 5.36 min | 500 [M | 0.001 |
| 56 | 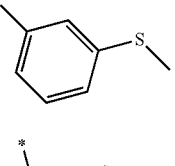 Br⁻ | 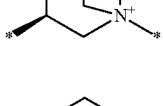 | acetonitrile | Method F: 5.28 min | 475 [M]⁺ | 0.012 |
| 57 | 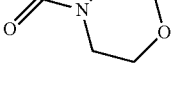 Br⁻ | 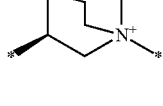 | acetonitrile/diethyl ether | Method F: 3.84 min | 466 [M]⁺ | 0.071 |
| 58 | 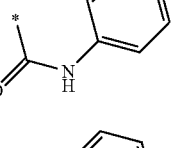 Cl⁻ | 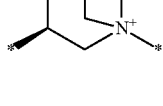 | dichloro-chloro-methane | Method A: 1.63 min | 472 [M]⁺ | 0.025 |
| 59 | 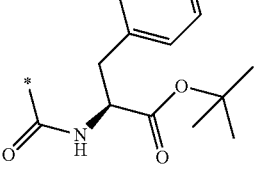 Cl⁻ | | acetone | Method F: 5.72 min | 600 [M]⁺ | 0.006 |

TABLE 6-continued

| Example | L¹ and X⁻ | L³ | Solvent for titration | LC/MS (Method A): RT | m/z | ENaC IC50 (μM) |
|---|---|---|---|---|---|---|
| 60 | Cl⁻ | | diethyl ether | Method F: 6.18 min | 600 [M]⁺ | 0.012 |
| 61 | Cl⁻ | | acetone | Method F: 5.35 min | 558 [M]⁺ | 0.002 |
| 62 | Br⁻ | | acetone/ methanol | Method A: 1.08 min | 542 [M]⁺ | 0.020 |
| 63 | Br⁻ | | acetonitrile | Method F: 4.89 min | 511 [M]⁺ | 0.030 |
| 64 | Br⁻ | | acetonitrile | Method F: 4.89 min | 551 [M]⁺ | 0.076 |
| 65 | Cl⁻ | | dichlorochloromethane | Method F: 5.40 min | 514 [M]⁺ | 0.002 |

TABLE 6-continued

[Structure shown: 3,5-diamino-6-chloro-pyrazine-2-carbonyl guanidine core with L¹, L³ substituents and X⁻ counterion]

| Example | L¹ and X⁻ | L³ | Solvent for titration | LC/MS (Method A): RT | m/z | ENaC IC50 (µM) |
|---|---|---|---|---|---|---|
| 66 | [3-substituted quinuclidinium], Br⁻ | [piperazinyl-pyrimidine carbonyl] | diethyl ether/acetonitrile | Method F: 5.10 min | 543 [M]⁺ | 0.022 |
| 67 | [3-substituted quinuclidinium], Cl⁻ | [piperidine-4-carboxylate tert-butyl ester carbonyl] | diethyl ether | Method F: 5.75 min | 564 [M]⁺ | 0.040 |

Example 68

(S)-1-(Bis-benzylcarbamoyl-methyl)-3-[N'-(3,5-diamino-6-chloro-pyrazine-2-carbonyl)-guanidino]-1-azonia-bicyclo[2.2.2]octane bromide

68

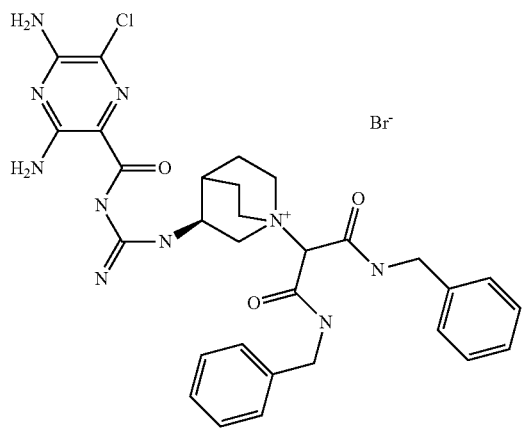

N-(S)-1-Aza-bicyclo[2.2.2]oct-3-yl-N'-(3,5-diamino-6-chloro-pyrazine-2-carbonyl)-guanidine (Intermediate 6, 80 mg, content ca. 95%, 0.22 mmol) and N,N'-dibenzyl-2-bromo-malonamide (Intermediate 12, 97 mg, 0.27 mmol) in DMF (1 mL) are stirred at r.t. for ca. 18 h. Acetonitrile (3 mL) is then added and the mixture kept at 4° C. for ca. 18 h. The resulting solid is collected by filtration and triturated with acetonitrile:diethyl ether (1:1, 3 mL), with acetonitrile (5 mL) and then with dichloromethane (3 mL). Drying under vacuum yields the title compound (46 mg).

LC/MS (Method F): RT=5.86 min, m/z=619 [M]⁺.
ENaC IC50 (µM): 0.008

The following compound is prepared analogously to Example 68:

Example 68.1

(S)-3-[N'-(3,5-Diamino-6-chloro-pyrazine-2-carbonyl)-guanidino]-1-(ethylcarbamoyl-phenyl-methyl)-1-azonia-bicyclo[2.2.2]octane bromide 68.1

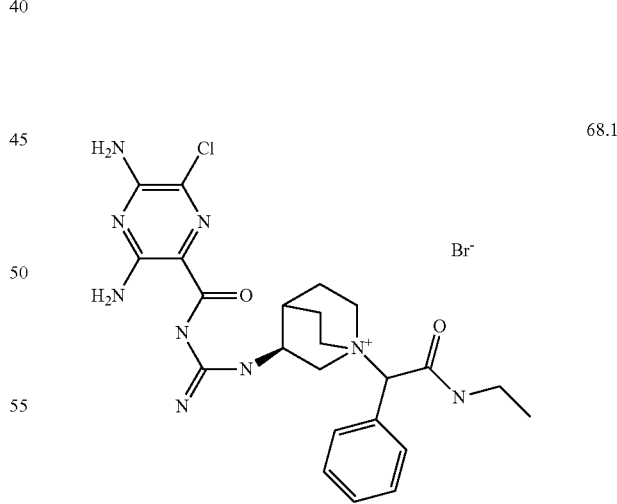

From N-(S)-1-Aza-bicyclo[2.2.2]oct-3-yl-N'-(3,5-diamino-6-chloro-pyrazine-2-carbonyl)-guanidine (Intermediate 6, 100 mg, content ca. 90%, 0.27 mmol) and 2-bromo-N-ethyl-2-phenyl-acetamide (Intermediate 13, content ca. 90%, 100 mg, 0.37 mmol) in DMF (1 mL). Yield: 25 mg
LC/MS (Method F): RT=5.86 min, m/z=619 [M]⁺.
ENaC IC50 (µM): 0.018

Example 69

(S)-3-[N'-(3,5-Diamino-6-chloro-pyrazine-2-carbo-nyl)-guanidino]-1-(3-methyl-but-2-enyl)-1-azoniabi-cyclo[2.2.2]octane chloride

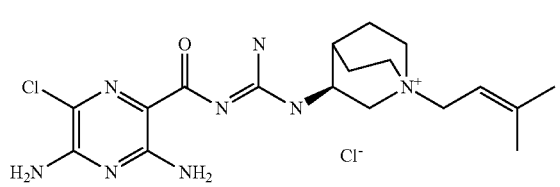

N-(S)-1-Aza-bicyclo[2.2.2]oct-3-yl-N'-(3,5-diamino-6-chloro-pyrazine-2-carbonyl)-guanidine (Intermediate 6, 125 mg, content ca. 87%, 0.32 mmol) and 1-chloro-3-methyl-2-butene (Aldrich, 0.040 mL, 0.35 mmol) in DMF (0.8 mL) are stirred at r.t. for ca. 18 h. Acetonitrile (1 mL) is added. After 1 h the solution is decanted from solids, volatiles evaporated under vacuum and the residue treated with acetonitrile. The resulting solid is collected and further purified by preparative HPLC (5 mM ammonium formate in $H_2O:CH_3CN$ gradient). The material thus obtained is treated with excess HCl in dioxane followed by evaporation. Finally, trituration with diethyl ether, filtration and drying under vacuum yields the title compound (22 mg).

LC/MS (Method A): RT=1.16, m/z=407 [M]$^+$.

ENaC IC50 (μM): 0.188.

Example 70

1-Benzyl-4-[N'-(3,5-diamino-6-chloro-pyrazine-2-carbonyl)-guanidino]-1-methyl-piperidinium chloride

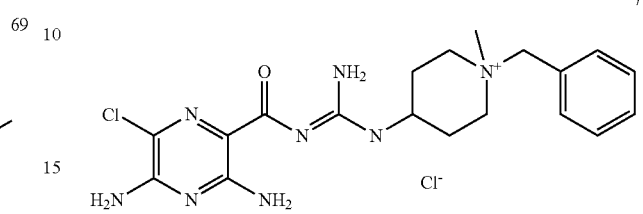

A mixture of 860 mg (1.5 mmol; content ca. 80%) 4-amino-1-benzyl-1-methyl-piperidinium bis trifluoroacetate (Intermediate 7.1) and 414 mg (1.5 mmol) 1-(3,5-Diamino-6-chloro-pyrazine-2-carbonyl)-2-methyl-isothiourea in 50 ml tetrahydrofuran and 50 ml methanol is stirred at 50° C. for overnight. Then the reaction mixture is concentrated under reduced pressure and the residue is purified by preparative reverse phase HPLC (gradient of acetonitrile and water+ 0.2% trifluoroacetic acid, 25° C.). Fractions containing the title compound were concentrated under reduced pressure, treated with excess HCl in methanol and evaporated again.

Yield: 480 mg

ESI mass spectrum: [M]$^+$=417

Retention time HPLC: 0.74 min (method D).

ENaC IC50 (μM): 0.106.

The following compounds are prepared accordingly from starting materials as indicated:

TABLE 7

| Example | $L^1$ and $X^-$ | $L^3$ | Starting material | LC/MS (Method A): RT | m/z | ENaC IC50 (μM) |
|---|---|---|---|---|---|---|
| 70.1 | piperidinium-N-methyl / trifluoroacetate | methyl 4-benzoate | 7 | Method C: 1.5 | 475 [M]$^+$ | 0.064 |
| 70.2 | piperidinium-N-ethyl / Cl$^-$ | phenyl | 7.2 | Method D: 0.76 | 431 [M]$^+$ | 0.052 |

TABLE 7-continued

| Example | L¹ and X⁻ | L³ | Starting material | LC/MS (Method A): RT | m/z | ENaC IC50 (μM) |
|---|---|---|---|---|---|---|
| 70.3 | 3-piperidinium, N-methyl, Cl⁻ | ethylcarbamoyl | 7.3 | Method D: 0.69 | 412 [M]⁺ | 0.26 |
| 70.4 | 3-piperidinium, N-methyl, Cl⁻ | N-(3-fluorophenyl)carbamoyl | 7.4 | Method D: 0.86, 0.89 (Isomers) | 478 [M]⁺ | 0.031 |
| 70.5 | 3-piperidinium, N-methyl, Cl⁻ | N-(4-chlorobenzyl)carbamoyl | 7.5 | Method D: 0.95, 0.97 (Isomers) | 508 [M]⁺ | 0.045 |
| 70.6 | 3-piperidinium, N-methyl, Cl⁻ | ethylcarbamoyl | 7.6 | Method D: 0.68, 0.70 (Isomers) | 412 [M]⁺ | 0.046 |
| 70.7 | 4-piperidinium, N-ethyl, Cl⁻ | N-(3-fluorophenyl)carbamoyl | 7.7 | Method D: 1.04 | 492 [M]⁺ | 0.031 |

Example 71

(S)-1-Benzyl-3-[N'-(3,5-diamino-6-chloro-pyrazine-2-carbonyl)-guanidino]-1-methyl-piperidinium chloride

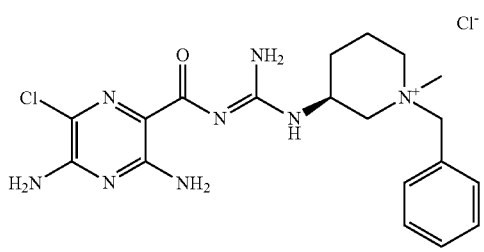

71

A) Synthesis of BOC Protected Intermediate 80 mg (0.1 mmol) (S)—N-(1-Benzyl-piperidin-3-yl)-N'-(3,5-diamino-6-chloro-pyrazine-2-carbonyl)-guanidine (Intermediate 9), 70 µl triethylamine and 90 mg BOC anhydride were dissolved in 3 ml THF and stirred over night. The organic layer is separated and concentrated under reduced pressure and the product is used in the next step without further purification

B) (S)-1-Benzyl-3-[N'-(3,5-diamino-6-chloro-pyrazine-2-carbonyl)-guanidino]-1-methyl-piperidinium chloride The above mentioned product is dissolved in 2 ml acetone and 50 µl methyl iodide is added. Then the mixture is stirred overnight at room temperature. The reaction mixture is concentrated under reduced pressure and 2 ml of a 50% solution of trifluoroacetic acid in dichloromethane is added and stirred for 2 h at room temperature. Then the mixture is coevaporated with methanolic hydrochloric acid. The residue is purified via preparative reverse phase HPLC (gradient of methanol and water+0.2% trifluoroacetic acid, 25° C.). Fractions containing the title compound were concentrated under reduced pressure and finally coevaporated with methanolic hydrochloric acid.

Yield: 82 mg.
ESI mass spectrum: $[M]^+$=417
Retention time HPLC: 0.74 min (method D)
ENaC IC50 (µM): 0.081.

The following compounds are prepared accordingly from starting materials as indicated:

TABLE 8

| Example | $L^1$ and $X^-$ | $L^3$ | Starting material | LC/MS (Method A): RT [min] | m/z | ENaC IC50 (µM) |
|---|---|---|---|---|---|---|
| 71.1 | [3-piperidinium, 1-methyl, Cl⁻] | [*C(=O)NH-CH2-C6H4-Cl] | 9.1 | Method D: 0.95 and 0.97 (Isomers) | 508 | 0.0306 |
| 71.2 | [3-pyrrolidinium, 1-methyl, Cl⁻] | [*phenyl] | 9.2 | Method D: 0.72 | 403 | 0.1127 |

Example 72

(S)-3-[N'-(3,5-Diamino-6-chloro-pyrazine-2-carbonyl)-guanidino]-1-(3-methoxycarbonyl-benzyl)-1-methyl-piperidinium chloride

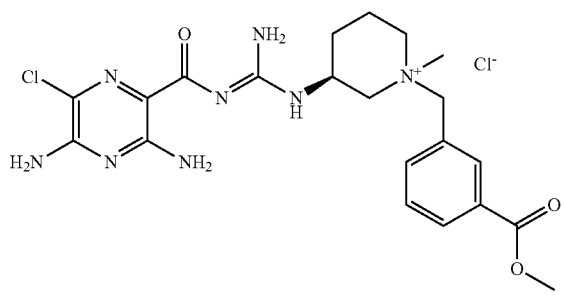

A mixture of 35 mg (0.066 mmol) (S)-3-{3-[N'-(3,5-Diamino-6-chloro-pyrazine-2-carbonyl)-guanidino]-piperidin-1-ylmethyl}-benzoic acid methyl ester (intermediate 10) and 100 µl (0.7 mmol) methyl iodide in 2 ml acetone/dimethylformamide (1:1) is stirred at room temperature overnight. Then the reaction mixture is concentrated under reduced pressure and the residue is purified by preparative reverse phase HPLC (gradient of methanol and water+0.2% trifluoroacetic acid, 25° C.). Fractions containing the title compound were concentrated under reduced pressure, treated with excess HCl in methanol and evaporated again.

Yield: 35 mg

ESI mass spectrum: $[M]^+=475$

Retention time HPLC: 0.79 min (method D).

ENaC IC50 (µM): 0.122.

The following compounds are prepared accordingly from starting materials as indicated:

TABLE 9

| Example | L¹ and X⁻ | L³ | Starting material | LC/MS (Method A): RT [min] | m/z [M]⁺ | ENaC IC50 (µM) |
|---|---|---|---|---|---|---|
| 72.1 | N-methylpiperidinium, Cl⁻ | N-methyl-N-phenylamide | 9.3 | Method E: 0.54 | 474 | 0.137 |
| 72.2 | N-methylpiperidinium, Cl⁻ | N-methyl-N-benzylamide | 9.4 | Method E: 0.57 | 488 | 0.076 |
| 72.3 | N-methylpiperidinium, Cl⁻ | 2-(methoxycarbonyl)phenylamide | 9.5 | Method D: 0.57 | 518 | 0.022 |

Example 73

(S)-1-[((S)-1-Carboxy-2-phenyl-ethylcarbamoyl)-methyl]-3-[N'-(3,5-diamino-6-chloro-pyrazine-2-carbonyl)-guanidino]-1-azonia-bicyclo[2.2.2]octane chloride hydrochloride

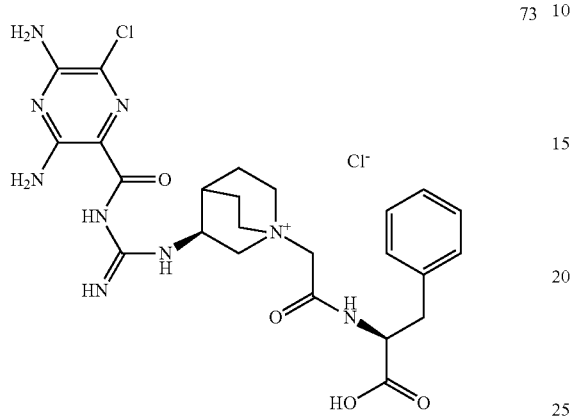

A mixture of 140 mg (0.22 mmol) (S)-1-[((S)-1-tert-butoxycarbonyl-2-phenyl-ethylcarbamoyl)-methyl]-3-[N'-(3,5-diamino-6-chloro-pyrazine-2-carbonyl)-guanidino]-1-azonia-bicyclo-[2.2.2]-octane chloride (Intermediate 59) and 6.2 mL (12.4 mmol) HCl (2 M) in diethyl ether is stirred overnight at room temperature. The resulting solid is collected by filtration and washed with diethyl ether. Recrystallization from acetone yields the title compound (78 mg).

LC/MS (Method A): RT 1.71 min, m/z=544 [M]+.

ENaC IC50 (μM): 0.004.

The following compounds are prepared analogously to Example 73:

Example 73.1

(S)-1-[((R)-1-Carboxy-2-phenyl-ethylcarbamoyl)-methyl]-3-[N'-(3,5-diamino-6-chloro-pyrazine-2-carbonyl)-guanidino]-1-azonia-bicyclo[2.2.2]octane; chloride hydrochloride

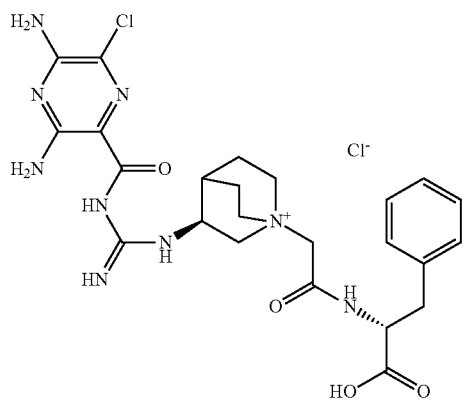

Starting from 180 mg (0.28 mmol) of (S)-1-[((R)-1-tert-butoxycarbonyl-2-phenyl-ethylcarbamoyl)-methyl]-3-[N'-(3,5-diamino-6-chloro-pyrazine-2-carbonyl)-guanidino]-1-azonia-bicyclo-[2.2.2]-octane chloride (Intermediate 60)

Yield: 110 mg

LC/MS (Method G): RT 6.43 min, m/z=544 [M]+.

ENaC IC50 (μM): 0.197.

Example 73.2

(S)-1-[2-(4-Carboxy-piperidin-1-yl)-2-oxo-ethyl]-3-[N'-(3,5-diamino-6-chloro-pyrazine-2-carbonyl)-guanidino]-1-azonia-bicyclo[2.2.2]octane chloride hydrochloride

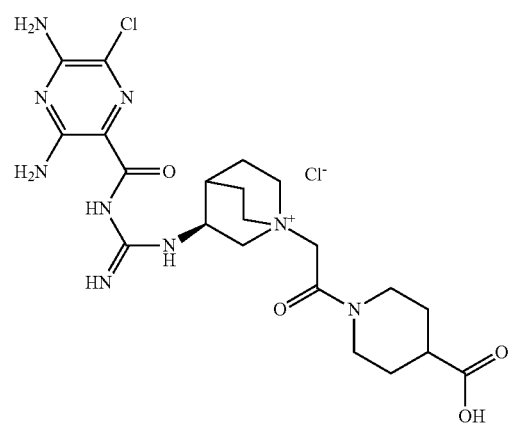

Starting from 120 mg (0.20 mmol) of (S)-1-[2-(4-tert-butoxycarbonyl-piperidin-1-yl)-2-oxo-ethyl]-3-[N'-(3,5-diamino-6-chloro-pyrazine-2-carbonyl)-guanidino]-1-azonia-bicyclo[2.2.2]octane; chloride (Intermediate 67).

Yield: 55 mg

LC/MS (Method A): RT 1.28 min, m/z=508 [M]+.

ENaC IC50 (μM): 0.269.

The compounds in Table 10 are obtained analogously to Example 14 by reaction of intermediate 6 and the appropriate alkylating agents, employing suitable solvents for trituration. The respective appropriate alkylating agents are prepared from bromoacetyl bromide and the corresponding primary amine.

TABLE 10

| Example | L¹ and X⁻ | L³ | Solvent for titration | LC/MS (Method A): RT | m/z | ENaC IC50 (µM) |
|---|---|---|---|---|---|---|
| 74 | (quinuclidinyl) Br⁻ | *C(O)NH-CH2-(4-phenyltetrahydropyran-4-yl) | acetonitrile, then CH₂Cl₂ | Method F: 5.12 min | 570 [M]⁺ | 0.015 |
| 75 | (quinuclidinyl) Br⁻ | *C(O)NH-(trans-4-phenylcyclohexyl) | acetonitrile, then CH₂Cl₂ | Method F: 5.99 min | 554 [M]⁺ | 0.022 |
| 76 | (quinuclidinyl) Br⁻ | *C(O)NH-CH2-(tetrahydropyran-4-yl) | acetonitrile/ Et₂O | Method F: 4.36 min | 494 [M]⁺ | 0.039 |
| 77 | (quinuclidinyl) HCOO⁻ | *C(O)NH-CH2CH2-(3-ethoxycarbonylphenyl) | acetonitrile/ tBuOMe, then acetone, then reverse phase HPLC (H₂O/ NH₄COOH/ acetonitrile) | Method F: 5.57 min | 572 [M]⁺ | 0.043 |

8. Analytical Methods and Preparative Chromatography

The HPLC retention times and mass spectroscopy data given are measured using the following methods:

Method A
Instrument: LC/MS ThermoFinnigan HPLC Surveyor DAD, LCQFleet Ion Trap
Column: Symmetry Shield RP8, 5 µm, 4.6×150 mm
Mobile phase: A=H2O 90%+CH3CN 10%+HCOOH 0.1%
B=CH3CN 90%+H2O 10%+HCOOH 0.1%
Time [min] % A % B Flow rate [mL/min]
0.00 95 5 1
1.50 95 5 1
11.05 5 95 1
13 5 95 1
13.03 95 5 1
15 95 5 1
Detection: UV 254 nm
Detection: Finnigan Fleet, Ion Trap
Ion source: ES+
Scan range: 100-900 amu Method B
Instrument: LC/MS ThermoFinnigan HPLC Surveyor DAD, MSQ single quadrupole
Column: Synergi Hydro RP80A, 4 µm, 4.6×100 mm
Mobile phase: A=H2O 90%+CH3CN 10%+NH4COOH 10 mM
B=CH3CN 90%+H2O 10%+NH4COOH 10 mM
Time [min]% A % B Flow rate [mL/min]
0.00 100 0 1.2
1.50 100 0 1.2
11.05 0 100 1.2
13 0 100 1.2
13.05 100 0 1.2
15 100 0 1.2
Detection: UV 254 nm
Detection: Finnigan MSQ, single quadrupole
Ion source: APCI+/APCIScan
range: 100-900 amu Method C
Instrument: Waters ZQ2000; Waters 1515 Pumpe, Waters PDA 996 Detektor, Waters 2747 Injektor
Column: X-terra™ MS C18 2.5 µm 4.6 mm×30 mm
Mobile phase: A water+0.1% formic acid
B acetonitril+0.1% formic acid
Stationäre Phase:
Säulentemperatur entspricht Umgebungstemperatur von ca. 25° C.
Diodenarraydetektion 210-420 nm
ESI positive and negative switchmode
Gradient:

| time in min | % A | % B | flow rate in ml/min |
| --- | --- | --- | --- |
| 0.00 | 95.0 | 5.0 | 1.00 |
| 0.10 | 95.0 | 5.0 | 1.00 |
| 3.10 | 2.0 | 98.0 | 1.00 |
| 4.50 | 2.0 | 98.0 | 1.00 |
| 5.00 | 95.0 | 5.0 | 1.00 |

Method D:
Instrument: Agilent 1200 with DA- and MS-Detector
Analytical column: Sunfire C18 (Waters technologies)
Sunfire C18, 3.0×30 mm, 2.5 µm column temperature 60° C.
Mobile phase A: H2O: trifluoroacetic acid 99.9:0.1
Mobile phase B: Methanol: 100
Gradient:

| time in min | % A | % B | flow rate in ml/min |
| --- | --- | --- | --- |
| 0.0 | 95 | 5 | 1.8 |
| 0.25 | 95 | 5 | 1.8 |
| 1.70 | 0 | 100 | 1.8 |
| 1.75 | 0 | 100 | 2.5 |
| 1.90 | 0 | 100 | 2.5 |

Method E
Instrument: Waters 1525 with DA- and MS-Detector
Analytical column: Sunfire C18, 4.6×30 mm, 2.5 µm (Waters technologies)
column temperature 60° C.
Mobile phase A: H2O: trifluoroacetic acid 99.9:0.1
Mobile phase B: Acetonitrile
Gradient:

| time in min | % A | % B | flow rate in ml/min |
| --- | --- | --- | --- |
| 0.0 | 97 | 3 | 4 |
| 0.15 | 97 | 3 | 3 |
| 2.15 | 0 | 100 | 3 |
| 2.20 | 0 | 100 | 4.5 |
| 2.40 | 0 | 100 | 4.5 |

Method F
Instrument: LC/MS ThermoFinnigan HPLC Surveyor DAD, LCQFleet Ion Trap
Column: Symmetry Shield RP8, 5 µm, 4.6×150 mm
Mobile phase: A=H2O 90%+CH3CN 10%+HCOOH 0.1%
B=CH3CN 90%+H2O 10%+HCOOH 0.1%

| time in min | % A | % B | flow rate in ml/min |
| --- | --- | --- | --- |
| 0.00 | 70 | 30 | 0.85 |
| 1.50 | 50 | 50 | 0.85 |
| 8.50 | 0 | 100 | 0.85 |
| 18.00 | 0 | 100 | 0.85 |
| 18.05 | 70 | 30 | 0.85 |
| 20 | 70 | 30 | 0.85 |

Detection: UV 254 nm
Detection: Finnigan Fleet, Ion Trap
Ion source: ES+
Scan range: 100-900 amu Method G
Instrument: LC/MS ThermoFinnigan HPLC Surveyor DAD, MSQ single quadrupole
Column: Synergi Hydro RP100A, 5 µm, 3.0×50 mm
Mobile phase: A=H2O 90%+CH3CN 10%+NH4COOH 10 mM
B=CH3CN 90%+H2O 10%+NH4COOH 10 mM

| time in min | % A | % B | flow rate in ml/min |
| --- | --- | --- | --- |
| 0.00 | 100 | 0 | 0.7 |
| 1.50 | 100 | 0 | 0.7 |
| 8.50 | 0 | 100 | 0.7 |
| 10.0 | 0 | 100 | 0.7 |
| 11.0 | 100 | 0 | 0.7 |
| 12.0 | 100 | 0 | 0.7 |

Detection: UV 254 nm
is Detection: Finnigan MSq single quadrupole
Ion source: APCI+/APCI−
Scan range: 100-900 amu
Method H

| Column: XBridge C18, 3 × 30 mm, 2.5 µm (Waters) | | | | |
|---|---|---|---|---|
| Gradient/Solvent Time [min] | % Sol [H2O, 0.1% NH3] | % Sol [Acetonitril] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method I

| Column: SunFire, 3 × 30 mm, 2.5 µm (Waters) | | | | |
|---|---|---|---|---|
| Gradient time [min] | % Sol [H2O, 0.1% TFA] | % Sol [ACN] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

The following abbreviations are used above and hereinafter:
DMF N,N-Dimethylformamide
r.t. ambient temperature (about 20° C.)

9. Pharmacological Test Method

Ussing Chamber: Mouse kidney M-1 cells were cultivated in DMEM containing 5% FCS and 5 µM dexamethasone for 10 to 12 days on polyester transwell filters. Filters were inserted into a teflon-coated well-plate which fit into the in-house ussing chamber system. Prior to measurement the medium of M-1 cells was replaced with Caco-2 transport buffer (Invitrogen, Germany). During measurements, the Ussing chamber temperature was kept at 37° C. Short circuit currents (I_sc) were measured in the voltage-clamp mode using an in-house built amplifier (Boehringer Ingelheim, Biberach) with the software package Lab View for data acquisition and analysis. The transepithelial electrical resistance (TEER) was determined by the application of voltage steps of ±5 mV every 5 sec. Compounds were administered at a final concentration of 3 µM or at increasing concentrations (1-3-10 µM) to the apical solution. At the end of each experiment the amiloride sensitive I_SC was measured by adding 3 µM amiloride to the apical compartment. Results are expressed as inhibition in percent of the amiloride effect or as IC50.

10. Indications

As has been found, the compounds of formula (I) are characterized by their wide range of applications in the therapeutic field. Particular mention should be made of those applications for which the compounds according to the invention of formula (I) are preferably suited on account of their pharmaceutical efficacy as ENaC inhibitors. Examples include respiratory diseases or complaints, or allergic diseases of the airways, Particular mention should be made of the prevention and treatment of diseases of the airways and of the lung which are accompanied by increased mucus production, inflammation and/or obstructive diseases of the airways. Examples include acute, allergic or chronic bronchitis, chronic obstructive bronchitis (COPD), coughing, pulmonary emphysema, allergic or non-allergic rhinitis or sinusitis, chronic rhinitis or sinusitis, asthma, alveolitis, Farmer's disease, hyperreactive airways, infectious bronchitis or pneumonitis, pediatric asthma, bronchiectases, pulmonary fibrosis, ARDS (acute adult respiratory distress syndrome), bronchial oedema, pulmonary oedema, bronchitis, pneumonia or interstitial pneumonia triggered by various causes, such as aspiration, inhalation of toxic gases, or bronchitis, pneumonia or interstitial pneumonia as a result of heart failure, irradiation, chemotherapy, cystic fibrosis or mucoviscidosis, or alpha1-antitrypsin deficiency.

Particularly preferably the present invention relates to the use of compounds of formula (I) for preparing a pharmaceutical composition for the treatment of inflammatory or obstructive diseases of the upper and lower respiratory tract including the lungs, such as for example allergic rhinitis, chronic rhinitis, bronchiectasis, cystic fibrosis, COPD, chronic bronchitis, chronic sinusitis, asthma, particularly COPD, chronic bronchitis, cystic fibrosis and asthma.

It is most preferable to use the compounds of formula (I) for the treatment of inflammatory and obstructive diseases such as COPD, chronic bronchitis, chronic sinusitis, asthma, cystic fibrosis, particularly COPD and cystic fibrosis.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

11. Combinations

The compounds of formula (I) may be used on their own or in conjunction with other active substances of (I) according to the invention. If desired the compounds of formula (I) may also be used in combination with other pharmacologically active substances.

Therefore the invention further relates to medicament combinations which preferably contain, besides one or more compounds of formula (I), as further active substances, one or more compounds selected from among the categories of further ENaC inhibitors, betamimetics, anticholinergics, corticosteroids, PDE4-inhibitors, LTD4-antagonists, EGFR-inhibitors, dopamine agonists, H1-antihistamines, PAF-antagonists, MAP-kinase inhibitors, MPR4-Inhibitors, iNOS-Inhibitors, SYK-Inhibitors, corrections of the cystic fibrosis transmembrane regulator (CFTR) and CFTR potentiators, or double or triple combinations thereof.

Examples of preferred betamimetics which may be mentioned include Albuterole, Arformoterole, Bambuterole, Bitolterole, Broxaterole, Carbuterole, Clenbuterole, Fenoterole, Formoterole, Hexoprenaline, Ibuterole, Isoetharine, Isoprenaline, Levosalbutamole, Mabuterole, Meluadrine, Metaproterenole, Milveterol, Orciprenaline, Pirbuterole, Procaterole, Reproterole, Rimiterole, Ritodrine, Salmefamole, Salmeterole, Soterenole, Sulphonterole, Terbutaline, Tiaramide, Tolubuterole, Zinterole, Nolomirole, and 1-(2-chloro-4-hydroxyphenyl)-t-butylaminoethanole, (−)-2-[7(S)-[2(R)-Hydroxy-2-(4-hydroxyphenyl)-ethylamino]-5,6,7,8-tetrahydro-2-naphthyloxy]-N,N-dimethylacetamide hydrochloride monohydrate,
3-(4-{6-[2-Hydroxy-2-(4-hydroxy-3-hydroxymethyl-phenyl)-ethylamino]-hexyloxy}-butyl)-benzyl-sulfonamide
5-[2-(5,6-Diethyl-indan-2-ylamino)-1-hydroxy-ethyl]-8-hydroxy-1H-quinoline-2-one
4-Hydroxy-7-[2-{[2-{[3-(2-phenylethoxy)propyl]sulphonyl}ethyl]-amino}ethyl]-2(3H)-benzothiazolone
1-(2-Fluoro-4-hydroxyphenyl)-2-[4-(1-benzimidazolyl)-2-methyl-2-butylamino]ethanole
1-[3-(4-Methoxybenzyl-amino)-4-hydroxyphenyl]-2-[4-(1-benzimidazolyl)-2-methyl-2-butylamino]ethanole
1-[2H-5-hydroxy-3-oxo-4H-1,4-benzoxazin-8-yl]-2-[3-(4-N,N-dimethylaminophenyl)-2-methyl-2-propylamino]ethanole
1-[2H-5-hydroxy-3-oxo-4H-1,4-benzoxazin-8-yl]-2-[3-(4-methoxyphenyl)-2-methyl-2-propylamino]ethanole
1-[2H-5-hydroxy-3-oxo-4H-1,4-benzoxazin-8-yl]-2-[3-(4-n-butyloxyphenyl)-2-methyl-2-propylamino]ethanole
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanole
5-Hydroxy-8-(1-hydroxy-2-isopropylaminobutyl)-2H-1,4-benzoxazin-3-(4H)-one
1-(4-Amino-3-chloro-5-trifluoromethylphenyl)-2-tert.-butylamino)ethanole
6-Hydroxy-8-{1-hydroxy-2-[2-(4-methoxy-phenyl)-1,1-dimethyl-ethylamino]-ethyl}-4H-benzo[1,4]oxazin-3-one
6-Hydroxy-8-{1-hydroxy-2-[2-(4-phenoxy-acetic acid ethylester)-1,1-dimethyl-ethylamino]-ethyl}-4H-benzo[1,4]oxazin-3-one
6-Hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-Dimethyl-2-(2,4,6-trimethylphenyl)-ethylamino]-1-hydroxy-ethyl}-6-hydroxy-4H-benzo[1,4]oxazin-3-one
6-Hydroxy-8-{1-hydroxy-2-[2-(4-hydroxy-phenyl)-1,1-dimethyl-ethylamino]-ethyl}-4H-benzo[1,4]oxazin-3-one
6-Hydroxy-8-{1-hydroxy-2-[2-(4-isopropyl-phenyl)-1,1dimethyl-ethylamino]-ethyl}-4H-benzo[1,4]oxazin-3-one
8-{2-[2-(4-Ethyl-phenyl)-1,1-dimethyl-ethylamino]-1-hydroxy-ethyl}-6-hydroxy-4H-benzo[1,4]oxazin-3-one
8-{2-[2-(4-Ethoxy-phenyl)-1,1-dimethyl-ethylamino]-1-hydroxy-ethyl}-6-hydroxy-4H-benzo[1,4]oxazin-3-one
4-(4-{2-[2-Hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-Difluor-phenyl)-1,1-dimethyl-ethylamino]-1-hydroxy-ethyl}-6-hydroxy-4H-benzo[1,4]oxazin-3-one
1-(4-Ethoxy-carbonylamino-3-cyano-5-fluorophenyl)-2-(tert.-butylamino)ethanole
N-[2-Hydroxy-5-(1-hydroxy-2-{2-[4-(2-hydroxy-2-phenyl-ethylamino)-phenyl]-ethylamino}-ethyl)-phenyl]-formamide
8-Hydroxy-5-(1-hydroxy-2-{2-[4-(6-methoxy-biphenyl-3-ylamino)-phenyl]-ethylamino}-ethyl)-1H-quinolin-2-one
8-Hydroxy-5-[1-hydroxy-2-(6-phenethylamino-hexylamino)-ethyl]-1H-quinolin-2-one
5-[2-(2-{4-[4-(2-Amino-2-methyl-propoxy)-phenylamino]-phenyl}-ethylamino)-1-hydroxy-ethyl]-8-hydroxy-1H-quinolin-2-one
[3-(4-{6-[2-Hydroxy-2-(4-hydroxy-3-hydroxymethyl-phenyl)-ethylamino]-hexyloxy}-butyl)-5-methyl-phenyl]-urea
4-(2-{6-[2-(2,6-Dichloro-benzyloxy)-ethoxy]-hexylamino}-1-hydroxy-ethyl)-2-hydroxymethyl-phenole
3-(4-{6-[2-Hydroxy-2-(4-hydroxy-3-hydroxymethyl-phenyl)-ethylamino]-hexyloxy}-butyl)-benzenesulfonamide
3-(3-{7-[2-Hydroxy-2-(4-hydroxy-3-hydroxymethyl-phenyl)-ethylamino]-heptyloxy}-propyl)-benzenesulfonamide
4-(2-{6-[4-(3-Cyclopentanesulfonyl-phenyl)-butoxy]-hexylamino}-1-hydroxy-ethyl)-2-hydroxymethyl-phenole
N-Adamantan-2-yl-2-(3-{2-[2-hydroxy-2-(4-hydroxy-3-hydroxymethyl-phenyl)-ethylamino]-propyl}-phenyl)-acetamide
(R,S)-4-(2-{[6-(2,2-Difluoro-4-phenylbutoxy)hexyl]amino}-1-hydroxy-ethyl)-2-(hydroxymethyl)phenole
(R,S)-4-(2-{[6-(2,2-Difluoro-2-phenylethoxy)hexyl]amino}-1-hydroxy-ethyl)-2-(hydroxymethyl)phenole
(R,S)-4-(2-{[4,4-Difluoro-6-(4-phenylbutoxy)hexyl]amino}-1-hydroxy-ethyl)-2-(hydroxy-methyl)phenole
(R,S)-4-(2-{[6-(4,4-Difluoro-4-phenylbutoxy)hexyl]amino}-1-hydroxy-ethyl)-2-(hydroxymethyl)phenole
(R,S)-5-(2-{[6-(2,2-Difluoro-2-phenylethoxy)hexyl]amino}-1-hydroxy-ethyl)-8-hydroxyquinolin-2(1H)-one
(R,S)-[2-({6-[2,2-Difluoro-2-(3-methylphenyl)ethoxy]hexyl}amino)-1-hydroxyethyl]-2-(hydroxymethyl)phenole
4-(1R)-2-{[6-(2,2-Difluoro-2-phenylethoxy)hexyl]amino}-1-hydroxyethyl)-2-(hydroxymethyl)phenol
(R,S)-2-(Hydroxymethyl)-4-(1-hydroxy-2-{[4,4,515-tetrafluoro-6-(3-phenylpropoxy)-hexyl]amino}ethyl)phenole
(R,S)-[5-(2-{[6-(2,2-Difluoro-2-phenylethoxy)hexyl]amino}-1-hydroxy-ethyl)-2-hydroxy-phenyl]formamide
(R,S)-4-[2-({6-[2-(3-Bromophenyl)-2,2-difluoroethoxy]hexyl}amino)-1-hydroxyethyl]-2-(hydroxymethyl)phenole
(R,S)-N-[3-(1,1-Difluoro-2-{[6-({2-hydroxy-2-[4-hydroxy-3-(hydroxymethyl)phenyl]-ethyl}amino)hexyl]oxy}ethyl)phenyl]urea
3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione
(R,S)-4-[2-({6-[2,2-difluoro-2-(3-methoxyphenyl)ethoxy]hexyl}amino)-1-hydroxyethyl]-2-(hydroxymethyl)phenole
5-((1R)-2-{[6-(2,2-difluoro-2-phenylethoxy)hexyl]amino}-1-hydroxyethyl)-8-hydroxyquinolin-2(1H)-one
4-((1R)-2-{[4,4-Difluoro-6-(4-phenylbutoxy)hexyl]amino}-1-hydroxy-ethyl)-2-(hydroxymethyl)phenole
(R,S)-4-(2-{[6-(3,3-Difluoro-3-phenylpropoxy)hexyl]amino}-1-hydroxy-ethyl)-2-(hydroxymethyl)phenole
(R,S)-(2-{[6-(2,2-Difluoro-2-phenylethoxy)-4,4-difluorohexyl]amino}-1-hydroxyethyl)-2-(hydroxymethyl)phenole
(R,S)-4-(2-{[6-(2,2-difluoro-3-phenylpropoxy)hexyl]amino}-1-hydroxy ethyl)-2-(hydroxy-methyl)phenole
3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide
N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide
7-[2-(2-{3-[2-(2-Chloro-phenyl)-ethylamino]-propylsulfanyl}-ethylamino)-1-hydroxy-ethyl]-4-hydroxy-3H-benzothiazol-2-one and 7-[(1R)-2-(2-{3-[2-(2-Chloro-phenyl)-ethylamino]-propylsulfanyl}-ethylamino)-1-hydroxy-ethyl]-4-hydroxy-3H-benzothiazol-2-one
optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred anticholinergics which may be mentioned include Tiotropium salts, preferred the bromide salt, Oxitropium salts, preferred the bromide salt, Flutropium salts, preferred the bromide salt, Ipratropium salts, preferred the bromide salt, Aclidinium salts, preferred the bromide salt, Glycopyrronium salts, preferred the bromide salt, Trospium salts, preferred the chloride salt, Tolterodin. From the above mentioned salts the pharmacologically active part is the cation, possible anions are chloride, bromide, iodide, sulfate, phosphate, methansulfonate, nitrate, maleate, acetate, citrate, fumarate, tartrate, oxalate, succinate, benzoate or p-toluenesulfonate. Further examples of preferred anticholinergics are selected from among 2,2-Diphenylpropionic acid tropenole ester-methobromide
2,2-Diphenylpropionic acid scopine ester-methobromide
2-Fluor-2,2-Diphenylacetic acid scopine ester-methobromide
2-Fluor-2,2-Diphenylacetic acid tropenole ester-methobromide
3,3',4,4'-Tetrafluorbenzil acid tropenole ester-methobromide
3,3',4,4'-Tetrafluorbenzil acid scopine ester-methobromide
4,4'-Difluorbenzil acid tropenole ester-methobromide
4,4'-Difluorbenzil acid scopine ester-methobromide
3,3'-Difluorbenzil acid tropenole ester-methobromide
3,3'-Difluorbenzil acid scopine ester-methobromide
9-Hydroxy-fluorene-9-carbon acid tropenole ester-methobromide
9-Fluor-fluorene-9-carbon acid tropenole ester-methobromide
9-Hydroxy-fluorene-9-carbon acid scopine ester-methobromide
9-Fluor-fluorene-9-carbon acid scopine ester methobromide
9-Methyl-fluorene-9-carbon acid tropenole estermethobromide
9-Methyl-fluorene-9-carbon acid scopine estermethobromide
Benzil acid cyclopropyl tropine ester-methobromide
2,2-Diphenylpropionic acid cyclopropyl tropine ester-methobromide
9-Hydroxy-xanthene-9-carbon acid cyclopropyl tropine ester-methobromide
9-Methyl-fluorene-9-carbon acid cyclopropyl tropine ester-methobromide
9-Methyl-xanthene-9-carbon acid cyclopropyl tropine ester-methobromide
9-Hydroxy-fluorene-9-carbon acid cyclopropyl tropine ester-methobromide
4,4'-Difluorbenzil acid methylester cyclopropyl tropine ester-methobromide
9-Hydroxy-xanthene-9-carbon acid tropenole ester-methobromide
9-Hydroxy-xanthene-9-carbon acid scopine ester methobromide
9-Methyl-xanthene-9-carbon acid tropenole ester-methobromide
9-Methyl-xanthene-9-carbon acid scopine estermethobromide
9-Ethyl-xanthene-9-carbon acid tropenole ester methobromide
9-Difluormethyl-xanthene-9-carbon acid tropenole ester methobromide
9-Hydroxymethyl-xanthene-9-carbon acid scopine ester-methobromide.

Examples of preferred corticosteroids which may be mentioned include Beclomethasone, Betamethasone, Budesonide, Butixocorte, Ciclesonide, Deflazacorte, Dexamethasone, Etiprednole, Flunisolide, Fluticasone, Loteprednole, Mometasone, Prednisolone, Prednisone, Rofleponide, Triamcinolone, Tipredane, and {20R-16alpha, 17alpha-[butylidenebis(oxy)]-6alpha,9alpha-difluoro-11beta-hydroxy-17beta-(methylthio)androsta-4-en-3-one},
9-fluoro-11beta, 17,21-trihydroxy-16alpha-methylpregna-1,4-diene-3,20-dione 21-cyclohexanecarboxylate 17-cyclopropanecarboxylate,
16,17-butylidene dioxy-6,9-difluoro-11-hydroxy-17-(methylthio)androst-4-en-3-one
Flunisolide-21-[4'-(nitrooxymethyl)benzoate]
6,9-Difluoro-17-[(2-furanylcarbonyl)oxy]-11-hydroxy-16-methyl-3-oxo-androsta-1,4-dien-17-carbothion acid (S)-fluoromethylester,
6,9-Difluoro-11-hydroxy-16-methyl-3-oxo-17-propionyloxy-androsta-1,4-dien-17-carbothion acid (S)-(2-oxo-tetrahydro-furan-3S-yl)ester, and
6alpha,9alpha-difluoro-11beta-hydroxy-16alpha-methyl-3-oxo-17alpha-(2,2,3,3-tertamethylcyclopropylcarbonyl)oxy-androsta-1,4-diene-17beta-carboxylic acid cyanomethyl ester optionally in racemic form, as enantiomers, diastereomers or as pharmacologically acceptable salts, solvates or hydrates. Examples for preferred salts and derivatives are alkali salts, i.e. sodium or potassium salts, sulfobenzoates, phosphates, isonicotinates, acetates, dichloroacetates, propionates, dihydrogenphosphates, palmitates, pivalates or furoates.

Examples of preferred PDE4-inhibitors which may be mentioned include Enprofylline, Theophylline, Roflumilaste, Ariflo (Cilomilaste), Tofimilaste, Pumafentrine, Lirimilaste, Apremilaste, Arofylline, Atizorame, Oglemilastum, Tetomilaste and 5-[(N-(2,5-dichloro-3-pyridinyl)-carboxamide]-8-methoxy-quinoline
5-[N-(3,5-dichloro-1-oxido-4-pyridinyl)-carboxamide]-8-methoxy-2-(trifluoromethyl)-quinoline
N-(3,5-dichloropyrid-4-yl)-[1-(4-fluorobenzyl)-5-hydroxy-indole-3-yl]glyoxyl acid amide), 9-[(2-fluorophenyl)methyl]-N-methyl-2-(trifluoromethyl)-9H-purine-6-amine
4-[(2R)-2-[3-(cyclopentyloxy)-4-methoxyphenyl]-2-phenylethyl]-pyridine,
N-[(3R)-3,4,6,7-tetrahydro-9-methyl-4-oxo-1-phenylpyrrolo[3,2,1-jk][1,4]benzodiazepin-3-yl]-4-Pyridinecarboxamide,
4-[6,7-diethoxy-2,3-bis(hydroxymethyl)-1-naphthalenyl]-1-(2-methoxyethyl)-2(1H)-pyridinone
2-[4-[6,7-diethoxy-2,3-bis(hydroxymethyl)-1-naphthalenyl]-2-pyridinyl]-4-(3-pyridinyl)-1(2H)-Phthalazinone,
(3-(3-cyclopenyloxy-4-methoxybenzyl)-6-ethylamino-8-isopropyl-3H-purine,
beta-[3-(cyclopentyloxy)-4-methoxyphenyl]-1,3-dihydro-1,3-dioxo-2H-isoindole-2-propanamide,
9-ethyl-2-methoxy-7-methyl-5-propyl-imidazo[1,5-a]pyrido[3,2-e]pyrazin-6(5H)-one
5-[3-(cyclopentyloxy)-4-methoxyphenyl]-3-[(3-methylphenyl)methyl](3S,5S)-2-piperidinone,
4-[1-[3,4-bis(difluoromethoxy)phenyl]-2-(3-methyl-1-oxido-4-pyridinyl)ethyl]-alpha,alpha-bis(trifluoromethyl)-Benzenemethanol
N-(3,5-Dichloro-1-oxo-pyridine-4-yl)-4-difluoromethoxy-3-cyclopropylmethoxybenzamide (−)p-[(4aR*,10bS*)-9-Ethoxy-1,2,3,4,4a,10b-hexahydro-8-methoxy-2-methylbenzo[s][1,6]naphthyridin-6-yl]-N,N-diisopropylbenzamide (R)-(+)-1-(4-Bromobenzyl)-4-[(3-cyclopentyloxy)-4-methoxyphenyl]-2-pyrrolidone 3-(Cyclopentyloxy-4-methoxyphenyl)-1-(4-N'-[N-2-cyano-5-methyl-isothioureido]benzyl)-2-pyrrolidone cis[4-Cyano-4-(3-cyclopentyloxy-4-methoxyphenyl)cyclohexan-1-carbon acid]

2-carbomethoxy-4-cyano-4-(3-cyclopropylmethoxy-4-difluoromethoxyphenyl)cyclohexan-1-one cis[4-Cyano-4-(3-cyclopropylmethoxy-4-difluoromethoxyphenyl)cyclohexan-1-ol]

(R)-(+)-Ethyl[4-(3-cyclopentyloxy-4-methoxyphenyl)pyrrolidine-2-yliden]acetate (S)-(−)-Ethyl[4-(3-cyclopentyloxy-4-methoxyphenyl)pyrrolidine-2-yliden]acetate 9-Cyclopentyl-5,6-dihydro-7-ethyl-3-(2-thienyl)-9H-pyrazolo[3,4-c]-1,2,4-triazolo[4,3-a]pyridine 9-Cyclopentyl-5,6-dihydro-7-ethyl-3-(tert-butyl)-9H-pyrazolo[3,4-c]-1,2,4-triazolo[4,3-a]pyridine optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred LTD4-antagonists which may be mentioned include Montelukast, Pranlukast, Zafirlukast, Masikulast, L-733321 (see compound 2ab of D. Guay et al, Bioorg. Med. Chem. Lett. 8 (1998) 453-458) and (E)-8-[2-[4-[4-(4-Fluorophenyl)butoxy]phenyl]ethenyl]-2-(1H-tetrazole-5-yl)-4H-1-benzopyran-4-one (MEN-91507)

4-[6-Acetyl-3-[3-(4-acetyl-3-hydroxy-2-propylphenylthio)propoxy]-2-propylphenoxy]-butyric acid (MN-001)

1-(((R)-(3-(2-(6,7-Difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-Dichlorothieno[3,2-b]pyridin-5-yl)-(E)-ethenyl)phenyl)-3-(2-(1-hydroxy-1-methylethyl)phenyl)propyl)thio)methyl)cyclopropane acetic acid

[2-[[2-(4-tert-Butyl-2-thiazolyl)-5-benzofuranyl]oxymethyl]phenyl]acetic acid optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate. Further examples for optionally preferred salts and derivatives are alkali salts, i.e. sodium or potassium salts, sulfobenzoates, phosphates, isonicotinates, acetates, propionates, dihydrogenphosphates, palmitates, pivalates or furoates.

Examples of preferred EGFR-inhibitors which may be mentioned include Cetuximab, Trastuzumab, Panitumumab Gefitinib, Canertinib, Erlotinib, Mab ICR-62 and 4-[(3-Chlor-4-fluorphenyl)amino]-6-{[4-(morpholine-4-yl)-1-oxo-2-butene-1-yl]amino}-7-cyclopropylmethoxy-quinazoline 4-[(3-Chlor-4-fluorphenyl)amino]-6-{[4-(N,N-diethylamino)-1-oxo-2-butene-1-yl]amino}-7-cyclopropylmethoxy-quinazoline 4-[(3-Chlor-4-fluorphenyl)amino]-6-{[4-(N,N-dimethylamino)-1-oxo-2-butene-1-yl]amino}-7-cyclopropylmethoxy-quinazoline 4-[(R)-(1-Phenyl-ethyl)amino]-6-{[4-(morpholine-4-yl)-1-oxo-2-butene-1-yl]amino}-7-cyclopentyloxy-quinazoline 4-[(3-Chlor-4-fluor-phenyl)amino]-6-{[4-((R)-6-methyl-2-oxo-morpholine-4-yl)-1-oxo-2-butene-1-yl]amino}-7-cyclopropylmethoxy-quinazoline 4-[(3-Chlor-4-fluor-phenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline 4-[(3-Chlor-4-fluor-phenyl)amino]-6-{[4-((R)-2-methoxymethyl-6-oxo-morpholine-4-yl)-1-oxo-2-butene-1-yl]amino}-7-cyclopropylmethoxy-quinazoline 4-[(3-Chlor-4-fluor-phenyl)amino]-6-[2-((S)-6-methyl-2-oxo-morpholine-4-yl)-ethoxy]-7-methoxy-quinazoline 4-[(3-Chlor-4-fluorphenyl)amino]-6-({4-[N-(2-methoxy-ethyl)-N-methyl-amino]-1-oxo-2-butene-1-yl}amino)-7-cyclopropylmethoxy-quinazoline 4-[(3-Chlor-4-fluorphenyl)amino]-6-{[4-(N,N-dimethylamino)-1-oxo-2-butene-1-yl]amino}-7-cyclopentyloxy-quinazoline 4-[(R)-(1-Phenyl-ethyl)amino]-6-{[4-(N,N-bis-(2-methoxy-ethyl)-amino)-1-oxo-2-butene-1-yl]amino}-7-cyclopropylmethoxy-quinazoline 4-[(R)-(1-Phenyl-ethyl)amino]-6-({4-[N-(2-methoxy-ethyl)-N-ethyl-amino]-1-oxo-2-butene-1-yl}amino)-7-cyclopropylmethoxy-quinazoline 4-[(R)-(1-Phenyl-ethyl)amino]-6-({4-[N-(2-methoxy-ethyl)-N-methyl-amino]-1-oxo-2-butene-1-yl}amino)-7-cyclopropylmethoxy-quinazoline 4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline 4-[(3-Chlor-4-fluorphenyl)amino]-6-{[4-(N,N-dimethylamino)-1-oxo-2-butene-1-yl]amino}-7-((R)-tetrahydrofuran-3-yloxy)-quinazoline 4-[(3-Chlor-4-fluorphenyl)amino]-6-{[4-(N,N-dimethylamino)-1-oxo-2-butene-1-yl]amino}-7-((S)-tetrahydrofuran-3-yloxy)-quinazoline 4-[(3-Chlor-4-fluorphenyl)amino]-6-({4-[N-(2-methoxy-ethyl)-N-methyl-amino]-1-oxo-2-butene-1-yl}amino)-7-cyclopentyloxy-quinazoline 4-[(3-Chlor-4-fluorphenyl)amino]-6-{[4-(N-cyclopropyl-N-methyl-amino)-1-oxo-2-butene-1-yl]amino}-7-cyclopentyloxy-quinazoline 4-[(3-Chlor-4-fluorphenyl)amino]-6-{[4-(N,N-dimethylamino)-1-oxo-2-butene-1-yl]amino}-7-[(R)-(tetrahydrofuran-2-yl)methoxy]-quinazoline 4-[(3-Chlor-4-fluorphenyl)amino]-6-{[4-(N,N-dimethylamino)-1-oxo-2-butene-1-yl]amino}-7-[(S)-(tetrahydrofuran-2-yl)methoxy]-quinazoline 4-[(3-Ethinyl-phenyl)amino]-6,7-bis-(2-methoxy-ethoxy)-quinazoline 4-[(3-Chlor-4-fluorphenyl)amino]-7-[3-(morpholine-4-yl)-propyloxy]-6-[(vinylcarbonyl)amino]-quinazoline 4-[(R)-(1-Phenyl-ethyl)amino]-6-(4-hydroxy-phenyl)-7H-pyrrolo[2,3-d]pyrimidine 3-Cyano-4-[(3-chlor-4-fluorphenyl)amino]-6-{[4-(N,N-dimethylamino)-1-oxo-2-butene-1-yl]amino}-7-ethoxy-quinoline 4-{[3-Chlor-4-(3-fluor-benzyloxy)-phenyl]amino}-6-(5-{[(2-methansulfonyl-ethyl)amino]methyl}-furan-2-yl)quinazoline 4-[(R)-(1-Phenyl-ethyl)amino]-6-{[4-((R)-6-methyl-2-oxo-morpholine-4-yl)-1-oxo-2-butene-1-yl]amino}-7-methoxy-quinazoline 4-[(3-Chlor-4-fluorphenyl)amino]-6-{[4-(morpholine-4-yl)-1-oxo-2-buten-1-yl]amino}-7-[(tetrahydrofuran-2-yl)methoxy]-quinazoline 4-[(3-Chlor-4-fluorphenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-Ethinyl-phenyl)amino]-6-{[4-(5,5-dimethyl-2-oxo-morpholine-4-yl)-1-oxo-2-buten-1-yl]amino}-quinazoline 4-[(3-Chlor-4-fluor-phenyl)amino]-6-[2-(2,2-dimethyl-6-oxo-morpholine-4-yl)-ethoxy]-7-methoxy-quinazoline 4-[(3-Chlor-4-fluor-phenyl)amino]-6-[2-(2,2-dimethyl-6-oxo-morpholine-4-yl)-ethoxy]-7-[(R)-(tetrahydrofuran-2-yl)methoxy]-quinazoline 4-[(3-Chlor-4-fluor-phenyl)amino]-7-[2-(2,2-dimethyl-6-oxo-morpholine-4-yl)-ethoxy]-6-[(S)-(tetrahydrofuran-2-yl)methoxy]-quinazoline 4-[(3-Chlor-4-fluor-phenyl)amino]-6-{2-[4-(2-oxo-morpholine-4-yl)-piperidin-1-yl]-ethoxy}-7-methoxy-quinazoline 4-[(3-Chlor-4-fluor-phenyl)amino]-6-[1-(tert.-butyloxycarbonyl)-piperidine-4-yloxy]-7-methoxy-quinazoline 4-[(3-Chlor-4-fluor-phenyl)amino]-6-(trans-4-amino-cyclohexane-1-yloxy)-7-methoxy-quinazoline 4-[(3-Chlor-4-fluor-phenyl)amino]-6-(trans-4-methansulfonylamino-cyclohexane-1-yloxy)-7-methoxy-quinazoline 4-[(3-Chlor-4-fluor-phenyl)amino]-6-(tetrahydropyran-3-yloxy)-7-methoxy-quinazoline 4-[(3-Chlor-4-fluor-phenyl)amino]-6-(1-methyl-piperidine-4-yloxy)-7-methoxy-quinazoline 4-[(3-Chlor-4-fluor-phenyl)amino]-6-{1-[(morpholine-4-yl)carbonyl]-piperidine-4-yloxy}-7-methoxy-quinazoline 4-[(3-Chlor-4-fluor-phenyl)amino]-6-{1-[(methoxymethyl)carbonyl]-piperidine-4-yloxy}-7-methoxy-quinazoline 4-[(3-Chlor-4-fluor-phenyl)amino]-6-(piperidine-3-yloxy)-7-methoxy-quinazoline 4-[(3-Chlor-4-fluor-phenyl)amino]-6-[1-(2-acetylamino-ethyl)-piperidine-4-yloxy]-7-methoxy-quinazoline 4-[(3-Chlor-4-fluor-phenyl)amino]-6-(tetrahydropyran-4-yloxy)-7-ethoxy-quinazoline 4-[(3-Chlor-4-fluor-phenyl)amino]-6-((S)-tetrahydrofuran-3-yloxy)-7-hydroxy-quinazoline 4-[(3-Chlor-4-fluor-phenyl)amino]-6-(tetrahydropyran-4-yloxy)-7-(2-methoxy-ethoxy)-quinazoline 4-[(3-Chlor-4-fluor-phenyl)amino]-6-{trans-4-[(dimethylamino)sulfonylamino]-cyclohexane-1-yloxy}-7-methoxy-quinazoline 4-[(3-Chlor-4-fluor-phenyl)amino]-6-{trans-4-[(morpholine-4-yl)carbonylamino]-cyclohexane-1-yloxy}-7-methoxy-quinazoline 4-[(3-Chlor-4-fluor-phenyl)amino]-6-{trans-4-[(morpholine-4-yl)sulfonylamino]-cyclohexane-1-yloxy}-7-methoxy-quinazoline 4-[(3-Chlor-4-fluor-phenyl)amino]-6-(tetrahydropyran-4-yloxy)-7-(2-acetylamino-ethoxy)-quinazoline 4-[(3-Chlor-4-fluor-phenyl)amino]-6-(tetrahydropyran-4-yloxy)-7-(2-methansulfonylamino-ethoxy)-quinazoline 4-[(3-Chlor-4-fluor-phenyl)amino]-6-{1-[(piperidine-1-yl)carbonyl]-piperidine-4-yloxy}-7-methoxy-quinazoline 4-[(3-Chlor-4-fluor-phenyl)amino]-6-(1-aminocarbonylmethyl-piperidine-4-yloxy)-7-methoxy-quinazoline 4-[(3-Chlor-4-fluor-phenyl)amino]-6-(cis-4-{N-[(tetrahydropyran-4-yl)carbonyl]-N-methyl-amino}-cyclohexane-1-yloxy)-7-methoxy quinazoline 4-[(3-Chlor-4-fluor-phenyl)amino]-6-(cis-4-{N-[(morpholine-4-yl)carbonyl]-N-methyl-amino}-cyclohexane-1-yloxy)-7-methoxy-quinazoline 4-[(3-Chlor-4-fluor-phenyl)amino]-6-(cis-4-{N-[(morpholine-4-yl)sulfonyl]-N-methyl-amino}-cyclohexane-1-yloxy)-7-methoxy-quinazoline 4-[(3-Chlor-4-fluor-phenyl)amino]-6-(trans-4-ethansulfonylamino-cyclohexane-1-yloxy)-7-methoxy-quinazoline 4-[(3-Chlor-4-fluor-phenyl)amino]-6-(1-methansulfonyl-piperidine-4-yloxy)-7-ethoxy-quinazoline 4-[(3-Chlor-4-fluor-phenyl)amino]-6-(1-methansulfonyl-piperidine-4-yloxy)-7-(2-methoxy-ethoxy)-quinazoline 4-[(3-Chlor-4-fluor-phenyl)amino]-6-[1-(2-methoxy-acetyl)-piperidine-4-yloxy]-7-(2-methoxy-ethoxy)-quinazoline 4-[(3-Chlor-4-fluor-phenyl)amino]-6-(cis-4-acetylamino-cyclohexane-1-yloxy)-7-methoxy-quinazoline 4-[(3-Ethinyl-phenyl)amino]-6-[1-(tert-butyloxycarbonyl)-piperidine-4-yloxy]-7-methoxy-quinazoline 4-[(3-Ethinyl-phenyl)amino]-6-(tetrahydropyran-4-yloxy]-7-methoxy-quinazoline 4-[(3-Chlor-4-fluor-phenyl)amino]-6-(cis-4-{N-[(piperidine-1-yl)carbonyl]-N-methyl-amino}-cyclohexane-1-yloxy)-7-methoxy-quinazoline 4-[(3-Chlor-4-fluor-phenyl)amino]-6-(cis-4-{N-[(4-methyl-piperazine-1-yl)carbonyl]-N-methyl-amino}-cyclohexane-1-yloxy)-7-methoxy-quinazoline 4-[(3-Chlor-4-fluor-phenyl)amino]-6-{cis-4-[(morpholine-4-yl)carbonylamino]-cyclohexane-1-yloxy}-7-methoxy-quinazoline 4-[(3-Chlor-4-fluor-phenyl)amino]-6-{1-[2-(2-oxopyrrolidine-1-yl)ethyl]-piperidine-4-yloxy}-7-methoxy-quinazoline 4-[(3-Chlor-4-fluor-phenyl)amino]-6-{1-[(morpholine-4-yl)carbonyl]-piperidine-4-yloxy}-7-(2-methoxy-ethoxy)-quinazoline 4-[(3-Ethinyl-phenyl)amino]-6-(1-acetyl-piperidine-4-yloxy)-7-methoxy-quinazoline 4-[(3-Ethinyl-phenyl)amino]-6-(1-methyl-piperidine-4-yloxy)-7-methoxy-quinazoline 4-[(3-Ethinyl-phenyl)amino]-6-(1-methansulfonyl-piperidine-4-yloxy)-7-methoxy-quinazoline 4-[(3-Chlor-4-fluor-phenyl)amino]-6-(1-methyl-piperidine-4-yloxy)-7(2-methoxy-ethoxy)-quinazoline 4-[(3-Chlor-4-fluor-phenyl)amino]-6-(1-isopropyloxycarbonyl-piperidine-4-yloxy)-7-methoxy-quinazoline 4-[(3-Chlor-4-fluor-phenyl)amino]-6-(cis-4-methylamino-cyclohexane-1-yloxy)-7-methoxy-chinazoline 4-[(3-Chlor-4-fluor-phenyl)amino]-6-{cis-4-[N-(2-methoxy-acetyl)-N-methyl-amino]-cyclohexane-1-yloxy}-7-methoxy-quinazoline 4-[(3-Ethinyl-phenyl)amino]-6-(piperidine-4-yloxy)-7-methoxy-quinazoline 4-[(3-Ethinyl-phenyl)amino]-6-[1-(2-methoxy-acetyl)-piperidine-4-yloxy]-7-methoxy-quinazoline 4-[(3-Ethinyl-phenyl)amino]-6-{1-[(morpholine-4-yl)carbonyl]-piperidine-4-yloxy}-7-methoxy-quinazoline 4-[(3-Chlor-4-fluor-phenyl)amino]-6-{1-[(cis-2,6-dimethyl-morpholine-4-yl)carbonyl]-piperidine-4-yloxy}-7-methoxy-quinazoline 4-[(3-Chlor-4-fluor-phenyl)amino]-6-{1-[(2-methyl-morpholine-4-yl)carbonyl]-piperidine-4-yloxy}-7-methoxy-quinazoline 4-[(3-Chlor-4-fluor-phenyl)amino]-6-{1-[(S,S)-(2-oxa-5-aza-bicyclo[2.2.1]hept-5-yl)carbonyl]-piperidine-4-yloxy}-7-methoxy-quinazoline 4-[(3-Chlor-4-fluor-phenyl)amino]-6-{1-[(N-methyl-N-2-methoxyethyl-amino)carbonyl]-piperidine-4-yloxy}-7-methoxy-quinazoline 4-[(3-Chlor-4-fluor-phenyl)amino]-6-(1-ethyl-piperidine-4-yloxy)-7-methoxy-quinazoline
4-[(3-Chlor-4-fluor-phenyl)amino]-6-{1-[(2-methoxyethyl)carbonyl]-piperidine-4-yloxy}-7-methoxy-quinazoline
4-[(3-Chlor-4-fluor-phenyl)amino]-6-{1-[(3-methoxypropyl-amino)-carbonyl]-piperidine-4-yloxy}-7-methoxy-quinazoline
4-[(3-Chlor-4-fluor-phenyl)amino]-6-[cis-4-(N-methansulfonyl-N-methyl-amino)-cyclohexane-1-yloxy]-7-methoxy-quinazoline
4-[(3-Chlor-4-fluor-phenyl)amino]-6-[cis-4-(N-acetyl-N-methyl-amino)-cyclohexane-1-yloxy]-7-methoxy-quinazoline
4-[(3-Chlor-4-fluor-phenyl)amino]-6-(trans-4-methylamino-cyclohexane-1-yloxy)-7-methoxy-quinazoline
4-[(3-Chlor-4-fluor-phenyl)amino]-6-[trans-4-(N-methansulfonyl-N-methyl-amino)-cyclohexane-1-yloxy]-7-methoxy-quinazoline
4-[(3-Chlor-4-fluor-phenyl)amino]-6-(trans-4-dimethylamino-cyclohexane-1-yloxy)-7-methoxy-quinazoline
4-[(3-Chlor-4-fluor-phenyl)amino]-6-(trans-4-{N-[(morpholine-4-yl)carbonyl]-N-methyl-amino}-cyclohexane-1-yloxy)-7-methoxy-quinazoline
4-[(3-Chlor-4-fluor-phenyl)amino]-6-[2-(2,2-dimethyl-6-oxo-morpholine-4-yl)-ethoxy]-7-[(S)-(tetrahydrofuran-2-yl)methoxy]-quinazoline
4-[(3-Chlor-4-fluor-phenyl)amino]-6-(1-methansulfonyl-piperidine-4-yloxy)-7-methoxy-quinazoline
4-[(3-Chlor-4-fluor-phenyl)amino]-6-(1-cyano-piperidine-4-yloxy)-7-methoxy-quinazoline
optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred dopamine antagonists which may be mentioned include Bromocriptine, Cabergoline, Alpha-Dihydroergocryptine, Lisuride, Pergolide, Pramipexole, Roxindole, Ropinirole, Talipexole, Terguride and Viozane, optionally in racemic form, as enantiomers, diastereomers or as pharmacologically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred antiallergic agents which may be mentioned include Epinastine, Cetirizine, Azelastine, Fexofenadine, Levocabastine, Loratadine, Mizolastine, Ketotifene, Emedastine, Dimetindene, Clemastine, Bamipine, Cexchlorpheniramine, Pheniramine, Doxylamine, Chlorphenoxamine, Dimenhydrinate, Diphenhydramine, Promethazine, Ebastine, Olopatadine, Desloratidine and Meclozine, optionally in racemic form, as enantiomers, diastereomers or as pharmacologically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred PAF antagonists which may be mentioned include Lexipafante and
4-(2-Chlorphenyl)-9-methyl-2-[3(4-morpholinyl)-3-propanone-1-yl]-6H-thieno-[3,2-f]-[1,2,4]triazolo[4,3-a][1,4]diazepine
6-(2-Chlorphenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine
optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred MAP kinase inhibitors which may be mentioned include
Bentamapimod (AS-602801)
Doramapimod (BIRB-796),
5-Carbamoylindole (SD-169),
6-[(aminocarbonyl)(2,6-difluorophenyl)amino]-2-(2,4-difluorophenyl)-3-pyridine carboxamide (VX-702),
alpha-[2-[[2-(3-pyridinyl)ethyl]amino]-4-pyrimidinyl]-2-benzothiazole acetonitrile (AS-601245),
9,12-Epoxy-1H-diindolo[1,2,3-fg:3',2',1'-kl]pyrrolo[3,4-i][1,6]benzodiazocine-10-Carboxylic acid (CEP-1347),
4-[3-(4-chlorophenyl)-5-(1-methyl-4-piperidinyl)-1H-pyrazole-4-yl]-pyrimidine (SC-409),
optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred MRP4-Inhibitors which may be mentioned include N-Acetyl-dinitrophenyl-Cysteine, cGMP, Cholate, Diclofenac, Dehydroepiandrosterone 3-glucuronide, Dehydroepiandrosterone 3-sulphate, Dilazep, Dinitrophenyl-5-glutathione, Estradiol 17-beta-glucuronide, Estradiol 3,17-disulphate, Estradiol 3-glucuronide, Estradiol 3-sulphate, Estrone 3-sulphate, Flurbiprofen, Folate, N5-formyl-tetrahydrofolate, Glycocholate, Glycolithocholic acid sulphate, Ibuprofen, Indomethacin, Indoprofen, Ketoprofen, Lithocholic acid sulphate, Methotrexate, (E)-3-[[[3-[2-(7-Chloro-2-quinolinyl)ethenyl]phenyl]-[[3-dimethylamino)-3-oxopropyl]thio]methyl]thio]-propanoic acid alpha-Naphthyl-beta-D-glucuronide, Nitrobenzyl mercaptopurine riboside, Probenecid, Valspodar, Sildenafil, Sulfinpyrazone, Taurochenodeoxycholate, Taurocholate, Taurodeoxycholate, Taurolithocholate, Taurolithocholic acid sulphate, Topotecan, Trequinsin, Zaprinast and Dipyridamol, optionally in racemic form, as enantiomers, diastereomers or as pharmacologically acceptable salts, solvates or hydrates.

Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred iNOS-Inhibitors which may be mentioned include S-(2-Aminoethyl)isothio-urea, Aminoguanidine, 2-Aminomethylpyridine, 5,6-dihydro-6-methyl-4H-1,3-thiazine-2-amine (AMT), L-Canavanin, 2-Iminopiperidine, S-Isopropylisothiourea, S-Methylisothiourea, S-Ethylisothiourea, S-Methylthiocitrulline, S-Ethylthiocitrulline, L-NA (N$^\omega$-Nitro-L-arginin), L-NAME (N$^\omega$-Nitro- L-argininmethylester), L-NMMA (N^ω-Monomethyl-L-arginin), L-NIO (N^ω-Iminoethyl-L-ornithin), L-NIL (N^ω-iminoethyl-lysin), (S)-6-Acetimidoylamino-2-amino-hexanoic acid (1H-tetrazole-5-yl)-amide N—[[3-(aminomethyl)phenyl]methyl]-ethanimidamide, (S)-4-(2-acetimidoylamino-ethylsulfanyl)-2-amino-buturic acid, 2-[2-(4-Methoxy-pyridine-2-yl)-ethyl]-3H-imidazo[4,5-b]pyridine, 2-((R)-3-amino-1-phenyl-propoxy)-4-chlor-5-fluorbenzonitrile, 2-((1R,3S)-3-amino-4-hydroxy-1-thiazole-5-yl-butylsulfanyl)-6-trifluoromethyl-nicotinonitrile, 2-((1R,3S)-3-amino-4-hydroxy-1-thiazole-5-yl-butylsulfanyl)-4-chlor-benzonitrile, 2-((1R,3S)-3-amino-4-hydroxy-1-thiazole-5-yl-butylsulfanyl)-5-chlor-benzonitrile, (2S,4R)-2-amino-4-(2-chlor-5-trifluoromethyl-phenylsulfanyl)-4-thiazole-5-yl-butane-1-ol, 2-((1R,3S)-3-amino-4-hydroxy-1-thiazole-5-yl-butylsulfanyl)-5-chlor-nicotinonitrile, 4-((S)-3-amino-4-hydroxy-1-phenyl-butylsulfanyl)-6-methoxy-nicotinonitrile and substituted 3-phenyl-3,4-dihydro-1-isoquinolinamine as for instance 1S,5S,6R)-7-Chlor-5-methyl-2-aza-bicyclo[4.1.0]hept-2-ene-3-ylamin (4R,5R)-5-Ethyl-4-methyl-thiazolidine-2-ylideneamine,(1S,5S,6R)-7-Chlor-5-methyl-2-aza-bicyclo[4.1.0]hept-2-ene-3-ylamin, (4R,5R)-5-Ethyl-4-methyl-thiazolidine-2-ylideneamine, (4R,5R)-5-Ethyl-4-methyl-selenazolidine-2-ylideneamine, 4-Aminotetrahydrobiopterine, (E)-3-(4-Chlor-phenyl)-N-(1-{2-oxo-2-[4-(6-trifluormethyl-pyrimidine-4-yloxy)-piperidine-1-yl]-ethylcarbamoyl}-2-pyridine-2-yl-ethyl)-acrylamide, 3-(2,4-Difluor-phenyl)-6-[2-(4-imidazole-1-ylmethyl-phenoxy)-ethoxy]-2-phenyl-pyridine, 3-{[(Benzo[1,3]dioxol-5-ylmethyl)-carbamoyl]-methyl}-4-(2-imidazole-1-yl-pyrimidine-4-yl)-piperazine-1-carbon acid methylester, (R)-1-(2-imidazole-1-yl-6-methyl-pyrimidine-4-yl)-pyrrolidine-2-carbon acid (2-benzo[1,3]dioxol-5-yl-ethyl)-amide, optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Further examples of preferred iNOS-Inhibitors which may be mentioned include antisense-Oligonucleotide, especially those antisense-Oligonucleotide binding iNOS-coding nucleinic acids, examples therefore are disclosed in WO 01/52902.

Examples of preferred SYK-inhibitors which may be mentioned include
2-[(2-aminoethyl)amino]-4-[(3-bromophenyl)amino]-5-pyrimidinecarboxamide;
2-[[7-(3,4-dimethoxyphenyl)imidazo[1,2-c]pyrimidine-5-yl]amino]-3-pyridinecarboxamide;
6-[[5-fluoro-2-[3,4,5-trimethoxyphenyl)amino]-4-pyrimidinyl]amino]-2,2-dimethyl-2H-pyrido[3,2-b]-1,4-oxazin-3 (4H)-one;
N-[3-bromo-7-(4-methoxyphenyl)-1,6-naphthyridine-5-yl]-1,3-propanediamine;
7-(4-methoxyphenyl)-N-methyl-1,6-naphthyridine-5-amine;
N-[7-(4-methoxyphenyl)-1,6-naphthyridine-5-yl]-1,3-propanediamine;
N-[7-(2-thienyl)-1,6-naphthyridine-5-yl-1,3-propanediamine;
N-[7-(4-(dimethylamino)phenyl]-1,6-naphthyridine-5-yl]-1,2-ethanediamine;
N-[7-(4-methoxyphenyl)-2-(trifluoromethyl)-1,6-naphthyridine-5-yl]-1,3-propanediamine;
N-[7-(4-methoxyphenyl)-3-phenyl-1,6-naphthyridine-5-yl]-1,3-propanediamine;
N-(7-phenyl-1,6-naphthyridine-5-yl)-1,3-propanediamine;
N-[7-(3-fluorophenyl)-1,6-naphthyridine-5-yl]-1,3-propanediamine;
N-[7-(3-chlorophenyl)-1,6-naphthyridine-5-yl]-1,3-propanediamine;
N-[7-[3-(trifluoromethoxy)phenyl]-1,6-naphthyridine-5-yl]-1,3-propanediamine;
N-[7-(4-fluorophenyl)-1,6-naphthyridine-5-yl]-1,3-propanediamine;
N-[7-(4-fluorophenyl)-1,6-naphthyridine-5-yl]-1,3-propanediamine;
N-[7-(4-chlorophenyl)-1,6-naphthyridine-5-yl]-1,3-propanediamine;
N-[7-(4'-methyl[1,1'-biphenyl]-4-yl)-1,6-naphthyridine-1,3-propanediamine;
N-[7-[4-(dimethylamino)phenyl]-1,6-naphthyridine-5-yl]-1,3-propanediamine;
N-[7-[4-(diethylamino)phenyl]-1,6-naphthyridine-5-yl]-1,3-propanediamine;
N-[7-[4-(4-morpholinyl)phenyl]-1,6-naphthyridine-5-yl]-1,3-propanediamine;
N-[7-[4-[[2-(dimethylamino)ethyl]methylamino]phenyl]-1,6-naphthyridine-5-yl]-1,3-propanediamine;
N-[7-(4-bromophenyl)-1,6-naphthyridine-5-yl]-1,3-propanediamine;
N-[7-(4-methylphenyl)-1,6-naphthyridine-5-yl]-1,3-propanediamine;
N-[7-[4-(methylthio)phenyl]-1,6-naphthyridine-5-yl]-1,3-propanediamine;
N-[7-[4-(1-methylethyl)phenyl]-1,6-naphthyridine-5-yl]-1,3-propanediamine;
7-[4-(dimethylamino)phenyl]-N-methyl-1,6-naphthyridine-5-amine;
7-[4-(dimethylamino)phenyl]-N,N-dimethyl-1,6-naphthyridine-5-amine;
N-[7-[4-(dimethylamino)phenyl]-1,6-naphthyridine-5-yl]-1,4-butanediamine;
N-[7-[4-(dimethylamino)phenyl]-1,6-naphthyridine-5-yl]-1,5-pentanediamine;
3-[[7-[4-(dimethylamino)phenyl]-1,6-naphthyridine-5-yl]oxy]-1-propanole;
4-[5-(4-aminobutoxy)-1,6-naphthyridine-7-yl]-N,N-dimethyl-benzenamine;
4-[[7-[4-(dimethylamino)phenyl]-1,6-naphthyridine-5-yl]amino]-1-butanole;
N-[7-[4-(dimethylamino)phenyl]-1,6-naphthyridine-5-yl]-N-methyl-1,3-propanediamine;
N-[7-[4-(dimethylamino)phenyl]-1,6-naphthyridine-5-yl]-N'-methyl-1,3-propanediamine;
N-[7-[4-(dimethylamino)phenyl]-1,6-naphthyridine-5-yl]-N,N'-dimethyl-1,3-propanediamine;
1-amino-3-[[7-[4-(dimethylamino)phenyl]-1,6-naphthyridine-5-yl]amino]-2-propanole;
N-[7-[4-(dimethylamino)phenyl]-1,6-naphthyridine-5-yl]-2,2-dimethyl-1,3-propanediamine;
7-[4-(dimethylamino)phenyl]-N-(3-pyridinylmethyl)-1,6-naphthyridine-5-amine;
N-[(2-aminophenyl)methyl]-7-[4-(dimethylamino)phenyl]-1,6-naphthyridine-5-amine;
N-[7-[6-(dimethylamino)[1,1'-biphenyl]-3-yl]-1,6-naphthyridine-5-yl]-1,3-propanediamine;
N-[3-chloro-4-(diethylamino)phenyl]-1,6-naphthyridine-5-yl]-1,3-propanediamine;
N-[7-[4-(dimethylamino)-3-methoxyphenyl]-1,6-naphthyridine-5-yl]-1,3-propanediamine;

N-[7-[4-(diethylamino)phenyl]-3-methyl-1,6-naphthyridine-5-yl]-1,3-propanediamine;
N-[7-(3'-fluoro[1,1'-biphenyl]-3-yl)-1,6-naphthyridine-5-yl]-1,2-ethanediamin,
N-[7-(4-methoxyphenyl)-1,6-naphthyridine-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridine-5-yl]-1,6-naphthyridine-1,3-propanediamine;
N5-(3-aminopropyl)-7-(4-methoxyphenyl)-N2-(phenylmethyl)-2,5-diamine;
N-[7-(2-naphthalenyl)-1,6-naphthyridine-5-yl]-1,3-propanediamine;
N-[7-(2'-fluoro[1,1'-biphenyl]-4-yl)-1,6-naphthyridine-5-yl]-1,3-propanediamine;
N-[7-(3,4,5-trim ethoxyphenyl)-1,6-naphthyridine-5-yl]-1,3-propanediamine;
N-[7-(3,4-dimethylphenyl)-1,6-naphthyridine-5-yl]-1,3-propanediamine;
1-amino-3-[[7-(2-naphthalenyl)-1,6-naphthyridine-5-yl]amino]-2-propanole;
1-amino-3-[[7-(2'-fluoro[1,1'-biphenyl]-4-yl)-1,6-naphthyridine-5-yl]amino]-2-propanole;
1-amino-3-[[7-(4'-methoxy[1,1'-biphenyl]-4-yl)-1,6-naphthyridine-5-yl]amino]-2-propanole;
1-amino-3-[[7-(3,4,5-trimethoxyphenyl)-1,6-naphthyridine-5-yl]amino]-2-propanole;
1-amino-3-[[7-(4-bromophenyl)-1,6-naphthyridine-5-yl]amino]-2-propanole;
N-[7-(4'-methoxy[1,1'-biphenyl]-4-yl)-1,6-naphthyridine-5-yl]-2,2-dimethyl-1,3-propanediamine;
1-[[7-[4-(dimethylamino)phenyl]-1,6-naphthyridine-5-yl]amino]-2-propanole;
2-[[2-[[7-[4-(dimethylamino)phenyl]-1,6-naphthyridine-5-yl]amino]ethyl]thio]-ethanole;
7-[4-(dimethylamino)phenyl]-N-(3-methyl-5-isoxazolyl)-1,6-naphthyridine-5-amine;
7-[4-(dimethylamino)phenyl]-N-4-pyrimidinyl-1,6-naphthyridine-5-amine;
N-[7-[4-(dimethylamino)phenyl]-1,6-naphthyridine-5-yl]-1,3-cyclohexane diamine;
N,N-dimethyl-4-[5-(1-piperazinyl)-1,6-naphthyridine-7-yl]-benzenamine;
4-[5-(2-methoxyethoxy)-1,6-naphthyridine-7-yl]-N,N-dimethyl-benzenamine;
1-[7-[4-(dimethylamino)phenyl]-1,6-naphthyridine-5-yl]-4-piperidinole;
1-[7-[4-(dimethylamino)phenyl]-1,6-naphthyridine-5-yl]-3-pyrrolidinole;
7-[4-(dimethylamino)phenyl]-N-(2-furanylmethyl)-1,6-naphthyridine-5-amine;
7-[4-(dimethylamino)phenyl]-N-[3-(1H-imidazole-1-yl)propyl]-1,6-naphthyridine-5-amine;
1-[7-[4-(dimethylamino)phenyl]-1,6-naphthyridine-5-yl]-4-piperidine carboxamide;
1-[3-[[7-[4-(dimethylamino)phenyl]-1,6-naphthyridine-5-yl]amino]propyl]-2-pyrrolidinone;
N-[3'-[5-[(3-aminopropyl)amino]-1,6-naphthyridine-7-yl][1,1'-biphenyl]-3-yl]-acetamide;
N-[7-(4'-fluoro[1,1'-biphenyl]-4-yl)-1,6-naphthyridine-5-yl]-1,3-propanediamine;
N-[4'-[5-[(3-aminopropyl)amino]-1,6-naphthyridine-7-yl][1,1'-biphenyl]-3-yl]-acetamide;
N-[7-[4-(1,3-benzodioxol-5-yl)phenyl]-1,6-naphthyridine-5-yl]-1,3-propanediamine;
N-[7-[4-(2-thienyl)phenyl]-1,6-naphthyridine-5-yl]-1,3-propanediamine;
N-[7-[4-fluoro-3-(trifluoromethyl)phenyl]-1,6-naphthyridine-5-yl]-1,3-propanediamine;
N-[7-[4-(3-pyridinyl)phenyl]-1,6-naphthyridine-5-yl]-1,3-propanediamine;
N-[7-(1,3-benzodioxol-5-yl)-1,6-naphthyridine-5-yl]-1,3-propanediamine;
N-[7-(6-methoxy-2-naphthalenyl)-1,6-naphthyridine-5-yl]-1,3-propanediamine;
7-[4-(dimethylamino)phenyl]-N-(4-pyridinylmethyl)-1,6-naphthyridine-5-amine;
3-[[7-[4-(dimethylamino)phenyl]-1,6-naphthyridine-5-yl]methylamino]-propanenitrile;
7-[4-(dimethylamino)phenyl]-N-[1-(phenylmethyl)-4-piperidinyl]-1,6-naphthyridine-5-amine;
N-[7-[4-(dimethylamino)phenyl]-1,6-naphthyridine-5-yl]-1,2-cyclohexanediamin,
N-[7-[4-(dimethylamino)phenyl]-1,6-naphthyridine-5-yl]-1,2-Cyclohexanediamine, (1R,2S)-rel-.
N-[7-[4-(dimethylamino)phenyl]-1,6-naphthyridine-5-yl]-1,2-benzene dimethanamine;
N-[7-[4-(diethylamino)phenyl]-1,6-naphthyridine-5-yl]-1,4-butanediamine;
N-[7-[3',5'-bis(trifluoromethyl)[1,1'-biphenyl]-4-yl]-1,6-naphthyridine-5-yl]-,3-propanediamine;
N-[7-(3'-methoxy[1,1'-biphenyl]-4-yl)-1,6-naphthyridine-5-yl]-1,3-propanediamine;
N-[7-(3'-fluoro[1,1'-biphenyl]-4-yl)-1,6-naphthyridine-5-yl]-1,3-propanediamine;
4-[[7-[4-(dimethylamino)phenyl]-1,6-naphthyridine-5-yl]oxy]-1-butanole;
N-[7-[4-(dimethylamino)phenyl]-1,6-naphthyridine-5-yl]-1,4-cyclohexanediamine;
7-[4-(dimethylamino)phenyl]-N-(2,2,6,6-tetramethyl-4-piperidinyl)-1,6-naphthyridine-5-amine;
N-[7-[3-bromo-4-(dimethylamino)phenyl]-1,6-naphthyridine-5-yl]-1,3-propanediamine;
N-[7-(1-methyl-1H-indole-5-yl)-1,6-naphthyridine-5-yl]-1,3-propanediamine;
N-[7-(3-(trifluoromethyl)phenyl]-1,6-naphthyridine-5-yl]-1,3-propanediamine;
N-[7-[4-(trifluoromethyl)phenyl]-1,6-naphthyridine-5-yl]-1,3-propanediamine;
N-[7-(3-bromo-4-methoxyphenyl)-1,6-naphthyridine-5-yl]-1,3-propanediamine;
N-[7-[4-[[3-(dimethylamino)propyl]methylamino]phenyl]-1,6-naphthyridine-5-yl]-1,4-cyclohexanediamine;
N-[7-[4-[[2-(dimethylamino)ethyl]methylamino]phenyl]-1,6-naphthyridine-5-yl]-1,4-cyclohexanediamine;
N-[7-[4-(dimethylamino)-3-methoxyphenyl]-1,6-naphthyridine-5-yl]-1,4-cyclohexanediamine;
N-[7-[4-(4-morpholinyl)phenyl]-1,6-naphthyridine-5-yl]-1,4-cyclohexanediamine;
N-[7-[3-bromo-4-(4-morpholinyl)phenyl]-1,6-naphthyridine-5-yl]-1,4-cyclohexanediamine;
4-[[7-[4-[[2-(dimethylamino)ethyl]methylamino]phenyl]-1,6-naphthyridine-5-yl]oxy]-cyclohexanole;
N-[7-[3-bromo-4-(4-morpholinyl)phenyl]-1,6-naphthyridine-5-yl]-1,3-propanediamine;
N,N-dimethyl-4-[5-(4-methyl-1-piperazinyl)-1,6-naphthyridine-7-yl]-benzenamine;
4-[[7-[4-[[3-(dimethylamino)propyl]methylamino]phenyl]-1,6-naphthyridine-5-yl]oxy]-cyclohexanole;
N-[7-[4-[[2-(dimethylamino)ethyl]methylamino]phenyl]-1,6-naphthyridine-5-yl]-1,4-butanediamin;

[3-[[5-[(3-aminopropyl)amino]-7-(4-methoxyphenyl)-1,6-naphthyridine-2-yl]amino]propyl]-carbamic acid-1,1-dimethylethyl ester, optionally in racemic form, as enantiomers, diastereomers or as pharmacologically acceptable salts, solvates or hydrates. Preferred are salts selected from the group consisting of hydrochloride, hydrobromide, hydroiodide, hydrosulfate, hydrophosphate, hydromethansulfonate, hydronitrate, hydromaleate, hydroacetate, hydrocitrate, hydrofumarate, hydrotartrate, hydrooxalate, hydrosuccinate, hydrobenzoate and hydro-p-toluenesulfonate.

Examples of preferred corrections of the cystic fibrosis transmembrane regulator (CFTR) and CFTR potentiators which may be mentioned include, preferably VX-770 and VX-809

12. Formulations

Suitable forms for administration are for example inhalable powders or aerosols. The content of the pharmaceutically effective compound(s) in each case should be in the range from 0.2 to 50 wt %, preferably 5 to 25 wt. % of the total composition, i.e. in amounts which are sufficient to achieve the dosage range specified hereinafter.

Administered by inhalation the active substance combination may be given as a powder, as an aqueous or aqueous-ethanolic solution or using a propellant gas formulation.

Preferably, therefore, pharmaceutical formulations are characterised in that they contain one or more compounds of (I) according to the preferred embodiments above.

It is also preferred if the compounds of formula (I) are administered by inhalation, particularly preferably if they are administered once or twice a day. For this purpose, the compounds of formula (I) have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also include concentrates or sterile ready-to-use inhalable solutions. The preparations which may be used according to the invention are described in more detail in the next part of the specification.

Inhalable Powders

If the active substances of formula (I) are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-containing Inhalable Aerosols

The propellant-containing inhalable aerosols which may be used according to the invention may contain a compound of formula (I) dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-free Inhalable Solutions

The compounds of formula (I) according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, a compound according to the invention and one or more combination partners selected from those described above.

The following example illustrates the present invention without restricting its scope:

Capsule for Powder Inhalation
1 capsule contains:

| active substance | 0.5 mg |
|---|---|
| lactose for inhalation | 5.0 mg |
| | 5.5 mg |

Preparation:
The active substance is mixed with lactose for inhalation. The mixture is packed into capsules in a capsule-making machine (weight of the empty capsule approx. 50 mg).

| weight of capsule: | 55.5 mg |
|---|---|
| size of capsule = | 3 |

The invention claimed is:

1. A compound of formula (I), (I)

[structure of formula (I) showing pyrazine ring with $R^1$, $NH_2$, $H_2N$, and side chain $-C(O)-N=C(NH_2)-NH-L^1-L^2-L^3$, with counterion $X^-$]

characterized in that
$R^1$ denotes halogen,
$X^-$ denotes acetate, halide, sulfate, hydrogen sulfate, succinate, malate, hydrogen carbonate, sulfate ×0.5 or carbonate ×0.5,
$L^1$ denotes a group of formula (i), (i)

[structure showing pyrrolidinium ring with substituents $(-)_m$, $(-)_n$, $N^+$ bearing $R^{L1}$ and $L^2$, and N-H]

wherein
$R^{L1}$ denotes $C_{1-6}$-alkyl, or
$R^{L1}$ denotes a $C_{1-6}$-alkylene bridge by replacing one of the hydrogen atoms of formula (i), forming a bicyclic ring system,
n and m independently from each other denote 1, 2 or 3,
$L^2$ denotes —$CH_2$— or —$CH(C(O)NHR^{L2})$—, wherein
$R^{L2}$ denotes H, $C_{1-8}$-alkyl, phenyl, $C_{6-10}$-aryl-$C_{5-6}$-cycloalkyl-, $C_{6-10}$-aryl-$C_{1-4}$-alkyl-, HO—$C_{2-6}$-alkyl-, $C_{1-4}$-alkoxy-, $C_{1-4}$-alkoxy-$C_{2-6}$-alkyl, heteroaryl, C-linked hererocyclyl, C-linked herecyclyl-$C_{1-4}$-alkyl, C-linked heterocyclyl-COO—$C_{1-4}$-alkyl-, aryl- heterocyclyl-$C_{1-4}$-alkyl, N-linked heterocyclyl-$C_{2-4}$-alkyl, $C_{6-10}$-aryl-(HOOC)$C_{1-4}$-alkyl-, —CH($C_{1-3}$-alkyl-$C_{6-10}$-aryl)(COO—$C_{1-4}$-alkyl),—CH($C_{1-3}$-alkyl-$C_{6-10}$-aryl)(COOH), —$C_{1-3}$-alkyl-$C_{6-10}$-aryl-COO—$C_{1-4}$-alklyl, —$C_{6-10}$-aryl-COO—$C_{1-4}$-alkyl or —$C(R^{3.1}R^{3.2})$phenyl,
wherein
$R^{3.1}R^{3.2}$ together with the carbon atom they are attached to form a 5-7 -membered heterocyclyl.
$L^3$ denotes hydrogen, —COOH, —CO-phenyl, —COO—$C_{1-3}$-alkyl, —COO—$C_{1-3}$-alkyl-$C_{6-10}$-aryl-$C_{6-10}$-aryl-COO—$C_{1-4}$-alkyl, —C(O)NR$^2$R$^3$, heteroaryl, $C_{1-3}$-alkyl, $C_{2-5}$-alkenyl, $C_{2-3}$-alkynyl, $C_{3-7}$-cycloalkyl, $C_{5-7}$-cycloalkenyl, HO—$C_{1-7}$-alkyl-, $C_{1-4}$-alkoxy-$C_{1-5}$-alkyl-, $C_{1-4}$-alkyl-$S(O)_p$—$C_{1-3}$-alkyl-, C-linked heterocyclyl, —CO-heterocyclyl, —CO—heterocyclyl-heteroaryl, —CO—heterocyclyl—COO—$C_{1-4}$-alkyl, —CO-heterocyclyl—COOH—CN, or phenyl of formula (ii), (ii)

[benzene ring with substituents $R^{L3.1}$, $R^{L3.2}$, $R^{L3.3}$, $R^{L3.4}$, $R^{L3.5}$ and attachment point *]

$R^{L3.1}$, $R^{L3.2}$, $R^{L3.3}$, $R^{L3.4}$ and $R^{L3.5}$ independently -denote H, —OH, —O—$C_{1-4}$-alkyl, $C_{1-4}$-alkyl, —S—$C_{1-4}$-alkyl, —S—$CF_3$, —$CF_3$, —O—$CH_2$-phenyl, —O—$CF_3$, —$CH_2$—OH, —$CH_2$COOH, halogen, —$SO_2$—$C_{1-4}$-alkyl , —COO—$C_{1-4}$-alkyl, —$CONH_2$, —$C_{1-4}$-alkyl-phenyl-CN, —CONH$C_{1-4}$-alkyl, —CON($C_{1-4}$-alkyl)$_2$, —CO—NH-heterocyclyl, or CN,
wherein,
p is 0, 1 or 2,
$R^2$ and $R^3$ independently denote H, $C_{1-8}$-alkyl, phenyl, $C_{6-10}$-aryl-$C_{5-6}$-cycloalkyl-, $C_{6-10}$-aryl-$C_{1-4}$-alkyl- wherein said $C_{6-10}$-aryl may be substituted with —Cl, —CN, —C(O)OCH$_3$, or —C(O)OH, HO—$C_{2-6}$-alkyl-, $C_{1-4}$-alkoxy-, $C_{1-4}$-alkoxy-$C_{2-6}$-alkyl-, heteroaryl, C-linked heterocyclyl, C-linked heterocyclyl-$C_{1-4}$-alkyl, C-linked heterocyclyl—COO—$C_{1-4}$-alkyl-, aryl-C-linked heterocyclyl-$C_{1-4}$-alkyl, N-linked heterocyclyl-$C_{2-4}$-alkyl, $C_{6-10}$-aryl-(HOOC)$C_{1-4}$-alkyl-, —CH($C_{1-3}$-alkyl-$C_{6-10}$-aryl)(COO—$C_{1-4}$-alkyl), —CH($C_{1-3}$-alkyl-$C_{6-10}$-aryl)(COOH), —$C_{1-3}$-alkyl-$C_{6-10}$-aryl-COO—$C_{1-4}$-alkyl, —$C_{6-10}$-aryl-COO—$C_{1-4}$-alkyl or —$C(R^{3.1}R^{3.2})$phenyl, wherein R[3.1]R[3.2] together with the carbon atom they are attached to form a 5-7-membered heterocyclyl, or R[2] and R[3] together with the nitrogen atom they are attached to form a 5-7-membered heterocyclyl, optionally substituted by a carboxylic acid or a heterroaryl, and tautomers and pharmaceutically acceptable salts thereof.

2. A compound of formula (I) according to claim 1, characterized in that

L[1] denotes a group of formula (i.1), (i.2) or (i.3)

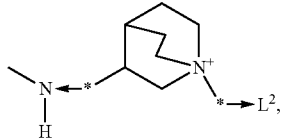
(i.1)

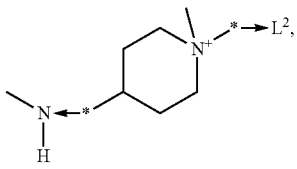
(i.2)

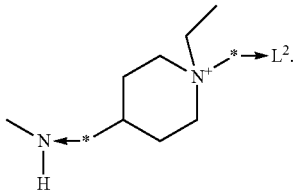
(i.3)

3. A pharmaceutical composition comprising at least one compound according to claim 1 or a pharmaceutically acceptable salt thereof and a pharmaceutically acceptable carrier.

* * * * *